(12) United States Patent
Heartlein et al.

(10) Patent No.: US 8,945,542 B2
(45) Date of Patent: Feb. 3, 2015

(54) METHODS FOR TREATING LYSOSOMAL ACID LIPASE DEFICIENCY

(71) Applicant: Synageva Biopharma Corp., Lexington, MA (US)

(72) Inventors: Michael Heartlein, Boxborough, MA (US); Michael Concino, Bolton, MA (US); Paolo Martini, Boston, MA (US); Muthuraman Meiyappan, Jamaica Plain, MA (US); Pericles Calias, Melrose, MA (US); Alla Romashko, Lexington, MA (US); Brian Pescatore, Beverly, MA (US); Lawrence Charnas, Natick, MA (US); Jan Powell, Concord, MA (US); Brian Felice, Wellesley, MA (US); Nancy Savioli, Billerica, MA (US)

(73) Assignee: Synageva Biopharma Corp., Lexington, MA (US)

( * ) Notice: Subject to any disclaimer, the term of this patent is extended or adjusted under 35 U.S.C. 154(b) by 0 days.

(21) Appl. No.: 13/967,050

(22) Filed: Aug. 14, 2013

(65) Prior Publication Data
US 2014/0044697 A1    Feb. 13, 2014

Related U.S. Application Data

(63) Continuation of application No. PCT/US2012/025239, filed on Feb. 15, 2012.

(60) Provisional application No. 61/443,179, filed on Feb. 15, 2011.

(51) Int. Cl.
*A61K 38/46* (2006.01)

(52) U.S. Cl.
CPC .................................... *A61K 38/465* (2013.01)
USPC ........................................ 424/94.6; 424/94.1

(58) Field of Classification Search
CPC ........ A61K 38/465; C12N 9/20; C12N 15/52; C12P 21/005
See application file for complete search history.

(56) References Cited

U.S. PATENT DOCUMENTS

| 5,767,115 | A | 6/1998 | Rosenblum et al. |
|---|---|---|---|
| 5,929,304 | A | 7/1999 | Radin et al. |
| 6,534,300 | B1 | 3/2003 | Canfield |
| 6,670,165 | B2 | 12/2003 | Canfield |
| 6,800,472 | B2 | 10/2004 | Canfield et al. |
| 6,849,257 | B2 | 2/2005 | Grabowski et al. |
| 7,033,780 | B1 | 4/2006 | McCarthy et al. |
| 8,178,609 | B2 | 5/2012 | Grynkiewicz et al. |
| 8,183,003 | B2 | 5/2012 | Crawford et al. |
| 8,232,073 | B2 | 7/2012 | Crawford et al. |
| 8,663,631 | B2 | 3/2014 | Quinn |
| 2002/0193303 | A1 | 12/2002 | Kapeller-Libermann |
| 2003/0059420 | A1 | 3/2003 | Grabowski et al. |
| 2003/0064467 | A1 | 4/2003 | Baker et al. |
| 2004/0038365 | A1 | 2/2004 | Xiao |
| 2004/0175798 | A1 | 9/2004 | Wan et al. |
| 2004/0223960 | A1 | 11/2004 | Grabowski et al. |
| 2005/0112691 | A1 | 5/2005 | Callewaert et al. |
| 2005/0181474 | A1 | 8/2005 | Giordano et al. |
| 2007/0009500 | A1 | 1/2007 | Blazar et al. |
| 2007/0264249 | A1 | 11/2007 | Grabowski et al. |
| 2007/0270367 | A1 | 11/2007 | Testa et al. |
| 2008/0025958 | A1 | 1/2008 | Hannon et al. |
| 2008/0206223 | A1 | 8/2008 | Van Bree et al. |
| 2008/0249287 | A1 | 10/2008 | Rossomando et al. |
| 2008/0255050 | A1 | 10/2008 | Guo |
| 2008/0292618 | A1 | 11/2008 | Weisbart |
| 2009/0178147 | A1 * | 7/2009 | Harvey .............................. 800/4 |
| 2009/0297496 | A1 | 12/2009 | Grabowski |
| 2010/0062982 | A1 | 3/2010 | Harvey |
| 2010/0160253 | A1 | 6/2010 | Coombe et al. |
| 2010/0184947 | A1 | 7/2010 | Kuik-Romeijn et al. |
| 2010/0196393 | A1 | 8/2010 | Banks et al. |
| 2010/0233084 | A1 | 9/2010 | Narasimhaswamy et al. |
| 2010/0291060 | A1 | 11/2010 | Sturk et al. |
| 2011/0091442 | A1 | 4/2011 | Boyd et al. |
| 2011/0213328 | A1 | 9/2011 | Keimel et al. |
| 2011/0230416 | A1 | 9/2011 | Khrestchatisky et al. |

(Continued)

FOREIGN PATENT DOCUMENTS

| EP | 1267914 | 4/2009 |
|---|---|---|
| WO | WO 92/16212 | 10/1992 |

(Continued)

OTHER PUBLICATIONS

Du, H. et al. 2002. Lysosomal acid lipase deficiency: Correction of lipid storage by adenovirus-mediated gene transfer in mice. Human Gene Therapy 13:1361-1372. specif. pp. 1361-1363, 1364 and 1368-1369.*

ATCC. 293 [HEK-293]. Datasheet [online]. American Tissue Culture Collection. Copyright 2012 [retrieved on Dec. 11, 2013]. Retrieved from the Internet: <URL: http://www.atcc.org/products/all/CRL-1573.aspx>.*

Donovan, J. et al. 2005. Use of Mouse, Rat, Hamster, and Rabbit. Parenteral Injections. Unit 1.6. In: Current Protocols in Immunology. John Wiley and Sons, Inc. Copyright 2006 73:1.6.1-1.6.10. specif. p. 2, Table 1.6.1.*

Du, H. et al. 2001. Enzyme therapy for lysosomal acid lipase deficiency in the mouse. Human Molecular Genetics 10(16)1639-1648. specif. p. 1639.*

(Continued)

*Primary Examiner* — John S Brusca
*Assistant Examiner* — Sharon M Papciak
(74) *Attorney, Agent, or Firm* — McDermott Will & Emery LLP

(57) ABSTRACT

The present invention provides compositions and methods for effective treatment of a lysosomal acid lipase deficiency (LALD) disease, in particular, Wolman's disease and Cholesteryl Ester Storage Disease (CESD). Among other things, the present invention provides a method of treating developmental impairment or malnutrition in an individual suffering from a lysosomal acid lipase deficiency (LALD) disease, comprising administering to the individual a therapeutic effective amount of a lysosomal acid lipase.

3 Claims, 50 Drawing Sheets

(56) References Cited

U.S. PATENT DOCUMENTS

| | | |
|---|---|---|
| 2012/0064055 A1 | 3/2012 | Quinn |
| 2012/0190642 A1 | 7/2012 | Grynkiewicz et al. |
| 2012/0232133 A1 | 9/2012 | Balazs et al. |
| 2012/0288447 A1 | 11/2012 | Lee et al. |
| 2013/0095092 A1 | 4/2013 | Quinn et al. |
| 2013/0209436 A1 | 8/2013 | Quinn et al. |
| 2013/0273021 A1 | 10/2013 | Quinn et al. |

FOREIGN PATENT DOCUMENTS

| | | |
|---|---|---|
| WO | WO 95/08532 | 3/1995 |
| WO | WO 96/04001 | 2/1996 |
| WO | WO 97/05771 | 2/1997 |
| WO | WO 98/11206 | 3/1998 |
| WO | WO 00/09153 | 2/2000 |
| WO | WO 00/77239 | 12/2000 |
| WO | WO 01/56596 | 8/2001 |
| WO | WO 01/97829 | 12/2001 |
| WO | WO 2007/030375 | 3/2007 |
| WO | WO 2007/137303 | 11/2007 |
| WO | WO 2011/133960 | 10/2011 |
| WO | WO 2012/112677 | 8/2012 |
| WO | WO 2012/112681 | 8/2012 |
| WO | WO 2012/159052 | 11/2012 |
| WO | WO 2012/162807 | 12/2012 |
| WO | WO 2012/177639 | 12/2012 |
| WO | WO 2012/177778 | 12/2012 |
| WO | WO 2013/020064 | 2/2013 |

OTHER PUBLICATIONS

Du, H. et al. 2008. Wolman disease/choleteryl ester storage disease: efficacy of plant-produced human lysosomal acid lipase in mice. Journal of Lipid Research 49:1646-1657. specif. 1651.*
U.S. Appl. No. 13/649,595, filed Apr. 18, 2013, Synageva Biopharma Corp.
U.S. Appl. No. 13/583,973, filed Oct. 17, 2013, Synageva Biopharma Corp.
Synageva Biopharma Corp., and Synageva Biopharma Limited, plaintiffs v. Children's Hospital Research Foundation, Children's Hospital Research Foundation, Cincinnati, Ohio and Children's Hospital Medical Center, defendants, Summons Before the High Court of Paris ( including Translation of same) 91 pages.
Coates et al, Genetic Variation of Human Mononuclear Leukocyte Lysosomal Acid Lipase Activity, Atherosclerosis, 65:11-20 (1968).
Zschenker, O. et al. Systematic Mutagenesis of Potential Glycosylation Sites of Lysosomal Acid Lipase, J. Biochem. 2005, vol. 137, No. 3, pp. 387-394.
Skropeta, D. The effect of individual N-glycans on enzyme activity, Bioorg. Med. Chem. 2009, vol. 17, pp. 2645-2653.
Pariyarathuparambil, R.: 'Human lysosomal acid lipase: functional characterization by molecular genetic analysis and site-directed mutagenesis studies.' SISSA Digital Library Phd Thesis, [Online] 1995, Retrieved from the Internet: [retrieved on Aug. 5, 2012].
Third Party Pre-issuance Submission in U.S. Appl. No. 13/229,558 dated Dec. 31, 2012, 22 pages.
Abramov et al., "Generalized Xanthomatosis with Calcified Adrenals," Journal of Diseases of Children, pp. 282-286 (1956).
Achord et al., "Human β-Glucuronidase: In Vivo Clearance and in Vitro Uptake by a Glycoprotein Recognition System on Reticuloendothelial Cells," Cell, 15:269-278 (1978).
Ahn et al., "Identification of the Genes Differently Expressed in Human Dendritic Cell Subsets by cDNA Subtraction and Microarray Analysis," Blood, 100:1742-1754 (2002).
Akcoren et al., Cholesteryl Ester Storage Disease: Case Report During Childhood, Pediatric and Developmental Pathology 2:574-576 (1999).
Al Essa et al., "Wolman Disease: A Review," Curr Paed Res, 3(1):1-12 (1999).
Albrecht Dehmel, Opposition Submission 1, European Patent Register: 1-56 (Jan. 28, 2010).
Albrecht Dehmel, Opposition Submission 2, European Patent Register: 1-17 (Apr. 4, 2011).
Albrecht Dehmel, Opposition Submission 3, European Patent Register: 1-8, Aug. 22, 2011.
Ameis et al., "A 5' Splice-Region Mutation and a Dinucleotide Deletion in the Lysosomal Acid Lipase Gene in Two Patients with Cholesteryl Ester Storage Disease," Journal of Lipid Research, 36: 241-250 (1995).
Ameis et al., "Lysosomal acid lipase: A pivotal enzyme in the pathogenesis of cholesteryl ester storage disease and Wolman disease," Z Gastroenterol (Suppl. 3) 34: 66-67 (1996).
Ameis et al., Purification, characterization, and molecular cloning of human hepatic lysosomal acid lipase; Eur. J. Biochem., 219(3): 905-914 (1994).
Anderson et al., "In Situ Localization of the Genetic Locus Encoding the lysosomal acid lipase/cholesteryl esterase (LIPA) deficient in Wolman Disease to chromosome 10q23.2q23.3," Genomics, 15: 245-247 (1993).
Anderson et al., Cloning and Expression of cDNA encoding human lysosomal acid lipase/cholesteryl ester hydrolase, J. Biol. Chem, 266: 224798-22484 (1991).
Anderson et al., Lysosomal acid lipase mutations that determine phenotype in Wolman and cholesterol ester storage disease, Mol. Genet. Metab., 68: 333-345 (1999).
Anderson, Mutations at the lysosomal acid cholesteryl ester hydrolase gene locus in Wolman disease, PNAS, 91: 2718-2722 (1994).
Arterburn et al., Orthotopic Liver Transplantation for Cholesteryl ester storage disease, J. Clinical Gastroenteroly, 13: 482-485 (1991).
Aslandis et al., Genetic and biochemical evidence that CESD and Wolan Disease are distinguished by residual lysosomal acid lipase activity, Genomics, 33: 85-93 (1996).
Aslanidis et al., "Genomic Organization of the Human Lysosomal Acid Lipase Gene (LIPA)," Genomics, 20:329-331 (1994).
Assmann et al., "Chapter 142: Acid Lipase Deficiency: Wolman Disease and Cholesteryl Ester Storage Disease," Part 16: Lysosomal Disorders, Scriver's OMMBID: The Online Metabolic & Molecular Bases of Inherited Disease, :1-49 (2001).
Asumendi et al., "Hepatic Sinusoidal Endothelium Heterogeneity with Respect to Mannose Receptor Activity is Interleukin-1 Dependent," Hepatology, 23(6): 1521-1529 (1996).
Avart et al., "Cholesteryl Ester Hydrolysis in J774 Macrophages Occurs in the Cytoplasm and Lysosomes," Journal of Lipid Research, 40: 405-414 (1999).
Baenziger et al., "Structural Determinants of Concanavalin a Specificity for Oligosaccharides," J. of Biol. Chem., 254(7): 2400-2407(1979).
Bailey, An overview of enzyme replacement therapy for lysosomal storage diseases, The Online Journal of Issues in Nursing 13(1) Manuscript, 3: 1-14 (2008).
Barton et al., "Replacement Therapy for Inherited Enzyme Deficiency—Macrophage Targeted Glucocerebrosidase for Gaucher's Disease," The New England Journal of Medicine, 324(21) : 1464-1470(1991).
Barton et al., "Therapeutic Response to Intravenous Infusions of Glucocerebrosidase in a Patient with Gaucher Disease," Proc. Nat. Acad. Sci. USA, 87: 1913-1916 (1990).
Beaudet et al., "Acid lipase in cultured fibroblasts: cholesterol ester storage disease," J. Lab. Clin. Med., 84:54-55 (1974).
Beaudet et al., "Cholesterol Ester Storage Disease: Clinical, Biochemical, and Pathological Studies," The Journal of Pediatrics, 90(6):910-914 (1977).
Begley et al., "Lysosomal Storage Diseases and the Blood-Brain Barrier," Current Pharmaceutical Design, 14-16:1566-1580 (2008).
Bertrand et al., "Transport Characteristics of a Novel Peptide Platform for CNS Therapeutics," J Cellular Molecular Medicine, 14 (12):2827-2839 (2010).
Besley et al., Cholesterol ester storage disease in an adult presenting with sea-blue histocytosis, Clin. Genet., 26: 195-203 (1984).
Beutler et al., "Enzyme Replacement Therapy for Gaucher Disease," Blood, 78(5):1183-1189.
Biggs et al., "A Manual Colorimetric Assay of Triglycerides in Serum," Clinical Chemistry, 21(3):437-441 (1975).

(56) References Cited

OTHER PUBLICATIONS

Bijsterbosch et al., "Quantitative Analysis of the Targeting of Mannose-Terminal Glucocerebrosidase Predominant Uptake by Liver Endothelial Cells," Eur. J. Biochem, 237:344-349 (1996).
Bindu et al., "Cholesterol Ester Storage Disease with Unusual Neurological Manifestations in Two Siblings: A Report from South India," Journal of Child Neurology, 22(12):1401-1405 (2007).
Boldnni et al., Wolman disease and cholesteryl ester storage disease diagnosed by histological and ultrastructural examination of intestinal and liver biopsy, Path Res. Practice, 200: 231-240 (2004).
Brady et al., "Modifying Exogenous Glucocerebrosidase for Effective Replacement Therapy in Gaucher Disease," J. Inher. Metab. Dis., 17:510-519 (1994).
Brecher et al., "Effect of Atherosclerosis on Lysosomal Cholesterol Esterase Activity in Rabbit Aorta," Journal of Lipid Research, 18:154-160 (1977).
Briggs et al., "Nuclear Protein that Binds Sterol Regulatory Element of Low Density Lipoprotein Receptor Promoter," J. Biol. Chem., 268(19): 14490-14496 (1993).
Brown et al., "Restoration of a regulatory response to low density lipoprotein in acid lipase-deficient human fibroblast." J. of Biol. Chem. 251: 3277-3286 (1976).
Brown et al., "A Receptor-Mediated Pathway for Cholesterol Homeostasis," Science, 232(4746): 34-47 (1986).
Brown et al., "Multivalent Feedback Regulation of HMG CoA Reductase, a Control Mechanism Coordinating Isoprenoid Synthesis and Cell Growth," Journal of Lipid Research, 21: 505-517 (1980).
Brown et al., "Use of Nile Red Stain in the Detection of Cholesteryl Ester Accumulation in Acid Lipase-Deficient Fibroblasts," Arch Pathol Lab Med, 112: 295-296 (1988).
Brumshtein et al., "Characterization of Gene-Activated Human Acid-13-Glucosidase: Crystal Structure, Glycan Composition, and Internalization into Macrophages," Glycobiology, 20(1): 24-32 (2010).
Brumshtein et al., "Structural Comparison of Differently Glycosylated Forms of acid-13-Glucosidase, the defective Enzyme in Gaucher Disease," Acta Crystallographica Section D, 62: 1458-1465 (2006).
Burke et al., Deficient Activity of Hepatic Acid Lipase in Cholesterol Ester Storage Disease, Science, 176 (4032): 309-310 (1972).
Burton et al., "Purification and Properties of Human Placental Acid Lipase," Biochimica et Biophysica Acta, 618:449-460(1980).
Burton et al., "Lysosomal Acid Lipase in Cultivated Fibroblasts:Characterization of Enzyme Activity in Normal and Enzymatically Deficient Cell Lines," Clinica Chimica Acta, 101:25-32 (1980).
Burton et al., "Acid Lipase Cross-Reacting Material in Wolman Disease and Cholesterol Ester Storage Disease," Am J Hum Genet, 33:203-208 (1981).
Byrd et al., "Wolman's Disease: Ultrastructural Evidence of Lipid Accumulation in Central and Peripheral Nervous Systems," Acta Neuropathol, 45:37-42 (1979).
Cagle et al., "Clinicopathologic Conference: Pulmonary Hypertension in an 18-Year-Old girl with Cholesteryl Ester Storage Disease (CESD)," American Journal of Medical Genetrics, 24:711-722(1986).
Carter et al., "Cholesterol Ester Storage Disease," Pediat. Radiol., 2: 135-136 (1974).
Chatrath et al., "Cholesterol ester storage disease (CESD) diagnosed in an asymptomatic adult" Dig. Dis. Sci., 54: 168-173 (2008).
Chatterjee et al., "Evaluation of Urinary Cells in Acid Cholesteryl Ester Hydrolase Deficiency," Clinical Genetics, 29:360-368 (1986).
Chobanian et al., "Effects of Hypertension and of Antihypertensive Therapy on Atherosclerosis," Suppl. I. Hypertension, 8(4):15-21 (1986).
Chowdhury et al., A fourteen year old boy with cholesterol ester storage disease (CESD), American Journal of Medical Genetrics, 24: 711-722 (1986).
Clarke, "Recombinant Proteins from Genetic Disease," Clin. Genet. 55(6): 389-94 (1999), Chris S. Russell.

Coelho et al., "Cholesterylester Storage Disease Report of a case," Arq Gastroenterol, 24(3/4):184-187, (1987).
Dincsoy et al., "Cholesterol Ester Storage Disease and Mesenteric Lipodystrophy," Am. J. Pathol., 81:263-264 (1984).
Christomanou et al., "Prenatal Monitoring for Wolman's Disease in a Pregnancy at Risk," Clinical Case Reports, 57:440-441 (1981).
Coates et al., "Prenatal Diagnosis of Wolman Disease," American Journal of Medcial Genetics, 2:397-407(1978).
Colin et al., "Modification of Pancreatic Lipase Properties by Directed Molecular Evolution," Protein Engineering, Design and Selection, pp. 1-9, (2010) (downloaded from peds.oxfordjournals.org.).
File History dated Sep. 23, 2010 from European Patent Application No. 01906927.7.
Cortner et al., "Genetic Variation of Lysosomal Acid Lipase," Pediatric Research, 10:927-932 (1976).
Cox, "Effect of Lysosomal cholesterol accumulation on lysosomal and vacuolar-atpase activity," submitted of the Faculty of the Graduate school of Vanderbilt University, pp. 1-108 (2007).
Crocker et al., "Wolmans Disease: Three New Patients with a Recently Described Lipidosis," Pediatrics, 35:627-640 (1965).
Cummings et al., Increased Hepatic Secretion of Very-Low-Density Lipoprotein Apolipoprotein B-100 in Cholesteryl Ester Storage Disease, Clinical Chemistry, 41(1): 111-114 (1995).
D'Agostino et al., "Cholesterol Ester Storage Disease: Clinical, Biochemical, and pathological Studies of Four New Cases," Journal of Pediatric Gastroenterology and Nutrition, 7:446-450 (1988).
Dahl et al., "Hepatosplenomegalic Lipidosis: What Unless Gaucher? Adult Cholesteryl Ester Storage Disease (CESD) with Anemia, Mesenteric Lipodystrophy, Increased Plasma Chitotriosidase Activity and a Homozygous Lysosomal Acid Lipase—1 Exon 8 /Splice Junction Mutation," Journal of Hepatology 31:741-746 (1999).
Daly et al., "Neonatal Gene Transfer Leads to Widespread Correction of Pathology in a Murine Model of Lysosomal Storage Disease," Proc. Natl. Acad Sci., 96: 2296-2300 (1999).
Dalgic "Cholestryl ester storage disease in a young child presenting as isolated hepatomegaly treated with simvastatin" The Turkish Journal of Pediatrics, 48: 148-151 (2006).
Davis et al., Role of Acid Lipase in Cholesteryl Ester Accumulation During Atherogenesis; Correlation of Enzyme Activity with Acid Lipase-Containing Macrophages in Rabbit and Human Lesions, Atherosclerosis, 55: 205-215 (1985).
Decarlis et al., "Combined Hyperlipidaemia as a Presenting Sign of Cholesteryl Ester Storage Disease," JIMD Short Report, Online, 3 pages (2009).
De Duve, The Participation of Lysosomes in the Transformation of Smooth Muscle Cells to Foamy Cells in the Aorta of Cholesterol-Fed Rabbits, Lysosomes in Experimental Atheroma, Acta Cardiologica Suppl.: 9-25 (1975).
De Grey et al., Medical Bioremediation: Prospects for the Application of Microbial catabolic diversity to agin and Several Major Age-Related Diseases, Ageing Research Reviews, 4: 315-338 (2005).
Desai et al., "Cholesteryl Ester Storage Disease: Pathologic Changes in an Affected Fetus," American Journal of Medical Genetics, 26:689-698 (1987).
Desnick et al., "Toward Enzyme Therapy for Lysosomal Storage Diseases," Physiological Reviews, 56(1):57-99 (1976).
Di Bisceglie, Cholesteryl Ester Storage Disease: Hepatopathology and Effects of Therapy with Lovastatin, Hepatology, 11(5):764-772 (1990).
Doebber et al., "Enhanced Macrophage Uptake of Synthetically Glycosylated Human Placental B-Glucocerebrosidase," The Journal of Biological Chemistry, 257(5):2193-2199 (1982).
Drebber et al., "Severe Chronic Diarrhea and Weight Loss in Cholesteryl Ester Storage Disease: A Case Report," World Journal Gastroenterol, 11(15):2364-2366 (2005).
Du et al., "Molecular and enzymatic analyses of lysosomal acid lipase in cholesteryl ester storage disease" Mol. Genet. Metab., 64:126-134 (1998).
Du et al., "MRI of Fat Distribution in a Mouse Model of Lysosomal Acid Lipase Deficiency" AJR 184: 658-662 (2005).

(56) References Cited

OTHER PUBLICATIONS

Du et al., "Targeted disruption of the mouse lysosomal acid lipase gene: long-term survival with massive cholesteryl ester and triglyceride storage" Hum. Mol. Genet., 7: 1347-1354 (1998).

Du et al., "The role of mannosylated enzyme and the mannose receptor in enzyme replacement therapy" Am. J. Hum. Genet., 77: 1061-1074 (2005).

Du et al., "Tissue and cellular specific expression of murine lysosomal acid lipase mRNA and protein" Journal of Lipid Research, 37: 937-949 (1996).

Du et al., "Wolman disease/cholesteryl ester storage disease: efficacy of plant-produced human lysosomal acid lipase" J. of Lipid Research, 49: 1646-1657 (2008).

Du et al., "Enzyme Therapy for Lysosomal Acid Lipase Deficiency in the Mouse Model," FASEB J., 10(2):427, Abstract 2409 (1996).

Du et al., "Human Transcription Factor USF Stimulates Transcription through the Initiator Elements of the HIV-1 and the Ad-ML Promoters," The EMBO Journal, 12(2):501-511 (1993).

Du et al., "Lysosomal Acid Lipase and Atherosclerosis," Curr. Opin. Lipidol., 15: 539-544 (2004).

Du et al., Lysosomal acid lipase deficiency: correction of lipid storage by adenovirus-mediated gene transfer in mice, Hum. Gen Ther., 13: 1361-1372 (2002).

Du et al., "Lysosomal Acid Lipase-Deficient Mice: Depletion of White and Brown Fat, Severe Hepatosplenomegaly, and Shortened Life Span," Journal of Lipid Research, 42(4):489-500 (2001).

Du et al., "Mouse Lysosomal Acid Lipase: Characterization of the Gene and Analysis of Promoter Activity," Gene, 208:285-295(1998).

Du et al., "Reduction of Atherosclerotic Plaques by Lysosomal Acid Lipase Supplementation," Journal American. Heart Assoc., Arterioscler Thromb. Vasc. Biol., 24:147-154 (2004).

Du et al.,"Enzyme therapy for lysosomal acid lipase deficiency in the mouse model" Am. J. Hum. Genetics. 67; (4 supp. 2): 427 (2000).

Du et al.,"Enzyme therapy for lysosomal acid lipase deficiency in the mouse model" Hum. Mol. Genet., 10: 1639-1648 (2001).

Dustin et al., "A Mannose 6-Phosphate-Containing N-Linked Glycopeptide Derived from Lysosomal Acid Lipase is Bound to MHC ClassII in B Lymphoblastoid Cell Lines," J. Immunol., 156:1841-1847 (1996).

Drevon et al., "The Effects of Cholesterol/Fat Feeding on Lipid Levels and Morphological Structures in Liver, Kidney and Spleen in Guinea Pigs," Acta path. microbial. scand. Sect. A, 85:1-18 (1977).

Edelstein et al., "Cholesteryl Ester Storage Disease: A Patient with Massive Splenomegaly and Splenic Abscess," The American Journal of Gastroenterology, 83:687-688. (1988).

Elleder et al., "Lysosomal Acid Lipase Deficiency. Overview of Czech Patients," Cas Lek Cesk, 13/(23),719-724 (1999).

Elleder et al., "Subclinical course of cholesterol ester storage disease (CESD) diagnosed in adulthood," Virchows Archiv a Pathological Anatomy and Histopathology, 416:3457-365 (1990).

Elleder et al., "Subclinical course of cholesteryl ester storage disease in an adult with hypercholesterolemia, accelerated atherosclerosis, and liver cancer," Journal of Hepatology, 32:528-534 (2000).

Elleder et al., "Testis—A Novel Storage Site in Human Cholesteryl Ester Storage Disease Autopsy Report of an Adult Case with a Long-Standing Subclinical Course Complicated by Accelerated Atherosclerosis and Liver Carcinoma," Virchows Arch, 436:82-87 (2000).

Ezekowitz et al., "Molecular Characterization of the Human Macrophage Mannose Receptor: Demonstration of Multiple Carbohydrate Recognition-Like Domains and Phagocytosis of Yeasts in Cos-1 Cells," J. Exp. Med., 172:1785-1794 (1990).

Ezekowitz et al., "The Structure and Function of Vertebrate Mannose Lectin-Like Proteins," J. Cell. Sci. Suppl., 9:121-133 (1988).

Fadden et al., "Molecular Characterization of the Rat Kupffer Cell Glycoprotein Receptor," Glycobiology, 13(7):529-537 (2003).

Ferry et al., "Liver Transplantation for Cholesteryl Ester Storage Disease," Journal of Pediatric Gastroenterology and Nutrition, 12:376-378 (1991).

Fiete et al., "The macrophage/endothelial cell mannose receptor cDNA encodes a protein that binds oligosaccharides terminating with S04-4-GalNAc,3 l,4GlcNAcf3 or Man at independent sites," Proc. Natl. Acad. Sci., 94:11256-11261 (1997).

File History dated Sep. 23, 2010 from European Patent Application No. 01906927.7-2107/1267914.

Fitoussi et al., "New Pathogenetic Hypothesis for Wolman Disease: Possible Role of Oxidized Low-Density Lipoproteins in Adrenal Necrosis and Calcification," Biochem, J., 301:267-273 (1994).

Fitzky et al., "7-Dehydrocholesterol-Dependent Proteolysis of HMG-CoA Reductase Suppresses Sterol Biosynthesis in a Mouse Model of Smith-Lemli-Opitz/RSH Syndrome," The Journal of Clinical Investigation, 108(6):905-915 (2001).

Foger et al., "Unusual Presentation of Cholesterol Ester Storage Disease (CESD): Report on New Family," Atherosclerosis, 109:132 Abstract 155 (1994).

Folch et al., "A Simple Method for the Isolation and Purification of Total Lipide from Animal Tissues," J. Bio. Chem, 226:497-509 (1957).

Friedman et al., "A Comparison of the Pharmacological Properties of Carbohydrate Remodeled Recombinant and Placental-Derived b-Glucocerebrosidase: Implications for Clinical Efficacy in Treatement of Gaucher Disease," Blood, 93(9):2807-2816 (1999).

Fujiyama et al., "A New Mutation (LIPA Tyr22X) of Lysosomal Acid Lipase Gene in a Japanese Patient with Wolman Disease," Human Mutation, 8:377-380 (1996).

Fulcher et al., "Pediatric Case of the Day", RadioGraphics, 18( 2):533-534 (1988).

Furbish et al., "Uptake and Distribution of Placental Glucocerebrosidase in Rat Hepatic Cells and Effects of Sequential Deglycosylation," Biochimica et Biophysica Acta, 673 425-434, 1981.

Gasche et al., "A Novel Variant of Lysosomal Acid Lipase in Cholesteryl Ester Storage Disease Associated with Mild Phenotype and Improvement on Lovastatin," Journal of Hepatology, 27:744-750 (1997).

Gerlai et al., "Gene-Targeting Studies of Mammalian Behavior: Is it the Mutation or the Background Genotype," Trends Neurosci, 19:177-181 (1996).

Gidiri et al., Letter to the Editor, European Journal of Obstetrics and Gynecology and Reproductive Biology, 142:81-87 (2009).

Ginsberg et al., Suppression of Apolipoprotein B Production during Treatment of Cholesteryl Ester Storage Disease with Lovastatin, J. Clin. Invest., 80:1692-1697 (1987).

Glueck et al., "Safety and Efficacy of Treatment of Pediatric Cholesteryl Ester Storage Disease with Lovastatin," Pediatric Research, 32:559-565 (1992).

Goldstein et al., "Role of Lysosomal Acid Lipase in the Metabolism of Plasma Low Density Lipoprotein," The Journal of Biological Chemistry, 250(21):8487-8795, (1975).

Grabowski et al., "Enzyme supplementation for treatment of artherosclerosis using lysosomal acid lipase" Therapy for Genetic Disorders, The American Journal of Human Genetics,67(4) (Suppl. 2) (Abstract No. 136) (2000).

Grabowski et al., "Enzyme Therapy for Lysosomal Storage Disease: Principles, Practice and Prospects," Annu. Rev. Genomics Hum. Genet., 4:403-436 (2003).

Groener et al., "Difference in Substrate Specificity Between Human and Mouse Lysosomal Acid Lipase: Low Affinity for cholesteryl Ester in Mouse Lysosomal Acid Lipase," Biochimica et Biophysica Acta, 1487:155-162 (2000).

Guazzi et al., "Wolman's Disease. Distribution and Significance of the Central Nervous System lesions," Path. Europ., 3:266-277 (1968).

Gunning et al., "Isolation and Characterization of Full-Length cDNA Clones for Human a-, 13-, and y-Actin mRNAs: Skeletal but Not Cyoplasmic Actins Have an Amino-Terminal Cysteine that is Subsequently Removed," Molecular and Cellular Biology, 3(5):787-795 (1983).

Guzzetta et al., "Elective Subtotal Splenectomy," Ann. Surg., 211 (1): 34-42 (1990).

Hafner et al., "The Human Primary Hepatocyte Transcriptome Reveals Novel Insights into Atorvastatin and Rosuvastatin Action," Pharmacogenetics and Genomics, 21(11):741-750 (2011).

(56) References Cited

OTHER PUBLICATIONS

Hakala et al., "Lysosomal Enzymes are Released from cultured Human macrophages, Hydrolyze LDL in Vitro, and are Present Extracellularly in Human Atherosclerotic Lesions," Arteriosclerosis, Thrombosis, and Vascular Biology, 23:1430-1436, (2003).
Haller et al., "Gallbladder Dysfunction in Cholesterol Ester Storage Disease," JPGN, 50(5):556-557 (2010).
Hatanaka et al., "Human IgA-Binding Peptides Selected from Random Peptide Libraries: Affinity Maturation and Application in IgA Purification," J. Bio. Chem. In Press, M112 389742, pp. 1-12 (2012).
Hill et al., "CT Findings in Acid Lipase Deficiency: Wolman Disease and Cholesteryl Ester Storage Disease," Journal of Computer Assisted Tomography, 7(5):815-818 (1983).
Hoeg et al., "Characterization of Neutral and Acid Ester Hydrolase in Wolman's Disease," Biochimica et Biophysica Acta, 711:59-65 (1982).
Hoeg et al., "Cholesteryl Ester Storage Disease and Wolman Disease: Phenotypic Variants of Lysosomal Acid Cholesteryl Ester Hydrolase Deficiency," Am. J. Hum. Genet, 36:1190-1203 (1984).
Holbrook et al., "Tolerization as a Too for Generating Novel Monoclonal Antibodies," Immunology and Cell Biology, 80:319-322 (2002).
Hollak et al., "Alglucerase Practical Guidance on Appropriate Dosage and Administration in Patients with Gaucher Disease," Blodrugs, 9(1):11-23 (1998).
Hooper et al., "A Novel Missense LIPA Gene Mutation, N98S, in a Patient with Cholesteryl Ester Storage Disease," Clinica Chimica Acta, 398:152-154 (2008).
Hopkins et al., "Human Genetics and Coronary Heart Perspective," Annu. Rev. Nutr., 9:303-45 (1989).
Hua et al., "SREBP-2, A Second Basic-Helix-Leucine Zipper Protein that Stimulates Transcription by Binding to a Sterol Regulatory Element," Proc. Natl. Acad. Sci., 90:11603-11607 (1993).
Ikeda et al., "Production of Recombinant Human Lysosomal Acid Lipase in *Schizosaccharomyces pombe*: Development of a Fed-Batch Fermentation and Purification Process" J. of Bioscience and Bioengineering, 98:366-373 (2004).
Heinz et al., "Identification and in Situ Localization of the Insulin-Like Growth Factor- II/Mannose-6-Phosphate (IGF-II/M6P) Receptor in the Rat Gastrointestinal Tract: Comparison with the IGF-1 Receptor," Endolcrinology, 129(4):1769-1778 (1991). (Abstract only).
Imanaka et al., "Characterization of Lysosomal Acid Lipase Purified from Rabbit Liver," J. Biochem., 96: 1089-1101 (1984).
International Search Report for PCT/US2011 /051096, mailed Feb. 2, 2012.
Ishibashi et al., "Hypercholesterolemia in Low Density Lipoprotein Receptor Knockout Mice and its Reversal by Adenovirus-Mediated Gene Delivery," J. Clin. Invest., 92:883-893 (1993).
Iverson et al., "Asymptomatic cholesteryl ester storage disease in an adult controlled with simvastatin," Ann Clin Biochem, 34:433-436 (1997).
Jeschke et al., "Cholesteryl Ester Storage Disease, Clinical and Morphological Aspects," Cholesterylester-Speicherkrankheit, 120(8):601-604 (1982).
Jeyakumar et al., "Storage Solutions: Treating Lysosomal Disorders of the Brain," Nature Reviews Neuroscience, 6:713-725 (2005).
Jirtle et al., "Modulation of Insulin-Like Growth Factor-II/Mannose 6-Phosphate Receptors and Transforming Growth Factor-β1 during Liver Regeneration," The Journal of Biological Chemistry, 266(33):22444-22450 (1991).
Jolly et al., "Lysosomal Storage Diseases of Animals: an Essay in Comparative Pathology," Vet Pathol., 34:527-548 (1997).
Justus et al., "Lebermorphologie and Klinik eins Falls von Cholesterinester-Speicherkrankheit," Dtsch. Z. Verdau-Stoffwechs. krankh. 48:198-207 (1988).
Kahana et al., "Primary Familial Xanthomatosis with Adrenal Involvement (Wolman's Disease); Report of a further Case with Nervous System Involvement and pathogenetic Considerations," Pediatrics, 42(1):71-76 (1968).

Kale et al., "End Stage Renal Disease in a Patient with Cholesteryl Ester Storage disease Following Successful Liver Transplantation and Cyclosporine Immunosuppression," Journal of Pediatric Gastroenterology and Nutrition, 20:95-97 (1995).
Kawashiri et al., "Gene Therapy for Lipid Disorders," Curr. Control Trials Cardiovascular Med., 1:120-127 (2000).
Kelly et al., "Characterization of Plasma Lipids and Lipoproteins in Cholesteryl Ester Storage Disease," Biochemical Medicine, 33:29-37 (1985).
Kikuchi et al., "Evaluation of Jejunal Function in Wolman's Disease," Journal of Pediatric Gastroenterology and Nutrition, 12(1): 6569 (1991).
Kim, Successful Management of Difficult Infusion-Associated Reactions in a Young Patient with Mucopolysaccharidosis Type VI Receiving Recombinant Human Arylsulfatase B (Galsulfase [Naglazyme]) Pediatrics 121(3): 714-717 (2008).
Klima et al., "A Splice Junction Mutation Causes Deletion of a 72-Base Exon from the mRNA for Lysosomal Acid Lipase in a Patient with Cholesteryl Ester Storage Disease," J. Clin. Invest., 92:2713-2718 (1993).
Koch et al., "Assignment of LIPA, Associated with Human Acid Lipase Deficiency, to Human Chromosome 10 and Comparative Assignment to Mouse Chromosome 19," Somatic Cell Genetics, 7(3):345-358 (1981).
von Kodolitsch et al., "Splice-Site Mutations in Atherosclerosis Candidate Genes Relating Individual Information to Phenotype," Circulation, 100:693-699 (1999).
Kolodny et al., "Current Concepts in Genetics; Lysosomal Storage Disease," The New England Journal of Medicine, 294(22):1217-1220 (1976).
Kostner et al., "Plasma Lipids and Lipoproteins of a Patient with Cholesteryl Ester Storage Disease," J. Inher. Metab. Dis. 8:9-12 (1985).
Kowal et al. "Low Density Lipoprotein Receptor-Related Protein Mediated Uptake of Cholesteryl Esters Derived from apoprotein E-Enriched Lipoproteins," Proc. Natl. Acad. Sci., 86:5810-5814 (1989).
Krivit et al., "Wolman's Disease: a Review of Treatment with Bone Marrow Transplantation and Consideration for the Future" Bone Marrow Transplantation, 10 (Suppl 1): 97-101 (1992).
Krivit et al., "Wolman Disease Successfully Treated by Bone Marrow Transplantation," Bone Marrow Transplantation, 26:567-570 (2000).
Kiinnert et al., "Cholesteryl ester storage disease and sea-blue histiocytes," Zentralbl. Allg. Pathol. Pathol. Anat. 133:517-525 (1987).
Klinnert et al., "Zur Diagnostik and Morphologie der Leber bei Cholesterolester-Speicher-krankheit," Zbl. Allg. Pathol. a. pathol. Anat. 123:71-84 (1979).
Kuntz et al., "Cholesterinester-Speicherkrankheit der Leber," Leber Magen Darm 11, Nr. 6:258-263 (1981).
Kuriwaki et al., Morphological Characteristics of Lipid Accumulation in Liver-Constituting Cells of Acid Lipase Deficiency Rats (Wolman's Disease Model Rats), Pathology International, 49:291-297 (1999).
Kuriyama et al., "Lysosomal acid lipase deficiency in rats: lipid analyses and lipase activites in liver and spleen" J. of Lipid Research, 31:1605-1612 (1990).
Kyriakides et al., "Lipid accumulations and acid lipase deficiency in fibroblasts from a family with Wolman's disease and their apparent correction in vitro" J. of Lab. Clin. Med., 80:810-816 (1972).
Laird et al., "Simplified Mammalian DNA Isolation Procedure," Nucleic Acids Research, 19(15):4293 (1991).
Lake et al., "Histochemical Detection of the Enzyme Deficiency in Blood Films in Wolman's Disease," J. Clin. Path., 24:617-620 (1971).
Lake et al., "Wolman's Disease Deficiency of E600-Resistant Acid Esterase Activity with Storage of Lipids in Lysosomes," The Journal of Pediatrics, 76(2):262-266 (1970).
Lashford et al., "Lysosomal Storage Disorders," Gene Therapy Technologies, Applications and Regulations, John Wiley & Sons, Chichester, UK (1999).

(56) References Cited

OTHER PUBLICATIONS

Lee et al., "Intragenic Deletion as a Novel Type of Mutation in Wolman Disease," Molecular Genetics and Metabolism, 104:703-705 (2011).
Lee et al., "Mannose Receptor-Mediated Regulation of Serum Glycoprotein Homeostasis," Science, 295:1898-1901 (2002).
Leone et al., "Treatment and liver transplantation for cholesterol ester storage disease," The Journal of Pediatrics, 127(3):509-510 (1995).
Leone et al., "Use of simvastatin plus cholestyramine in the treatment of lysosomal acid lipase deficiency," The Journal of Pediatrics, 119(6):1008-1009 (1991).
Leonova et al., "Proteolytic Processing Patterns of prosaposin in Insect and Mammalian Cells," The Journal of Biological Chemistry, 271(29):17312-17320 (1996).
Leslie et al., "A Mouse Model of Galactose-1-Phosphate Uridyl Transferase Deficiency," Biochemical and Molecular Medicine, 59:7-12 (1996).
Levy et al., "Cholesteryl Ester Storage Disease: Complex Molecular Effects of Chronic Lovastatin Therapy," Journal of Lipid Research, 33:1005-1015 (1992).
Lew et al., "A Mannose Receptor Mediates Mannosyl-Rich glycoprotein-Induced Mitogenesis in Bovine Airway Smooth Muscle Cells," J. Clin. Invest., 94:1855-1863 (1994).
Li et al., "Gsh-1, An Orphan Hox Gene, is Required for Normal pituitary Development," The EMBO Journal, 15(4):714-724 (1996).
Lian et al., "Lysosomal acid lipase deficiency causes respiratory inflammation and destruction in the lun J" Am. J. Physio. LunQ Cell Mol. Physiol., 286:L801-L807 (2004).
Liu et al., "Phenotypic Correction of Feline Lipoprotein Lipase Deficiency by Adenoviral Gene Transfer," Human Gene Therapy, 11:21-32 (2000).
Lohse et al., "Compound Heterozygosity for a Wolman Mutation is Frequent Among Patients with Cholesteryl Ester Storage Disease," Journal of Lipid Research, 41:23-31 (2000).
Lohse et al., "Human Lysosomal Acid Lipase/Cholesteryl Ester Hydrolase and Human Gastric Lipase: Identification of the Catalytically Active Serine, Aspartic Acid, and Histidine Residues," Journal of Lipid Research, 38:892-903 (1997).
Lohse et al., "Human Lysosomal Acid Lipase/Cholesteryl Ester Hydrolase and Human Gastric Lipase:Site-Directed Mutagenesis of Cys227 and Cys236 Results in Substrate-Dependent Reduction of Enzymatic Activity," Journal of Lipid Research,38:1896-1905 (1997).
Lohse et al., "Molecular Defects Underlying Wolman Disease Appear to be More Heterogeneous than those Resulting in Cholesteryl Ester Storage Disease," Journal of Lipid Research, 40:221-228 (1999).
Lohse et al., "The Acid Lipase Gene Family: Three Enzymes, One Highly Conserved Gene Structure," Journal of Lipid Research, 38:881-891 (1997).
Longhi et al., "Cholesteryl Ester Storage Disease: Risk Factors for Atherosclerosis in a 15-Year-Old Boy," J. Inher. Metab. Dis., 11(2):143-145 (1988).
Lough et al., "Wolman's Disease: An Electron Microscope, Histochemical, and Biochemical Study," Arch. Path, 89:103-110 (1970).
Lowden et al., "Wolman's Disease: A Microscopic and Biochemical Study Showing Accumulation of Ceroid and Esterified Cholesterol," C.M.A. Journal, 102:402-405 (1970).
Lübke et al., "Proteomics of the Lysosome," Biochim Biophys Acta, 1793(4):625-635 (2009).
Mao et al., "Sortase-Mediated Protein Ligation: A New Method of Protein Engineering," J. Am. Chem. Soc. 126, 2670-2671, 2004.
Marsh et al., "Apolipoprotein B Metabolism in Humans: Studies with Stable Isotope-Labeled Amino Acid Precursors," Atherosclerosis, 162:227-244 (2002).
Marshall et al., "Wolman's Disease: A Rare Lipidosis with Adrenal Calcification," Arch. Dis. Childhood, 44:331-341 (1969).
Martinez et al., "7 Years Experience with Hepatic Transplantation in Children," Cir. Pediatr. 6(1):7-10 (1993).
Maslen et al., "Occurrence of a mutation associated with Wolman disease in a family with cholesteryl ester storage disease," J. Inher. Metab. Dis., 18:620-623 (1995).
Mayatepek et al., "Fatal genetic defect causing Wolman Disease," J. Inher. Metab. Dis., 22:93-94 (1999).
McPhee et al., "Effects of AAV-2 mediated aspartoacylase gene transfer in the tremor rat model of Canavan disease," Molecular Brain Research, 135:112-121 (2005).
Meikle et al., "Prevalence of Lysosomal Storage Disorders," JAMA, 281(3):249-254 (1999).
Melling et al., "Localised massive tumourous xanthomatosis of the small intestine," Int. J. Colorectal Dis., 22:1401-1404 (2007).
Meyers et a, The use of parenteral hyperalimentation and elemental formula feeding in the treatment of Wolman Disease, Nutrition Research 5(4): 423-442 (1985).
Michels et al., "Cholesteryl Lignocerate Hydrolysis in Adrenoleukodystrophy," Pediat. Res. 14:21-23 (1980).
Michels et al., "Pulmonary vascular obstruction associated with cholesteryl ester storage disease," The Journal of Pediatrics, 94:621-622 (1979).
Mistry et al., "Therapeutic delivery of proteins to macrophages: implications for treatment of Gaucher's disease," The Lancet, 348:1555-1556 (1996).
Mori et al., "Identification of the Mannan-Binding Protein from Rat Livers as a Hepatocyte Protein Distinct from the Mannan Receptor on Sinusoidal Cells," Archives of Biochemistry and Biophysics, 222(2):542-552 (1983).
Muntoni et al., "A missense mutation (Thr-6Pro) in the lysosomal acid lipase (LAL) gene is present with a high frequency in three different ethnic populations: impact on serum lipoprotein concentrations," Hum Genet, 97:265-267 (1996).
Muntoni et al., "Homozygosity for a splice junction mutation in exon 8 of the gene encoding lysosomal acid lipase in a Spanish kindred with cholesterol ester disease (CESD)," Hum Genet, 95:491-494 (1995).
Muntoni et al., "Prevalence of Cholesteryl Ester Storage Disease," Arterioscler. Thomb. Vasc. Biol., 27:1866-1868 (2007).
Nakagawa et al., "Cloning of rat lysosomal acid lipase cDNA and identification of the mutation in the rat model of Wolman's disease," J. Lipra Res 36:2212-2213 (1995).
Nègre et al., "Acid Lipases and Acid Cholesterol Esterases: Wolman's Disease and Cholesteryl Ester Storage Disease," Path Biol., 36(2): 167-181 (1988).
Negre-Salvayre et al., "UV-treated lipoproteins J. Lipid Res. as a model system for the study of the biological effects of lipid peroxides on cultured cells. 4. Calcium is involved in the cytotoxicity of UV-treated LDL on lymphoid cell lines," Biochimica et Biophysica Acta, 1123:1207-215 (1992).
Nobili et al., "Treatment of nonalcoholic fatty liver disease in adults and children: a closer look at the arsenal," J Gastroenterol, (2011). DOI 10.1007/s00535-011-0467.
Noorman et al., "The mannose receptor, localization and role in the clearance of tissue-type plasminogen activator," Fibrinolysis & Proteolysis, 12(4):241-250 (1998).
Odievre, "Clinical presentation of Metabolic Liver Disease," J. Inher. Metab. Dis., 14:526-530 (1991).
Office Action issued from the U.S. Patent and Trademark Office, mailed Jan. 18, 2013, in U.S. Appl. No. 13/229,558, 12 pages.
Opposition against European Patent 1267914, dated Jan. 28, 2010.
Özmen et al., "Wolman's disease: ultrasonographic and computed tomographic findings," Pediatr Radiol, 22:541-542 (1992).
Pagani et al., "A histidine to tyrosine replacement in lysosomal acid lipase causes cholesteryl ester storage disease," Human Molecular Genetics, 3(9): 1605-1609 (1994).
Pagani et al., "Expression of lysosomal acid lipase mutants detected in three patients with cholesteryl ester storage disease," Human Molecular Genetics, 5(10):1611-1617 (1996).
Pagani et al., New lysosomal acid lipase gene mutants explain the phynotype of Wolman disease and cholestery ester storage disease, Journal of Lipid Research 39: 1382-1388 (1988).
Pagani et. al, "Cysteine residues in human lysosomal acid lipase are involved in selective cholesteryl esterase activity," Biochem J. 326:265-269 (1997).

(56) References Cited

OTHER PUBLICATIONS

Pariyarath et al., L273S missense substitution in human lysosomal acid lipase creates a new N-glycosylation site, FEBS Letter, 379: 79-82 (1996).
Pastores et al., Enzyme therapy for the lysosomal storage disorders: principles, patents, practice and prospects, Expert Opin. Therapeutic Patients 13(8): 1157-1172 (2003).
Patrick et al., "Deficiency of an Acid Lipase in Wolman's Disease," Nature, 222:1067-1068 (1969).
Pentchev et al., "Incorporation of Exogenous Enzymes into Lysosomes: A Theoretical and Practical Means for Correcting Lysosomal Blockage," American Chemical Society, 150-151 (1978).
Pfeifer et al., "Cholesteryl Ester Storage Disease: Report on Four Cases," Virchows Arch. B. Cel Path. 33:17-34 (1980).
Phillipps et al., "Secretion of insulin-like growth factor-II into bile of rats of different ages," Biol Neonate, 78(2):106-12 (2000).
Pisciotta et al., "Cholesteryl Ester Storage Disease (CESD) due to novel mutations in the *LIPA* gene," Molecular Genetics and Metabolism, 79:143-148 (2009).
Poupětová et al., "LSDS with Neurologic Involvement: The birth prevalence of lysosomal storage disorders in the Czech Republic: comparison with data in different populations," J. Inherit Metab Dis, 33:387-396 (2010).
Pozanasky et al., Enzyme replacement therapy in fibroblast from a patient with cholesteryl ester storage disease, FASEB J., 3: 152-156 (1989).
Rader et al., "Expression of Adenoviral vector Containing the cDNA for Human Lysosomal Acid Lipase in HELA and Wolman Cells" FASEB J, 10(3): Abstract No. 1341 (Annual Meeting of Professional Research Scientists (1996).
Rader, et al, Gene therapy for dyslipidemia: Clinical prospects, Cur. Atherosc, Rep. 1: 58-69 (1999).
Raivio et al., "Genetic Diseases of Metabolism," Annu. Rev. Biochem 41:543-576 (1972).
Rassoul et al., "Long-term administration of the HMG-CoA reductase inhibitor lovastatin in two patients with cholesteryl ester storage disease," International Journal of Clinic Pharmacology and Therapeutics, vol. 39, No. 5:199-204 (2001).
Redonnet-Vernhet et al., "Cholesteryl Ester Storage Disease: Relationship between Molecular Defects and in Situ Activity of Lysosomal Acid Lipase," Biochemical and Molecular Medicine, 62:42-49 (1997).
Ries et al., "A new mutation in the gene for lysosomal acid lipase leads to Wolman disease in an African kindred," Journal of Lipid Research, 37:1761-1762 (1996).
Ries et al., "Different Missense Mutations in Histidine-108 of Lysosomal Acid Lipase Cause Cholesteryl Ester Storage Diseases in Unrelated Compound Heterozygous and Hemizygous Individuals," Human Mutation, 12:44-51 (1998).
Ries et al., "Transcriptional regulation of lysosomal acid lipase in differentiating monocytes is mediated by transcription factors Sp1 and AP-2," Journal of Lipid Research, 39:2125-2126 (1998).
Riva et al., "Hepatocarcinoma in a child with cholesterol ester storage disease," Digestive and Liver Disease, 40:784 (2008).
Rosenbaum et al., "Thiadiazole Carbamates: Potent Inhibitors of Lysosomal Acid Lipase and Potential Neimann-Pick Type C Disease Therapeutics," J Med Chem., 53(14):5281-5289 (2010).
Rosenthal, "Nonalcoholic Fatty Liver Disease in Pediatric Patients—A Problem that is 'Enormous' and 'Growing,'" JPEN J Parenter Enteral Nutr 36:7S (2012).
Rothe et al., "Altered mononuclear phagocyte differentiation associated with genetic defects of the lysosomal acid lipase," Atherosclerosis, 130:215-221 (1997).
Roussel et al., "Crystal Structure of Human Gastric Lipase and Model of Lysosomal Acid Lipase, Two Lipolytic Enzymes of Medical Interest," The Journal of Biological Chemistry, 274( 24):16995-17002 (1999).
Röyttä, et al., "Wolman disease: morphological, clinical and genetic studies on the first Scandinavian cases," Clin Genet, 42:1-7 (1992).
Russell et al., "Recombinant proteins for genetic disease," Clin. Gent., 55: 389-394 (1999).
Salvayre et al., "Maladie de Wolman et of curie cholestérolique de l'adulte (cholesteryl ester storage disease): Nuoveaux moyens d'étude et de diagnostic," Ann. Biol. Clin. 44:611-617 (1986).
Salvayre et al., "Lipases et Cholesterol Esterases Acides: Maladie De Wolman et Cholesteryl Ester Storage Disease (Polycorie Cholesterolique de L'Adulte)" Path Biol, 36, 167-181 (1988).
Salvetti et al., "Gene therapy of lysosomal storage disorders," British Medical Bulletin, 51(1):106-122 (1995).
Sando et al. Human lysosomal acid lipasecholesterly ester hydrolase, Purificationand properties of the form secreted by fibroblasts in microcarrier culture, Journal of Biological Chemstry 260: 15186-15193 (1985).
Sando et al., "Intercellular Transport of lysosomal acid lipase mediates lipoprotein cholesteryl ester metabolism in a human vascular endothelial cell-fibroblast coculture system," Cell Regulation, 1:661-674 (1990).
Sando et al., Recognition and receptor-mediated endocytosis of the lysosomal acid lipase secreted by cultured human fibroblasts, journal of Lipid research 23: 114-123 (1982).
Sanyal et al., "Endpoints and Clinical Trial Design for Nonalcoholic Steatohepatitis," Hepatology, 54(1):344-345 (2011).
Schaub et al., "Wolman's Disease: Clinical, Biochemical and Ultrastructural in an Unusual Case Without Striking Adrenal Calcification" Eur. J. Ped., 135:45-53 (1980).
Schiff et al., "Hepatic Cholesterol Ester Storage Disease, A Familial Disorder," American Journal of Medicine, 44:538-546 (1968).
Schiffmann, "Infusion of α-Galactosidase a Reduces Tissue Globotriaosylceramide Storage in Patients with Fabry Disease," PNAS, 97(1):365-370 (2000).
Scriver et al., "The Metabolic and Molecular Bases of Inherited Disease," $7^{th}$ Ed. V II, McGraw-Hill, New York, pp. 2563-2587 (1995).
Seedorf et al., "A Novel Variant of Lysosomal Acid Lipase ($Lue_{336} \rightarrow Pro$) Associated With Acid Lipase Deficiency and Cholesterol Ester Storage Disease," Arteriosclerosis, Thrombosis, and Vascular Biology, 15:773-778 (1995).
Sheriff et al., Characterization of Lysosomal Acid Lipase by Site-Directed Mutagenesis and Heterologous Expression., J. Biol. Chem., 270:27766-27772 (1995).
Shimada et al., "Suppression of diet-induced atherosclerosis in low density lipoprotein receptor knockout mice overexpressing lipoprotein lipase," Proc. Natl. Acad. Sci. USA, 93:7242-7246 (1996).
Shome et al., "The Middle-East Connection of Wolman Disease," Saudi. Med. J., 23(5): 597-601 (2002).
Skinner et al., "Cholesterol Curves to Identify Norms by Age and Sex in Healthy Weight Children," Clin Pediatr, 51:233 (2012).
Sloan et al., "Enzyme Deficiency in Cholesteryl Ester Storage Disease," the Journal of Clinical Investigation, 51:1923-1924 (1972).
Sly et al., "Enzyme therapy in mannose receptor-null mucopolysaccharidosis VII mice defines roles for the mannose 6-phosphate and mannose receptors," PNAS, 103(41):15172-15177 (2006).
Smith et al., "Peptide Sequences Mediating Tropism to Intact Blood-Brain Barrier: An In Vivo Biodistribution Study Using Phage Display," Peptides, 38:172-180 (2012).
Spiegel-Adolf et al., "Hematologic Studies in Niemann-Pick and Wolman's Disease," Confin. Neurol, 28:399-406 (1966).
Stahl et al., "Evidence for receptor-mediated binding of glycoproteins, glycoconjugates, and lysosomal gylcosidases by alveolar macrophages," Cell Biology, 75(3):1399-1403 (1978).
Stein, et. al. "Successful Treatment of Wolman Disease by Unrelated Umbilical Cord Blood Transplantation" Europ. J. Pediatrics 166(7): 663-666 (2007).
Sternby et al., "Carboxyl Ester Lipase (Bile Salt-Stimulated Lipase), Colipase, Lipase, and Phospholipase $A_2$ Levels in Pancreatic Enzyme Supplements," Scand J Gastroenterol 32:261-267 (1997).
Surve et al., "Wolman Disease: Diagnosis by Leucocyte Acid Lipase Estimation," Indian Journal of Pediatrics, 72: 353-354 (2005).
Suzuki et al., "Are animal models useful for understanding the pathophysiology of lysosomal storage disease?" Acta Paediatr. Suppl., 443: 54-62 (2003).

(56) References Cited

OTHER PUBLICATIONS

*Synageva Biopharma Corp.* v. *Childrens' Hospital Research Foundation*, "Grounds of Invalidity of European Patent 1267914," pp. 1-11, UK High Court of Justice, Chancery Division, Patent Court, Jan. 16, 2012.
*Synageva Biopharma Corp., and Synageva Biopharma Limited*, plaintiffs v. *Children's Hospital Research Foundation, Children's Hospital Foundation*, Cincinnati, Ohio and Children's Hospital Medical Center, defendants, Tribunal de Grande Instance of Paris, Mar. 26, 2013, "Pleadings No. 1".
*Synageva Biopharma Limited*, claimant v. *Children's Hospital Research Foundation*, defendant, in the High Court of Justice, Chancery division, Patents Court, Claim No. HC 12 C00211, "Statement of Opposition" (2013).
*Synageva Biopharma Limited*, claimant v. *Children's Hospital Research Foundation*, defendant, In the High Court of Justice, Chancery division, Patents Court, Claim No. HC 12 C00211, "Grounds of Invalidity" (2012).
*Synageva Biopharma Limited*, claimant v. *Children's Hospital Research Foundation*, defendant, in the High Court of Justice, Chancery division, Patents Court, Claim No. HC 12 C00211, "Amended Grounds of Invalidity" (2013).
Tadiboyina "Treatment of dyslipidemia with lovastatin and ezetimibe in an adolescent with cholestryl ester storage disease" Lipids in Health and Disease, 4(26): 1-6 (2005).
Takahashi et al., "Distribution of murine mannose receptor expression from early embryogenesis through to adulthood," Cell Tissue Res 292:311-323 (1998).
Takasak,i et al., "Structure of the *N*-Asparagine-linked Oligosaccharide Units of Human Placental β-Glucocerebrosidase," The Journal of Biological Chemistry, 259(16):10112-10117 (1984).
Tanaka et al., Acid Lipase Deficiency: Wolman Disease and Cholesteryl Ester Storage Disease, Nippon Rinsho, 53(12): 3004-3008 (1995).
Tarantino et al., "Lovastatin therapy for cholesterol ester storage disease in two sisters," The Journal of Ped., 118(1):131-135 (1991).
Thompson et al., "Role of cholesterol in regulating apolipoprotein B secretion by the liver," Journal of Lipid Research, 37:439-440 (1996).
Tolar et al., "Long-term metabolic, endocrine, and neuropsychological outcome of hematopoietic cell transplantation for Wolman disease," Bone Marrow Transplantation, 43:21-27 (2009).
Todoroki et al., "Accumulated lipids, aberrant fatty acid composition and defective cholesterol ester hydrolase activity in cholesterol ester storage disease," Ann Clin Biochem, 37:187-193 (2000).
Thavarungkul et al., Cholesterol Ester Storage disease: A Reported Case., J. Med. Assoc. Thai, 78(3): 164-168 (1995) (Abstract Only).
Tylki-Szymańska, et al, "Clinical, biochemical and histological analysis of seven patients with cholesteryl ester storage disease," Acta Paediatrica Japonica, 39:643-646 (1997).
Uniyal et al., "Wolman's Disease," Indian Pediatrics, 32:232-233 (1995).
Van Berkel, "The role of non-parenchymal cells in liver metabolism," TIBS 202-205, Sep. 1979.
Van Erum et al., "Cholesteryl Ester Storage Disease with Secondary Lecithin Cholesterol Acyl Transferase Deficiency," J. Inher. Metab. Dis 11 Suppl. 2:146-148 (1988).
Varki et al., "Studies of synthesis, structure and function of the phosphorylated oligosaccharides of lysosomal enzymes," J. Biosci, 5(1):101-104 (1983).
vom Dahl et al., "Lysosomal storage disease as differential diagnosis of hepatosplenomegaly," Best Practice & Research Clinical Gastroenterology, 24:619-628 (2010).
von Figura et al., "Lysosomal Enzymes and Their Receptors," Ann. Rev. Biochem, 55:167-193 (1986).
Von Trotha et al., "Influence of Lysosomal Acid Lipase Polymorphisms on Chromosome 10 on the Risk of Alzheimer's Disease and Cholesterol Metabolism," Neuroscience Letters, 402:(3):262-266 (2006) [Abstract Only].
Vuillemenot et al., "Intrathecal tripeptidyl-peptidase 1 reduces ysosomal storage in a canine model of late infantile neuronal ceroid lipofuscinosis," Molecular Genetics and Metabolism, 104:325-337 (2011).
Walters et al., "Cholesterol esterase activities in commercial pancreatic enzyme preparations and implications for use in pancreatic insufficient cystic fibrosis," Journal of Clinical Pharmacy and Therapeutics, 26:425-431 (2001).
Wang et al., "SREBP-1, a Membrane-bound Transcription Factor Released by Sterol-Regulated Proteolysis," Cell, 77:53-62 (1994).
Warner et al., "Purification of the Lysosomal Acid Lipase from Human Liver and Its Role in Lysosomal Lipid Hydorlysis," The Journal of Biological Chemistry, 246(6):2952-2957 (1981).
Warner et al., "Separation and Characterization of the Acid Lipase and Neutral Esterases from Human Liver," Am. J. Hum Genet, 32:869-879 (1980).
Wolman et al., "Wolman Disease and Its Treatment" Clin. Pediatr. 34(4):207-212 (1995).
Wolman, "Involvement of Nervous Tissue in Primary Familial Xanthosmatosis with Adrenal Calcification," Path Europe, 3:259-265 (1968).
Wolman, "Primary Familial Xanthomatosis with Involvement and Calcification of the Adrenals: Report of Two or More Cases in Siblings of a Previously Described Infant," Pediatrics, 28:742-757 (1961).
Wolman, "Proposed Treatment for Infants With Wolman Disease," Pediatrics, 83:1074-1075 (1989).
Written Opinion dated Nov. 5, 2001 from PCT Application No. PCT/US01/03481.
Xu et al., "Turnover and Distribution of Intravenously Administered Mannose-Terminated Human Acid [beta]-Glucosidase in Murine and Human Tissues," Pediatric Research, 39(2):313-322 (1996).
Yagyu et al., "Overexpressed lipoprotein lipase protects against atherosclerosis in apolipoprotein E knockout mice," Journal of Lipid research, 40:1677:1678 (1999).
Yan et al., "Macrophage-Specific Expression of Human Lysosomal Acid Lipase Corrects Inflammation and Pathogenic Phenotypes in $lal^{-/-}$Mice," The American Journal of Pathology, 169(3):916-917 (2006).
Yokoyama et al., "Long-term treatment of a homozygous cholesteryl ester storage disease with combined cholestryamine and lovastatin," J. Inher. Metab. Dis. 15:219-292 (1992).
Yoshida et al., "Genetic lipid storage disease with lysososomal acid lipase deficiency in rats" Lab Anim Sci., 40:486-489 (1990).
Young et al., "Deficiency of Acid Esterase Activity in Wolman's Disease," Archives of Disease in Childhood, 45:664-665 (1970).
Yu et al., "Boosting Brain Uptake of a Therapeutic Antibody by Reducing Its Affinity for a Transcytosis Target," Sci Transl Med, 3:84ra44 (2011).
Zhang et al., "Biotherapeutic target or sink: analysis of the macrophage mannose receptor tissue distribution in murine models of lysosomal storage diseases," J. Inherit Metab Disl 34:795-809 (2011).
Zschenker et al., "Characterization of lysosomal acid lipase mutations in the signal peptide and mature polypeptide regions causing Wolman disease" Journal of Lipid Research 42:1033-1040 (2001).
Zschenker et al., "Lysosomal acid lipase as a preproprotein" J. Biochem., 136:65-72 (2004).
Zschenker et al., "Somatic Mutagenesis of Potential glycosylation Sites of Lysosomal Acid Lipase" J. Biochem., 137:387-394 (2005).
Zuliani et al., "Characterization of a New Form of Inherited Hypercholesterolemia: Familial Recessive Hypercholesterolemia," Arterioscler Throm Vasc Biol, 19:802-809 (1999).
Poorthuis et al., "The frequency of lysosomal storage disease in the Netherlands," Hum genet, 105:151-156 (1999).

\* cited by examiner

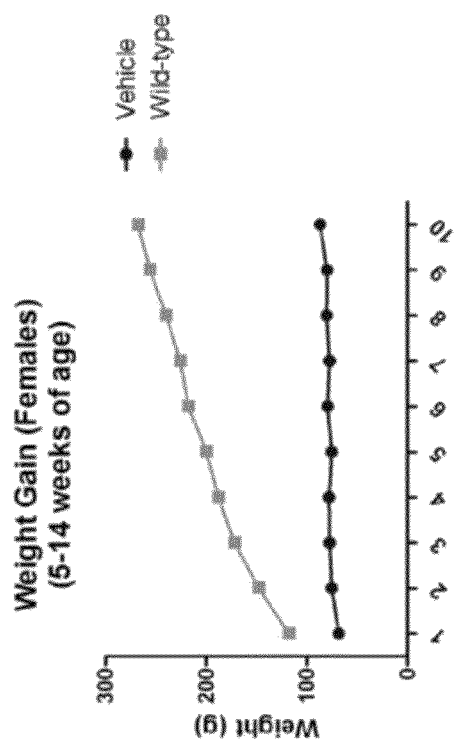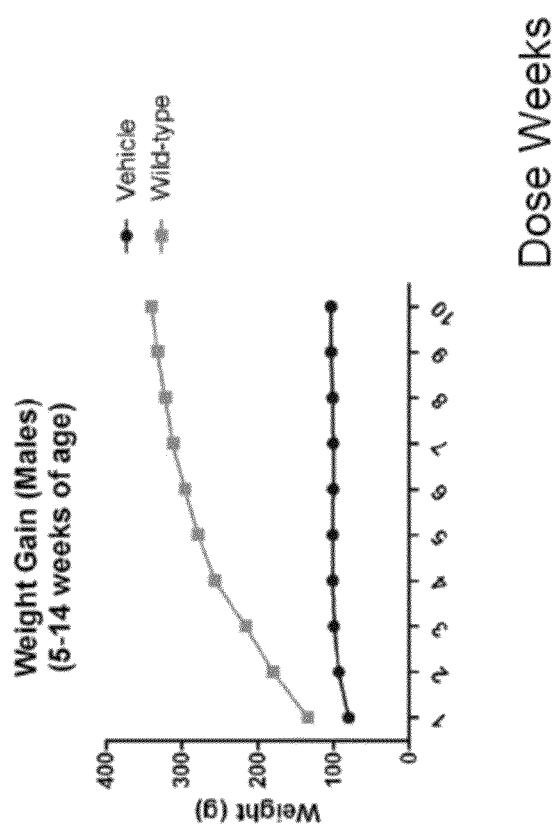
Fig. 5A-B

Fig. 6A-B

Fig. 8A-B

Experimental Design:

| Group | N | Genotype | Age* (wks) | Treatment | Dose (mg/kg) | Route | Total Injections (weekly) | Sacrifice |
|---|---|---|---|---|---|---|---|---|
| A | 3 | Homozygous | 5 | vehicle | 0 | IV | 10 | 24 hours post last dose |
| B | 6 | Homozygous | 5 | rhLAL | 0.5 | IV | 10 | 24 hours post last dose |
| C | 6 | Homozygous | 5 | rhLAL | 1 | IV | 10 | 24 hours post last dose |
| D | 6 | Homozygous | 5 | rhLAL | 3 | IV | 10 | 24 hours post last dose |
| E | 3 | Homozygous | 10 | vehicle | 0 | IV | 5 | 24 hours post last dose |
| F | 6 | Homozygous | 10 | rhLAL | 0.5 | IV | 5 | 24 hours post last dose |
| G | 6 | Homozygous | 10 | rhLAL | 1 | IV | 5 | 24 hours post last dose |
| H | 6 | Homozygous | 10 | rhLAL | 3 | IV | 5 | 24 hours post last dose |
| I | 3 | WT | 5 | None | None | NA | NA | day 100 ± 2 days |

* = week 5 (day 35 ± 3 days), week 10 (day 70 ± 3 days)

Note: 3 mg/kg group aborted due to observed death in 2/2 animals following 3rd dose.

| Dose (mg/kg) | # of Injections (starting on Day 35) |
|---|---|
| 0.1 | 5 or 10 |
| 2.0 | 5 or 10 |

Fig. 12

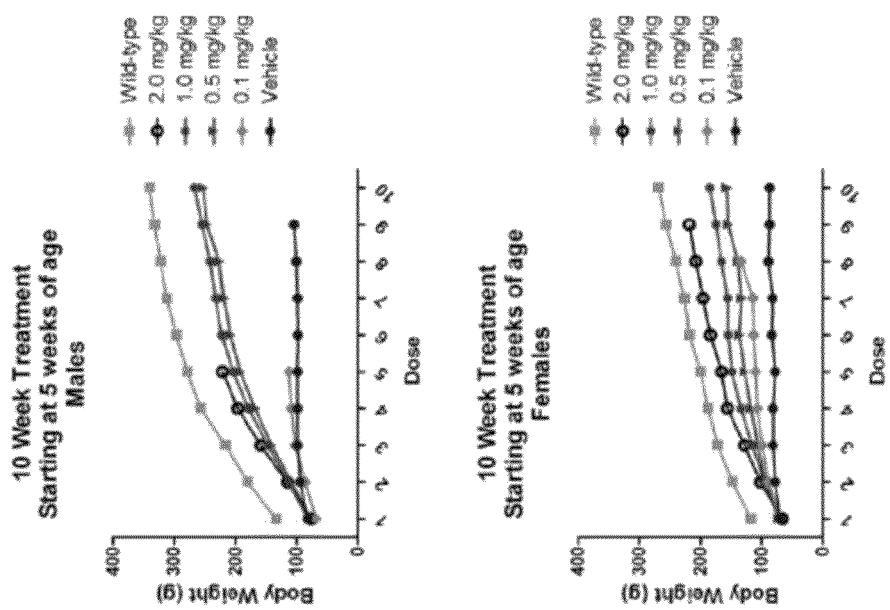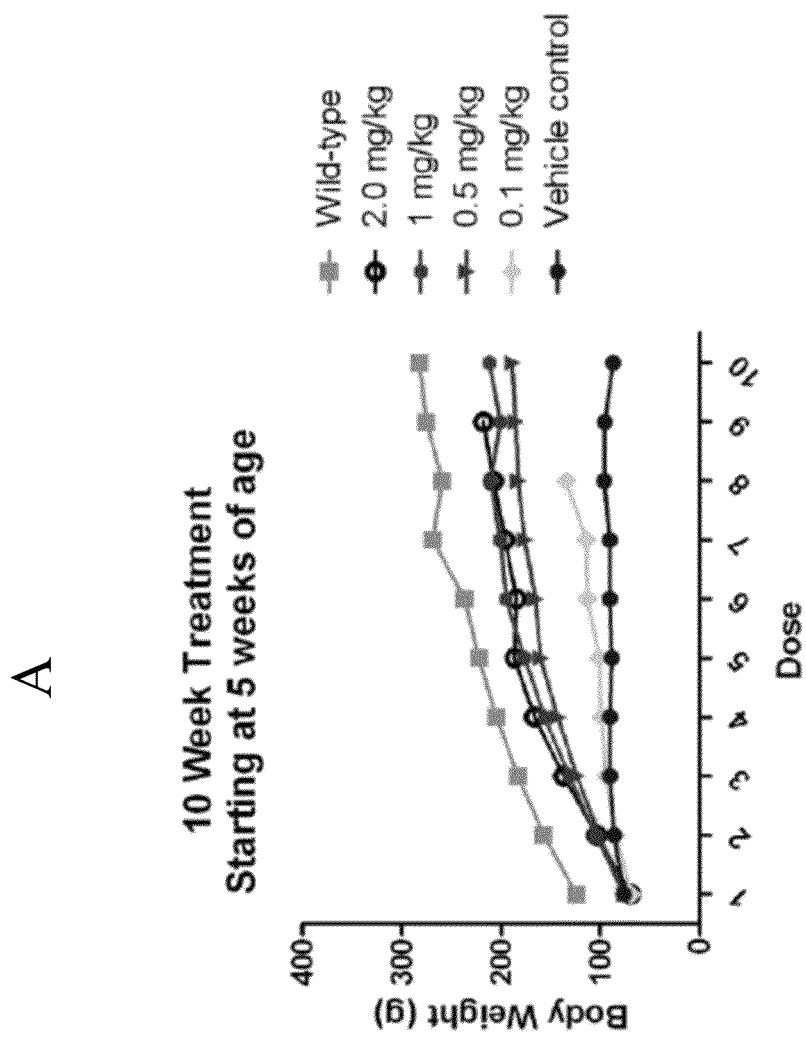
Fig. 15A-C

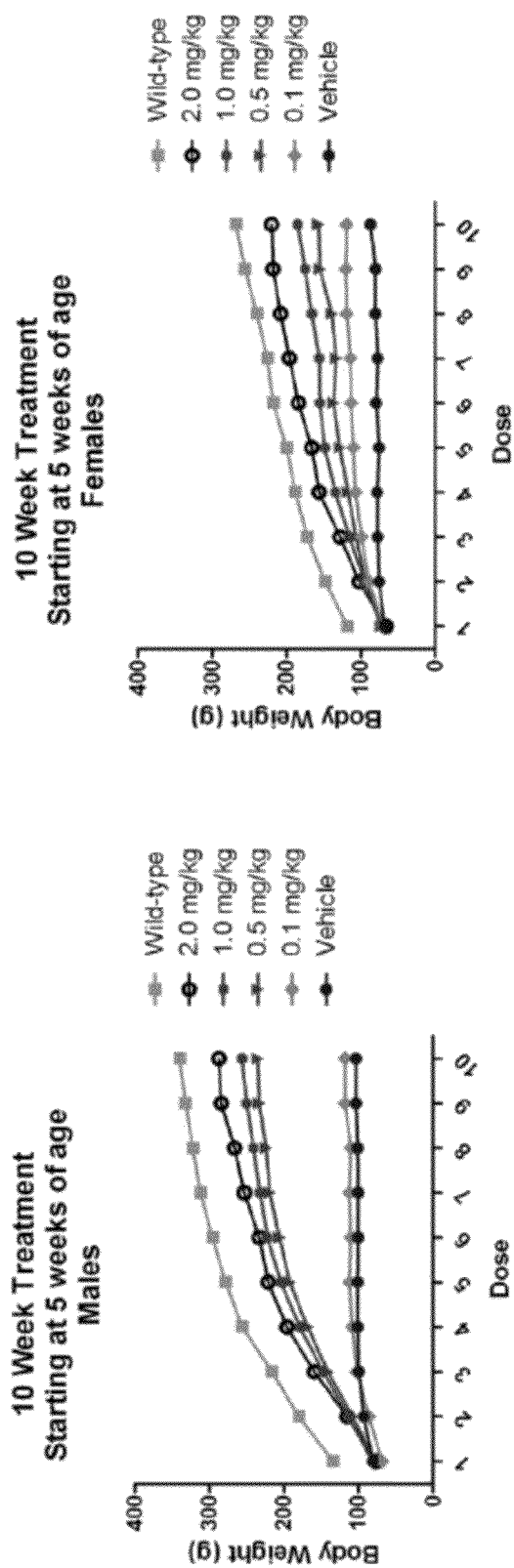
Fig. 15D-E

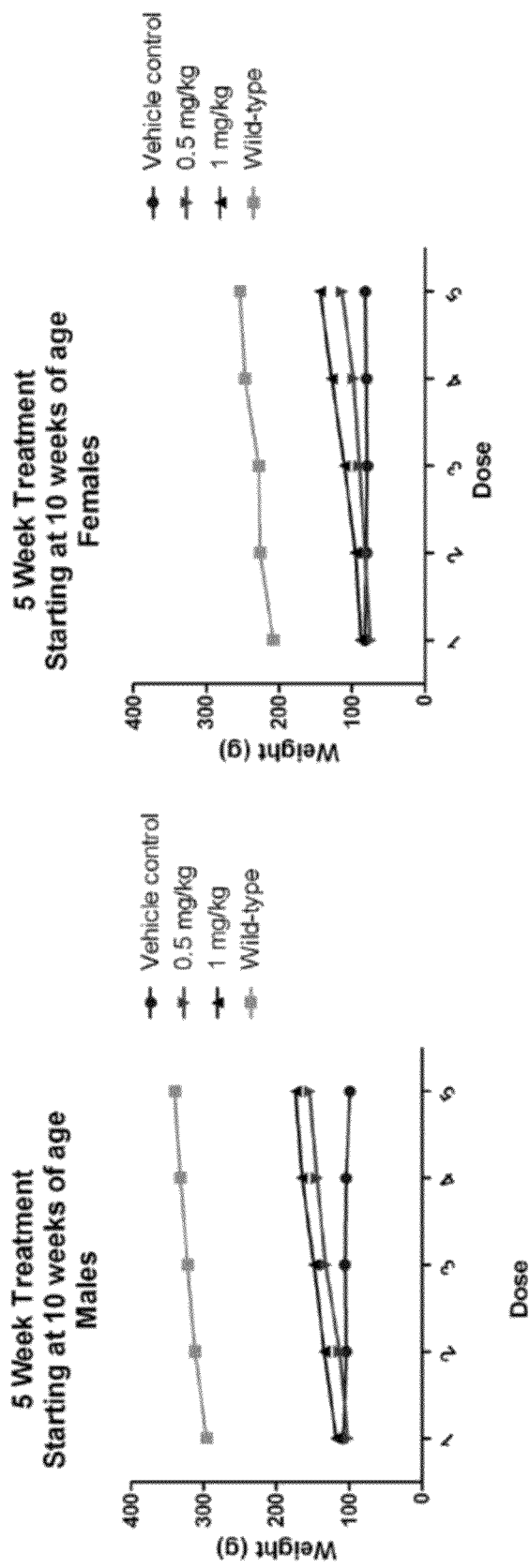
Fig. 17B-C

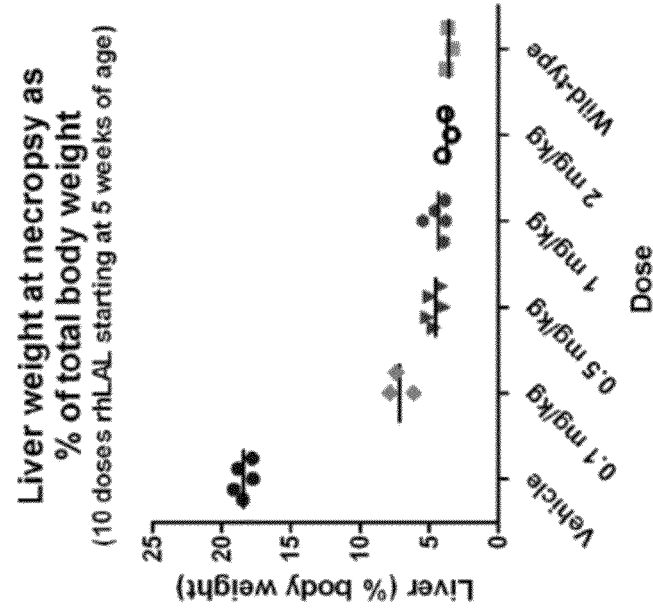
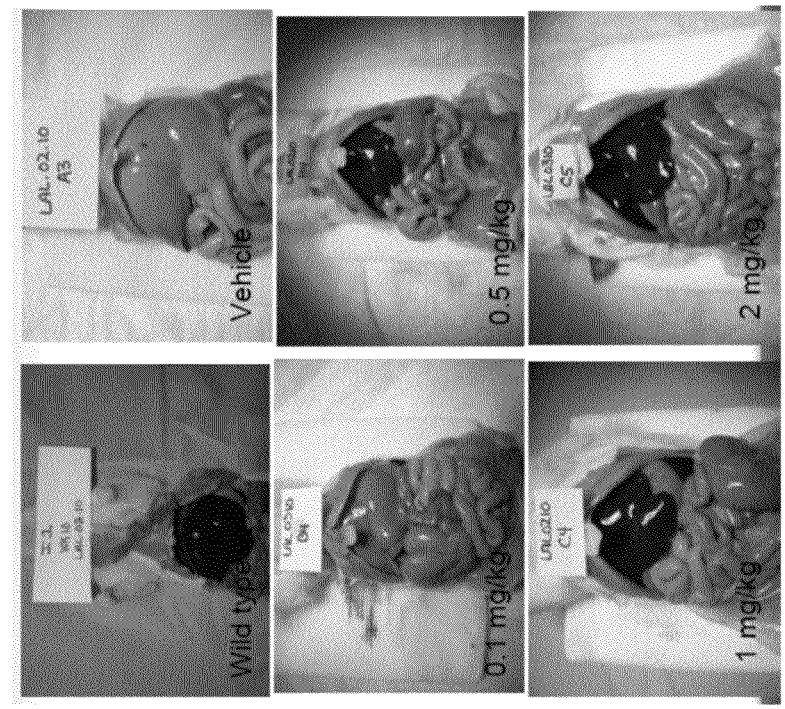
Fig. 18A-B

A

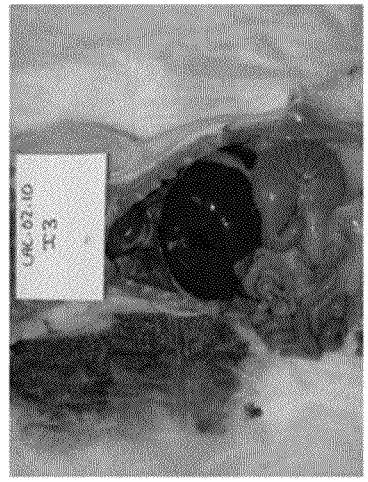
Fig. 19A

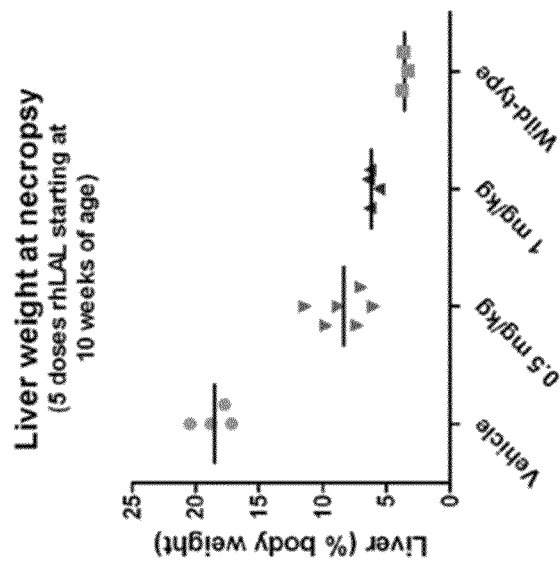
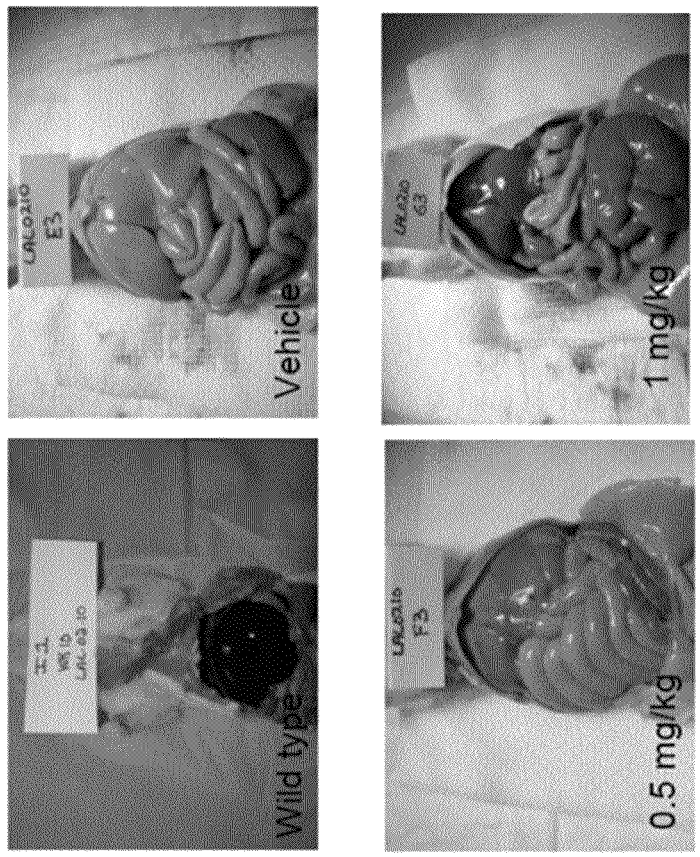
Fig. 19B-C

| Group | # Animals | Genotype | Initiation Age | Dose (mg/kg) | Regimen |
|---|---|---|---|---|---|
| A | 12 | lal -/- | 5 wks | 0 (veh) | Weekly for 26 injections |
| B | 12 | lal -/- | 5 wks | 0.1 | Weekly for 26 injections |
| C | 12 | lal -/- | 5 wks | 0.5 | Weekly for 26 injections |
| D | 12 | lal -/- | 5 wks | 1 | Weekly for 26 injections |
| E | 6 | WT | 5 wks | 1 | Weekly for 26 injections |
| F | 6 | WT | 5 wks | 0 (veh) | Weekly for 26 injections |
| G | 12 | lal -/- | 5 wks | 2/0.5 | Wkly 5 inj. Weekly 21 inj. |
| H | 12 | lal -/- | 5 wks | 2/0.25 | Wkly 5 inj. Weekly 21 inj. |
| I | 12 | lal -/- | 5 wks | 2/0.1 | Wkly 5 inj. Weekly 21 inj. |
| J | 12 | lal -/- | 5 wks | 2/0 (veh) | Wkly 5 inj. Weekly 21 inj. |

Fig. 36

| Group | No. of animals | Genotype | Material | Week 1-26 Dose (mg/kg) | Regimen |
|---|---|---|---|---|---|
| A | 12 | LAL-/- | Vehicle | 0 | Weekly IV dose for 26 weeks (Note: some animals were extended out to 38 weeks) |
| B | | | rhLAL | 0.05 | |
| C | | | | 0.5 | |
| D | | | | 1.0 | |
| E | 6 | WT | | 1.0 | |
| F | | | Vehicle control | 0 | |

Fig. 37

| Group | No. of animals | Genotype | Material | Week 1-5 Dose (mg/kg) | Week 6-26 Dose (mg/kg) | Regimen |
|---|---|---|---|---|---|---|
| E | 6 | WT | | 1.0 | 1.0 | Weekly IV dose for 26 weeks (Note: some animals were extended out to 38 weeks) |
| F | | | Vehicle control | 0 | 0 | |
| G | 12 | Lal -/- | rhLAL | 2.0 | 0.05 | |
| H | | | | 2.0 | 0.1 | |
| I | | | | 2.0 | 0.5 | |
| J | | | | 2.0 | 0 | |
| K | 6 | WT | N/A | N/A | N/A | Weekly body weight only |

Fig. 40

| Group | N (males) | Genotype | Age (weeks) | Route | Dose (mg/kg) | Dose Volume | Total # Injections (1/week) |
|---|---|---|---|---|---|---|---|
| A | 3 | (-/-) Homozygous | 5 | SC | 0 (vehicle) | 2 mL/kg | 5 (Days 1, 8, 15, 22, 29) |
| B | 3 | | | SC | 0.5 | | |
| C | 3 | | | SC | 2.5 | | |
| D | 3 | | | IV | 0.5 * | NA | |

* Dose based from previous study

Fig. 43

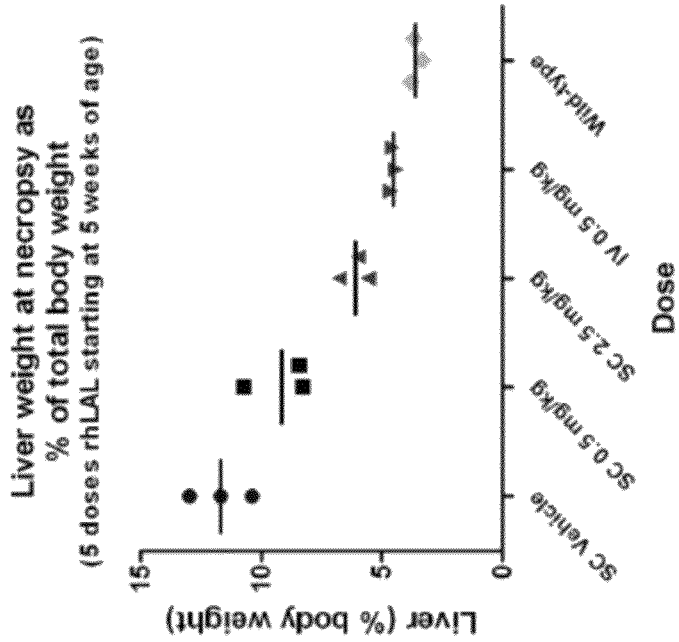
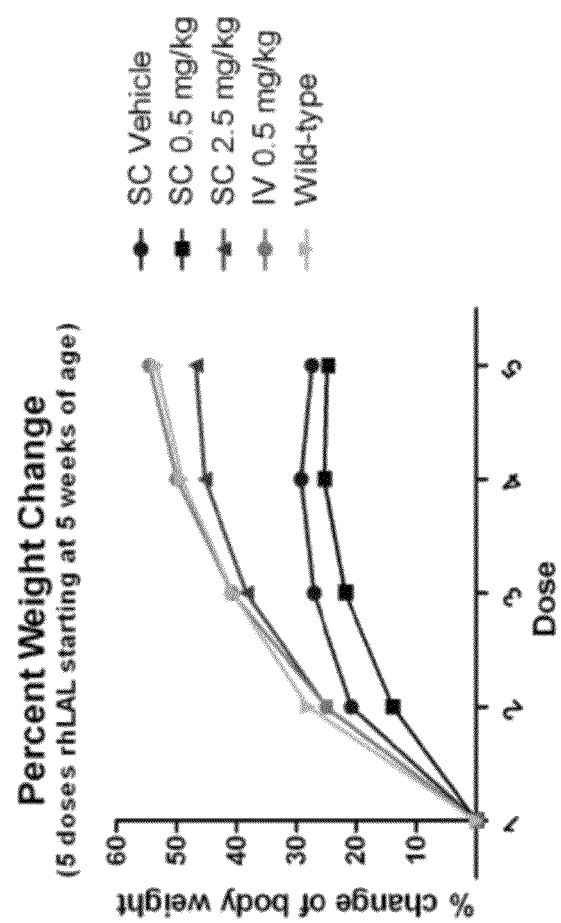
Fig. 45A-B

SEQUENCE LISTING

<160> NUMBER OF SEQ ID NOS: 4

<210> SEQ ID NO 1
<211> LENGTH: 378
<212> TYPE: PRT
<213> ORGANISM: Homo sapiens

<400> SEQUENCE: 1

```
Ser Gly Gly Lys Leu Thr Ala Val Asp Pro Glu Thr Asn Met Asn Val
1               5                   10                  15

Ser Glu Ile Ile Ser Tyr Trp Gly Phe Pro Ser Glu Glu Tyr Leu Val
            20                  25                  30

Glu Thr Glu Asp Gly Tyr Ile Leu Cys Leu Asn Arg Ile Pro His Gly
        35                  40                  45

Arg Lys Asn His Ser Asp Lys Gly Pro Lys Pro Val Val Phe Leu Gln
    50                  55                  60

His Gly Leu Leu Ala Asp Ser Ser Asn Trp Val Thr Asn Leu Ala Asn
65                  70                  75                  80

Ser Ser Leu Gly Phe Ile Leu Ala Asp Ala Gly Phe Asp Val Trp Met
                85                  90                  95

Gly Asn Ser Arg Gly Asn Thr Trp Ser Arg Lys His Lys Thr Leu Ser
            100                 105                 110

Val Ser Gln Asp Glu Phe Trp Ala Phe Ser Tyr Asp Glu Met Ala Lys
        115                 120                 125

Tyr Asp Leu Pro Ala Ser Ile Asn Phe Ile Leu Asn Lys Thr Gly Gln
    130                 135                 140

Glu Gln Val Tyr Tyr Val Gly His Ser Gln Gly Thr Thr Ile Gly Phe
145                 150                 155                 160

Ile Ala Phe Ser Gln Ile Pro Glu Leu Ala Lys Arg Ile Lys Met Phe
                165                 170                 175

Phe Ala Leu Gly Pro Val Ala Ser Val Ala Phe Cys Thr Ser Pro Met
            180                 185                 190

Ala Lys Leu Gly Arg Leu Pro Asp His Leu Ile Lys Asp Leu Phe Gly
        195                 200                 205

Asp Lys Glu Phe Leu Pro Gln Ser Ala Phe Leu Lys Trp Leu Gly Thr
    210                 215                 220

His Val Cys Thr His Val Ile Leu Lys Glu Leu Cys Gly Asn Leu Cys
225                 230                 235                 240

Phe Leu Leu Cys Gly Phe Asn Glu Arg Asn Leu Asn Met Ser Arg Val
                245                 250                 255

Asp Val Tyr Thr Thr His Ser Pro Ala Gly Thr Ser Val Gln Asn Met
            260                 265                 270

Leu His Trp Ser Gln Ala Val Lys Phe Gln Lys Phe Gln Ala Phe Asp
        275                 280                 285

Trp Gly Ser Ser Ala Lys Asn Tyr Phe His Tyr Asn Gln Ser Tyr Pro
    290                 295                 300

Pro Thr Tyr Asn Val Lys Asp Met Leu Val Pro Thr Ala Val Trp Ser
305                 310                 315                 320

Gly Gly His Asp Trp Leu Ala Asp Val Tyr Asp Val Asn Ile Leu Leu
                325                 330                 335

Thr Gln Ile Thr Asn Leu Val Phe His Glu Ser Ile Pro Glu Trp Glu
            340                 345                 350

His Leu Asp Phe Ile Trp Gly Leu Asp Ala Pro Trp Arg Leu Tyr Asn
        355                 360                 365
```

-continued

```
Lys Ile Ile Asn Leu Met Arg Lys Tyr Gln
    370                 375

<210> SEQ ID NO 2
<211> LENGTH: 21
<212> TYPE: PRT
<213> ORGANISM: Homo sapiens

<400> SEQUENCE: 2

Met Lys Met Arg Phe Leu Gly Leu Val Val Cys Leu Val Leu Trp Thr
1               5                   10                  15

Leu His Ser Glu Gly
            20

<210> SEQ ID NO 3
<211> LENGTH: 399
<212> TYPE: PRT
<213> ORGANISM: Homo sapiens

<400> SEQUENCE: 3

Met Lys Met Arg Phe Leu Gly Leu Val Val Cys Leu Val Leu Trp Thr
1               5                   10                  15

Leu His Ser Glu Gly Ser Gly Gly Lys Leu Thr Ala Val Asp Pro Glu
            20                  25                  30

Thr Asn Met Asn Val Ser Glu Ile Ile Ser Tyr Trp Gly Phe Pro Ser
        35                  40                  45

Glu Glu Tyr Leu Val Glu Thr Glu Asp Gly Tyr Ile Leu Cys Leu Asn
    50                  55                  60

Arg Ile Pro His Gly Arg Lys Asn His Ser Asp Lys Gly Pro Lys Pro
65                  70                  75                  80

Val Val Phe Leu Gln His Gly Leu Leu Ala Asp Ser Ser Asn Trp Val
                85                  90                  95

Thr Asn Leu Ala Asn Ser Ser Leu Gly Phe Ile Leu Ala Asp Ala Gly
            100                 105                 110

Phe Asp Val Trp Met Gly Asn Ser Arg Gly Asn Thr Trp Ser Arg Lys
        115                 120                 125

His Lys Thr Leu Ser Val Ser Gln Asp Glu Phe Trp Ala Phe Ser Tyr
    130                 135                 140

Asp Glu Met Ala Lys Tyr Asp Leu Pro Ala Ser Ile Asn Phe Ile Leu
145                 150                 155                 160

Asn Lys Thr Gly Gln Glu Gln Val Tyr Tyr Val Gly His Ser Gln Gly
                165                 170                 175

Thr Thr Ile Gly Phe Ile Ala Phe Ser Gln Ile Pro Glu Leu Ala Lys
            180                 185                 190

Arg Ile Lys Met Phe Phe Ala Leu Gly Pro Val Ala Ser Val Ala Phe
        195                 200                 205

Cys Thr Ser Pro Met Ala Lys Leu Gly Arg Leu Pro Asp His Leu Ile
    210                 215                 220

Lys Asp Leu Phe Gly Asp Lys Glu Phe Leu Pro Gln Ser Ala Phe Leu
225                 230                 235                 240

Lys Trp Leu Gly Thr His Val Cys Thr His Val Ile Leu Lys Glu Leu
                245                 250                 255

Cys Gly Asn Leu Cys Phe Leu Leu Cys Gly Phe Asn Glu Arg Asn Leu
            260                 265                 270

Asn Met Ser Arg Val Asp Val Tyr Thr Thr His Ser Pro Ala Gly Thr
        275                 280                 285
```

```
Ser Val Gln Asn Met Leu His Trp Ser Gln Ala Val Lys Phe Gln Lys
    290             295                 300
Phe Gln Ala Phe Asp Trp Gly Ser Ser Ala Lys Asn Tyr Phe His Tyr
305                 310                 315                 320
Asn Gln Ser Tyr Pro Pro Thr Tyr Asn Val Lys Asp Met Leu Val Pro
                325                 330                 335
Thr Ala Val Trp Ser Gly Gly His Asp Trp Leu Ala Asp Val Tyr Asp
            340                 345                 350
Val Asn Ile Leu Leu Thr Gln Ile Thr Asn Leu Val Phe His Glu Ser
        355                 360                 365
Ile Pro Glu Trp Glu His Leu Asp Phe Ile Trp Gly Leu Asp Ala Pro
    370                 375                 380
Trp Arg Leu Tyr Asn Lys Ile Ile Asn Leu Met Arg Lys Tyr Gln
385                 390                 395

<210> SEQ ID NO 4
<211> LENGTH: 20
<212> TYPE: PRT
<213> ORGANISM: Homo sapiens

<400> SEQUENCE: 4

Met Ala Cys Leu Glu Phe Val Pro Phe Asp Val Gln Met Cys Leu Glu
1               5                   10                  15
Phe Leu Pro Ser
            20
```

METHODS FOR TREATING LYSOSOMAL ACID LIPASE DEFICIENCY

CROSS REFERENCE TO RELATED APPLICATIONS

This application claims priority to International Application Number PCT/US/2012/025239 filed on Feb. 15, 2012, which claims priority to U.S. Provisional Patent Application Ser. No. 61/443,179, filed Feb. 15, 2011, the entirety of each of which is incorporated herein by reference.

BACKGROUND

Lysosomal acid lipase (LAL) deficiency is a rare but serious disease. Under normal conditions, human body produces lysosomal acid lipase (LAL), an enzyme that breaks down fatty material (cholesteryl esters and triglycerides). LAL Deficiency happens when the body is not producing enough LAL. The lack of the LAL enzyme typically results in a massive build-up of fatty material in various tissues including liver, spleen, gut, blood vessel walls and other important organs. As a result, LAL deficiency is typically associated with significant morbidity and mortality and can affect individuals from infancy through adulthood.

Extremely low levels of the LAL enzyme typically causes early onset of LAL Deficiency, sometimes called Wolman Disease (also known as Wolman's disease, Wolman's syndrome). Early onset LAL Deficiency typically affects infants in the first year of life. For example, the build-up of fatty material in the cells of the gut prevents the body from absorbing nutrients. Consequently, Wolman disease is a rapidly progressive and typically fatal condition characterized by malabsorption, growth failure and significant weight loss. These infants typically die during their first year of life from a failure to grow and from other complications due to liver failure.

Later onset LAL Deficiency is sometimes called Cholesteryl Ester Storage Disease (CESD) and can affect children and adults. Typically, CESD patients experience enlarged liver (hepatomegaly), cirrhosis, chronic liver failure, severe premature atherosclerosis, hardening of the arteries, or elevated levels of serum Low Density Lipoprotein (LDL). Children may also have calcium deposits in the adrenal glands and develop jaundice.

Currently, there is no approved therapy for LAL deficiency.

SUMMARY OF THE INVENTION

The present invention provides compositions and methods for effective treatment of a lysosomal acid lipase deficiency (LALD) disease, in particular, Wolman's disease and Cholesteryl Ester Storage Disease (CESD). The present invention is, in part, based on the discovery that administration of a recombinant lysosomal acid lipase to an animal disease model is unexpectedly effective in treating (e.g., ameliorating, inhibiting, or delaying onset of) various symptoms of LALD diseases, including massive accumulation of fatty materials in various organs (e.g., liver, spleen, gut) and, in particular, developmental impairment (also referred to as cachexia or failure to thrive), a most devastating symptom of Wolman's disease.

Thus, in one aspect, the present invention provides a method of treating developmental impairment or malnutrition in an individual suffering from an LALD disease, including administering to the individual a therapeutic effective amount of a lysosomal acid lipase. In some embodiments, the LALD disease being treated is Wolman's disease. In some embodiments, the LALD disease being treated is cholesteryl ester storage disease (CESD).

In some embodiments, treating developmental impairment or malnutrition comprises promoting weight gain. In some embodiments, treating developmental impairment or malnutrition comprises reducing or preventing weight loss. In some embodiments, treating developmental impairment or malnutrition comprises reducing or eliminating tissue weakness or wasting. In some embodiments, the tissue weakness or wasting is muscle and/or subcutaneous weakness or wasting. In some embodiments, treating developmental impairment or malnutrition comprises reducing frequency and/or intensity of vomiting and/or diarrhea.

In certain embodiments, administering of the lysosomal acid lipase further results in resolution of gross liver, spleen, and/or intestine pathology (e.g., a reduction in liver, spleen, and/or gut size relative to body weight). In some embodiments, administering of the lysosomal acid lipase further results in a reduction of lipid accumulation in tissues. In some embodiments, the tissues are selected from the group consisting of liver, spleen, intestine, bone marrow, blood vessel walls, and combination thereof. In some embodiments, the lipid comprises cholesterol and/or triglycerides. In some embodiments, the lipid accumulation is reduced by more than 10%, 20%, 30%, 40%, 50%, 60%, 70%, 80%, 90%, or 95%, as compared to the lipid accumulation level before the treatment. In some embodiments, the lipid accumulation is substantially eliminated.

It will be appreciated that the lysosomal acid lipase may be administered by any appropriate method. In certain embodiments, the lysosomal acid lipase is administered intravenously. In certain embodiments, the lysosomal acid lipase is administered subcutaneously. In some embodiments, the lysosomal acid lipase is administered intramuscularly. In some embodiments, the lysosomal acid lipase is administered intrathecally or intraventricularly. In certain embodiments, the lysosomal acid lipase is administered orally.

A therapeutic effective amount of a lysosomal acid lipase may be administered periodically at an administration interval. In some embodiments, the lysosomal acid lipase is administered monthly. In some embodiments, the lysosomal acid lipase is administered bimonthly. In some embodiments, the lysosomal acid lipase is administered weekly. In some embodiments, the lysosomal acid lipase is administered twice a week. In some embodiments, the lysosomal acid lipase is administered daily. In some embodiments, the lysosomal acid lipase is administered at an interval that is varied over time.

In certain embodiments, the therapeutic effective amount is at least about 0.01 mg/kg body weight. In some embodiments, the therapeutic effective amount is at least about 0.1 mg/kg body weight. In certain embodiments, the therapeutic effective amount is at least about 0.5 mg/kg body weight. In certain embodiments, the therapeutic effective amount is at least about 1 mg/kg body weight. In some embodiments, the therapeutic effective amount is no greater than about 10 mg/kg body weight. In some embodiments, the therapeutic effective amount is no greater than about 5 mg/kg body weight. In some embodiments, the therapeutic effective amount is no greater than about 4 mg/kg body weight. In some embodiments, the therapeutic effective amount is no greater than about 3 mg/kg body weight. In some embodiments, the therapeutic effective amount is no greater than about 2 mg/kg body weight. In some embodiments, the therapeutic effective amount is no greater than about 1 mg/kg body weight. In some embodiments, the therapeutic effective amount ranges from about 0.01-10 mg/kg body weight. In some embodiments, the therapeutic effective amount ranges from about 0.01-5 mg/kg body weight. In some embodiments, the therapeutic effective amount ranges from about 0.01-2 mg/kg body weight. In some embodiments, the therapeutic effective amount ranges from about 0.01-1 mg/kg body weight. In some embodiments, the therapeutic effective amount is about 0.01, 0.05, 0.1, 0.2, 0.3, 0.4, 0.5, 0.6, 0.7, 0.8, 0.9, or 1.0 mg/kg body weight.

In certain embodiments, the lysosomal acid lipase has an amino acid sequence at least 80% identical to human lysosomal acid lipase (SEQ ID NO:1). In some embodiments, the lysosomal acid lipase has an amino acid sequence at least 90% identical to human lysosomal acid lipase (SEQ ID NO:1). In some embodiments, the lysosomal acid lipase has an amino acid sequence at least 95% identical to human lysosomal acid lipase (SEQ ID NO:1). In some embodiments, the lysosomal acid lipase is human lysosomal acid lipase (SEQ ID NO:1).

In some embodiments, the lysosomal acid lipase is recombinantly produced. In some embodiments, the lysosomal acid lipase is recombinantly produced from mammalian cells. In some embodiments, the lysosomal acid lipase is recombinantly produced in transgenic avian. In some embodiments, the lysosomal acid lipase contains a glycosylation pattern that is different than that of a naturally-occurring lysosomal acid lipase. In some embodiments, the lysosomal acid lipase contains one or more N-glycan structures.

In another aspect, the present invention provides a method of treating a lysosomal acid lipase deficiency (LALD) disease (e.g., Wolman's disease or cholesteryl ester storage disease (CESD)), including administering to an individual suffering from or susceptible to the LALD disease a therapeutic effective amount of a lysosomal acid lipase periodically at an administration interval. In some embodiments, the therapeutic effective amount is at least about 0.01 mg/kg body weight (e.g., at least about 0.05 mg/kg, at least about 0.1 mg/kg, at least about 0.2 mg/kg, at least about 0.3 mg/kg, at least about 0.4 mg/kg, at least about 0.5 mg/kg, at least about 0.6 mg/kg, at least about 0.7 mg/kg, at least about 0.8 mg/kg, at least about 0.9 mg/kg, or at least about 1.0 mg/kg body weight). In some embodiments, the therapeutic effective amount is no greater than about 20 mg/kg body weight (e.g., no greater than about 15 mg/kg, no greater than about 10 mg/kg, no greater than about 8 mg/kg, no greater than about 6 mg/kg, no greater than about 5 mg/kg, no greater than about 4 mg/kg, no greater than about 3 mg/kg, no greater than about 2 mg/kg, or no greater than about 1 mg/kg body weight). In some embodiments, the lysosomal acid lipase is administered intravenously. In some embodiments, the lysosomal acid lipase is administered subcutaneously.

In still another aspect, the present invention provides a method of treating a lysosomal acid lipase deficiency (LALD) disease (e.g., Wolman's disease or cholesteryl ester storage disease (CESD)), including administering to an individual suffering from or susceptible to the LALD disease a therapeutic effective amount of a lysosomal acid lipase periodically at an administration interval, wherein the lysosomal acid lipase is administered subcutaneously.

In yet another aspect, the present invention provides a method of treating a lysosomal acid lipase deficiency (LALD) disease (e.g., Wolman's disease or cholesteryl ester storage disease (CESD)), including administering to an individual suffering from or susceptible to the LALD disease a therapeutic effective amount of a lysosomal acid lipase periodically at an administration interval such that relative liver weight or volume (e.g., liver weight or volume relative to the body weight) of the individual being treated is reduced by more than about 50% (e.g., more than about 60%, about 70%, about 80%, about 90%, or about 95%) as compared to a control. In some embodiments, a suitable control is the relative liver weight or volume of the individual being treated before the treatment. In some embodiments, a suitable control is the average relative liver weight or volume of control individuals suffering from the same form of the LALD disease without treatment. In some embodiments, administering the therapeutic effective amount of the lysosomal acid lipase results in the relative liver weight or volume of the individual being treated comparable to that of a healthy individual. In some embodiments, administering of the therapeutic effective amount of the lysosomal acid lipase further results in reduced relative spleen weight or volume (e.g., spleen weight or volume relative to the body weight) of the individual being treated by more than about 50% (e.g., more than about 60%, about 70%, about 80%, about 90%, or about 95%) as compared to a control (e.g., the relative spleen weight or volume of the individual being treated before the treatment, or the average relative spleen weight or volume of control individuals suffering from the same form of the LALD disease without treatment). In some embodiments, administering of the therapeutic effective amount of the lysosomal acid lipase further results in the relative spleen weight or volume of the individual being treated comparable to that of a healthy individual.

In another aspect, the present invention provides a method of treating a lysosomal acid lipase deficiency (LALD) disease, including administering to an individual suffering from or susceptible to the LALD disease a lysosomal acid lipase using a dosing regimen that includes using different doses at different stages of treatment. In some embodiments, the present invention provides a method of treating a lysosomal acid lipase deficiency (LALD) disease, including administering to an individual suffering from or susceptible to the LALD disease a lysosomal acid lipase at a first dose periodically for a first period, and administering to the individual the lysosomal acid lipase at a second dose periodically for a second period. In some embodiments, the second dose is lower than the first dose. In some embodiments, the first dose ranges from 0.1-5 mg/kg body weight (e.g., about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 mg/kg body weight). In some embodiments, the second dose ranges from 0-2 mg/kg body weight (e.g., about 0.01, 0.02, 0.04, 0.06, 0.08, 0.1, 0.2, 0.3, 0.4, 0.5, 0.6, 0.7, 0.8, 0.9, 1.0, 1.2, 1.4, 1.6, 1.8, or 2.0 mg/kg body weight). In some embodiments, the first period is 3 months, 6 months, 9 months, 12 months or longer. In some embodiments, the second period is longer than 6 months, 12 months, 2 years, or life time.

In still another aspect, the present invention provides pharmaceutical compositions for treating a lysosomal acid lipase deficiency (LALD) disease (e.g., Wolman's disease or CESD), including a therapeutic effective amount of a lysosomal acid lipase and a pharmaceutical carrier as described in various embodiments above.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only, not for limitation.

FIG. 5 depicts an exemplary weight gain comparison of wild-type and LAL deficient Yoshida rats at 5-14 weeks of age. FIG. 5A depicts a weight gain comparison of wild type and LAL deficient male rats. Wild type consistently gained weight at a greater rate than the LAL deficient rats. FIG. 5B depicts a weight gain comparison of wild type and LAL deficient female rats, with results similar to the males.

FIG. 6 depicts an exemplary progression of abdominal distension of LAL deficient Yoshida rats at 7 and 19 weeks of age. FIG. 6A is a lateral view of female LAL deficient mice displaying reduced weight gain over time. FIG. 6B is a ventral view of the limited abdominal distension in the LAL deficient females.

FIG. 8A depicts liver weight at necropsy as a percent of total body weight for wild type and LAL deficient rats. LAL deficient rats experienced greater liver weights compared to wild type rats. FIG. 8B depicts spleen weight at necropsy as a percent of total body weight for wild type and LAL deficient rats. LAL deficient rats experienced greater spleen weights compared to wild type rats.

FIG. 12 provides an exemplary study design for rhLAL treatment. Homozygous LAL deficient Yoshida rats were administered 5 or 10 weekly injections of varying doses of rhLAL or vehicle control via intravenous administration. Control wild-type rats were untreated.

FIG. 15 depicts exemplary body weight gain in male and female wild-type rats and LAL deficient Yoshida rats treated with vehicle control or varying doses of rhLAL for 10 weeks starting at 5 weeks of age. FIG. 15A depicts the body weight gain of wild-type and LAL deficient rats over 10 weeks of treatment. FIG. 15B and FIG. 15D depicts the body weight gain in wild-type and LAL deficient males during a 10 week treatment. FIG. 15C and FIG. 15E depicts the body weight gain in wild-type and LAL deficient females during a 10 week treatment. Weekly percent body weight gain for LAL treated animals was similar to that of wild-type animals.

FIG. 17 depicts exemplary body weight gain in wild-type rats and LAL deficient Yoshida rats treated with vehicle control or varying doses of rhLAL for 5 weeks starting at 10 weeks of age. FIG. 17B depicts the weight gain over 5 weeks for wild-type and LAL deficient male rats. FIG. 17C depicts the weight gain over 5 weeks for wild-type and LAL deficient female rats. Weight gain was observed in animals treated with rhLAL using the 5-week dosing regimen.

FIG. 18 depicts exemplary resolution of gross liver pathology and liver weight at necropsy of wild-type rats and LAL deficient Yoshida rats treated with vehicle control or varying doses of rhLAL for 10 weeks starting at 5 weeks of age. Animals were necropsied at week 14. FIG. 18A depicts the gross liver pathology of wild-type and LAL deficient rats at necropsy. FIG. 18B depicts the liver weight at necropsy as a percentage of total body weight for wild-type and LAL deficient rats. Animals treated with rhLAL exhibited a similar relative liver weight compared to wild-type animals.

FIG. 19 depicts exemplary resolution of gross liver pathology at necropsy of wild-type rats and LAL deficient Yoshida rats treated with five doses of vehicle control or five doses of varying amounts of rhLAL. Animals were necropsied at week 9. FIG. 19A depicts the gross liver pathology of wild-type and LAL deficient rats at necropsy at 9 weeks after treatment with five doses of 0.1 mg/kg or 2.0 mg/kg rhLAL. FIG. 19B depicts the gross liver pathology of wild-type and LAL deficient rats at necropsy after treatment with five doses of 0.5 mg/kg or 1.0 mg/kg rhLAL; dosing began at 10 weeks of age. FIG. 19C depicts the liver weight at necropsy for wild-type and LAL deficient 10 week old mice after receiving five doses of rhLAL.

FIG. 36 provides an exemplary study design for a survival and/or maintenance dose study. Wild-type rats or homozygous LAL deficient Yoshida rats are treated with various doses of rhLAL (e.g., 0.1 mg/kg, 0.5 mg/kg, 1 mg/kg) or a vehicle control, starting at 5 weeks of age, weekly for 26 weeks for survival dose studies. Wild-type rats or homozygous LAL deficient Yoshida rats are treated with a 2 mg/kg "loading dose" of rhLAL weekly for 5 weeks followed by various amounts rhLAL weekly for 21 weeks for maintenance dose studies.

FIG. 37 provides an exemplary study design for a survival dose study.

FIG. 40 provides an exemplary study design for a clearance and maintenance study.

FIG. 43 provides an exemplary study design for a pharmacodynamic study.

FIG. 45 depicts an exemplary percent body weight change and relative liver weight of wild-type rats or homozygous LAL deficient Yoshida rats treated with various amounts of rhLAL delivered subcutaneously (SC) or intravenously (IV). FIG. 45A depicts the percent change in weight of wild type and homozygous LAL deficient rats. A lower body weight gain was observed over the course of treatment in animals administered SC vehicle and SC 0.5 mh/kg rhLAL. Animals treated with SC 2.5 mg/kg and IV 0.5 mg/kg experiences increased body weight throughout rhLAL treatment. FIG. 45B depicts a dose response in liver weights when compared as percentage of total body weight. The SC 2.5 mg/kg rhLAL treated animals approximate the IV 0.5 mg/kg rhLAL treated animals in relative liver weight.

DEFINITIONS

Figure 1:
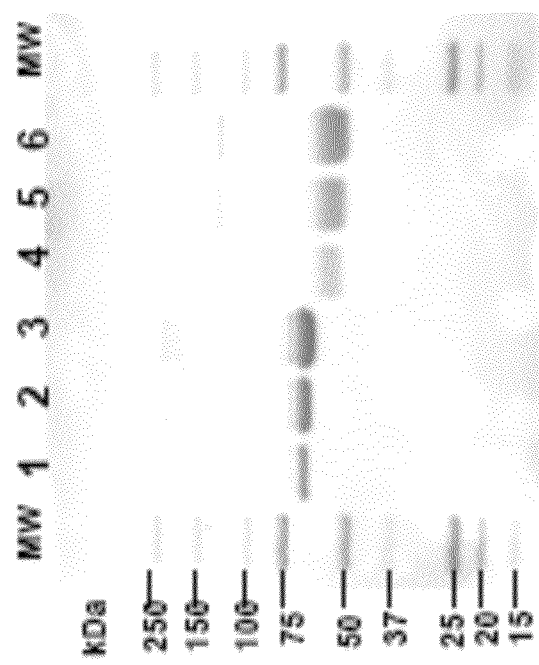
FIG. 1 depicts exemplary SDS-PAGE analysis of rhLAL. rhLAL was analyzed by SDS-PAGE and visualized by Coomassie stain and compared to BSA. Lanes 1-3: BSA, 1, 2.5, and 5 ug, respectively. Lanes 4-6: rhLAL, 1, 2.5 and 5 ug, respectively. Protein molecular weight markers are labeled on the left.

In order for the present invention to be more readily understood, certain terms are first defined below. Additional definitions for the following terms and other terms are set forth throughout the specification.

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes reduction of accumulated materials inside lysosomes of relevant diseases tissues.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Developmental impairment: As used herein, the phrase "developmental impairment," also referred to as "failure to thrive" or "cachexia", includes various symptoms associated with malnutrition, or growth failure in a patient suffering from a LALD disease including, but not limited to, poor weight gain or weight lose, weakness or wasting of various tissues (muscle, subcutaneous tissues, etc). Developmental impairment is typically associated with frequent vomiting, diarrhea, or abdominal distension. As used herein, developmental impairment encompasses symptoms of both Wolman's disease and CESD.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease (e.g., LAL deficiency) as the individual being treated, who is about the same age as the individual being treated (to ensure that the stages of the disease in the treated individual and the control individual(s) are comparable).

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult human) suffering from a lysosomal storage disease, for example, LAL deficiency disease (e.g., early-onset such as Wolman's disease; later-onset such as Cholesteryl Ester Storage Disease (CESD)).

Lysosomal enzyme deficiency: As used herein, "lysosomal enzyme deficiency" refers to a group of genetic disorders that result from deficiency in at least one of the enzymes (e.g., lysosomal acid lipase) that are required to break macromolecules (e.g., fatty materials) down to peptides, amino acids, monosaccharides, nucleic acids and fatty acids in lysosomes. As a result, individuals suffering from lysosomal enzyme deficiencies have accumulated materials in various tissues (e.g., liver, spleen, gut, blood vessel walls and other organs).

Lysosomal enzyme: As used herein, the term "lysosomal enzyme" refers to any enzyme (e.g., lysosomal acid lipase (LAL)) that is capable of reducing accumulated materials in mammalian tissues or that can rescue or ameliorate one or more lysosomal enzyme deficiency symptoms (e.g., developmental impairment, liver failure, etc.). Lysosomal enzymes suitable for the invention include both wild-type or modified lysosomal enzymes and can be produced using recombinant and synthetic methods or purified from nature sources.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids., and/or as having "polar" or "non-polar" side chains Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Therapeutically effective amount: As used herein, the term "therapeutically effective amount" refers to an amount of a therapeutic lysosomal enzyme (e.g., lysosomal acid lipase (LAL)) protein which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a therapeutic protein (e.g., lysosomal acid lipase deficiency (LALD) disease) that partially or completely alleviates, ameliorates, relieves, inhibits, delays onset of, reduces severity of and/or reduces incidence of one or more symptoms or features of a particular disease, disorder, and/or condition (e.g., lysosomal acid lipase deficiency (LALD) disease). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION

The present invention provides compositions and methods for treatment of lysosomal acid lipase deficiency (LALD) diseases, in particular, Wolman's disease and/or CESD. Among other things, the present invention provides compositions and methods for administering to a mammal suffering from or susceptible to a LALD disease a therapeutic effective amount of a lysosomal acid lipase.

Various aspects of the invention are described in detail in the following sections. The use of sections is not meant to limit the invention. Each section can apply to any aspect of the invention. In this application, the use of "or" means "and/or" unless stated otherwise.

Lysosomal Acid Lipase Deficiency

Lysosomal Acid Lipase (LAL) is an enzyme that hydrolyzes cholesterol esters and triglycerides in the lysosome. LAL deficiency disease (LALD) is an autosomal recessive genetic disorder that results from a lack of LAL activity and typically leads to massive build-up of fatty material in various tissues. LALD can manifest as early onset of LALD, sometimes called Wolman Disease (also known as Wolman's disease, Wolman's syndrome), which typically affects infants in the first year of life. Alternatively or additionally, LALD can manifest as later onset LALD (sometimes called Cholesteryl Ester Storage Disease (CESD)), which can affect children and adults.

Individuals affected by Wolman Disease typically have harmful amounts of lipids that accumulate in the spleen, liver, bone marrow, small intestine, adrenal glands, lymph nodes, among other tissues. In some cases, calcium deposits are seen in the adrenal glands of affected individuals. Infants with Wolman disease usually appear healthy at birth, but soon develop signs and symptoms of the disorder, including hepatosplenomegaly, developmental impairment or cachexia (poor weight gain, weight loss, tissue weakness or wasting), low muscle tone, jaundice, vomiting, diarrhea, developmental delay, anemia, and/or poor absorption of nutrients from food (see, for example, Genetics Home Reference http://ghr.nlm.nih.gov/, the entire contents of which is incorporated herein by reference). These infants typically develop severe malnutrition and die during their first year of life. For example, Crocker and colleagues presented case studies of three individuals affected by Wolman Disease (Crocker, et al. *Pediatrics* "Wolman's Disease: Three New Patients with a Recently Described Lipidosis"; 1965, the entire contents of which is incorporated herein by reference). Each of the three individuals studied by Crocker and colleagues were admitted to the hospital due at least in part to failure to gain or difficulty in weight gain. The individuals also suffered from diarrhea and vomiting, among other things, and despite nutritional efforts, each of the infants died in a condition of inanition.

Later onset LAL Deficiency is sometimes called Cholesteryl Ester Storage Disease (CESD) and can affect children and adults. Typically, CESD patients experience enlarged liver (hepatomegaly), cirrhosis, chronic liver failure, severe premature atherosclerosis, hardening of the arteries, or elevated levels of serum Low Density Lipoprotein (LDL). Children may also have calcium deposits in the adrenal glands and develop jaundice.

Non-human animal models have been developed to study LALD. The Yoshida (LAL deficient) rat, has been characterized as an animal model of a genetic lipid storage disease most analogous to human Wolman's disease (Yoshida and Kuriyama, *Laboratory Animal Science* 40(5) 1990, the entire contents of which is incorporated herein by reference). Like humans, affected rats inherit the disease in an autosomal recessive manner and the disease is characterized by developmental impairment and cachexia, hepatosplenomegaly, lymph node enlargement, and thickened dilated intestine. Many characteristic foam cells are observed in livers and spleens of affected mice. Massive intracellular storage of both cholesterol esters and triglycerides are observed in the liver, accumulated fatty materials in mammalian tissues or that can rescue or ameliorate one or more lysosomal acid lipase deficiency (LALD) disease symptoms (e.g., developmental impairment, or liver failure, etc.).

In some embodiments, human lysosomal acid lipase (LAL) (also referred to as human lysosomal acid lipid lipase or cholesteryl ester hydrolase) is used. Typically, a mature form of human LAL is used. The sequence of a mature human LAL (SEQ ID NO:1) is listed below in Table 1 and described below. Typically, human LAL is first synthesized as a precursor protein containing a 21-amino acid signal peptide at the N-terminus The signal peptide is cleaved post-translationally resulting in the mature form of human LAL. The sequences of the signal peptide (SEQ ID NO:2) and the full length precursor protein (SEQ ID NO:3) are also shown in Table 1.

TABLE 1

| Human Lysosomal Acid Lipase/Cholesteryl Ester Hydrolase (P38571) | |
|---|---|
| Mature form | SGGKLTAVDPETNMNVSEIISYWGFPSEEYLVETEDGYILCLNRIPHGRKNHSDKGP KPVVFLQHGLLADSSNWVTNLANSSLGFILADAGFDVWMGNSRGNTWSRKHKTLSVS QDEFWAFSYDEMAKYDLPASINFILNKTGQEQVYYVGHSQGTTIGFIAFSQIPELAK RIKMFFALGPVASVAFCTSPMAKLGRLPDHLIKDLFGDKEFLPQSAFLKWLGTHVCT HVILKELCGNLCFLLCGFNERNLNMSRVDVYTTHSPAGTSVQNMLHWSQAVKFQKFQ AFDWGSSAKNYFHYNQSYPPTYNVKDMLVPTAVWSGGHDWLADVYDVNILLTQITNL VFHESIPEWEHLDFIWGLDAPWRLYNKIINLMRKYQ (SEQ ID NO: 1) |
| Signal Sequence | MKMRFLGLVVCLVLWTLHSEG (SEQ ID NO: 2) |
| Full Length Precursor | MKMRFLGLVVCLVLWTLHSEGSGGKLTAVDPETNMNVSEIISYWGFPSEEYLVETE DGYILCLNRIPHGRKNHSDKGPKPVVFLQHGLLADSSNWVTNLANSSLGFILADAG FDVWMGNSRGNTWSRKHKTLSVSQDEFWAFSYDEMAKYDLPASINFILNKTGQEQV YYVGHSQGTTIGFIAFSQIPELAKRIKMFFALGPVASVAFCTSPMAKLGRLPDHLI KDLFGDKEFLPQSAFLKWLGTHVCTHVILKELCGNLCFLLCGFNERNLNMSRVDVY TTHSPAGTSVQNMLHWSQAVKFQKFQAFDWGSSAKNYFHYNQSYPPTYNVKDMLVPT AVWSGGHDWLADVYDVNILLTQITNLVFHESIPEWEHLDFIWGLDAPWRLYNKIINL MRKYQ (SEQ ID NO: 3) | adrenal gland and intestine. Affected rats typically die without reproducing at about 120 days of age.

Biological characterization of the Yoshida rat LALD model has been performed (see, for example, Kuriyama et al. *Journal of Lipid Research* 31:1695; 1990, the entire contents of which is incorporated herein by reference). Affected rats accumulated cholesteryl esters (e.g., 13.3 fold and 2.5 fold in the liver and spleen, respectively), free cholesterol (e.g., 2.8 fold and 1.33 fold in the liver and spleen, respectively) and triglycerides (e.g., 5.4 fold in the liver) in various tissues. Affected rats showed high percentages of linoleic acid (e.g., 18:2) and arachidonic acid (e.g., 20:4) in both the liver and spleen.

As described in the Examples section, the present inventors found that administering a recombinant human lysosomal acid lipase (rhLAL) to Yoshida rats successfully treated various Wolman's disease or CESD-like symptoms resulting in improved gross liver, spleen and intestine pathology, significantly reduced lipid accumulation in various tissues, and particularly surprisingly, substantial improvement in body growth and weight gain. Indeed, treated animals exhibited weight gain with a weekly percent body weight gain comparable to wild type animals. Therefore, among other things, the present inventors demonstrated that developmental failure or cachexia, this most devastating symptom in Wolman's disease, can be effectively treated using a recombinant lysosomal acid lipase.

Lysosomal Acid Lipase

A lysosomal acid lipase enzyme suitable for the present invention includes any enzyme that is capable of reducing Natural variants of human lysosomal acid lipase polypeptides are known. For example, in some embodiments, residues 1-56 of SEQ ID NO:3, corresponding to residues 1-35 of SEQ ID NO:1, are deleted. In some embodiments, residues 57-76 of SEQ ID NO:3 (DGYILCLNRIPHGRKNHSDK), corresponding to residues 36-55 of SEQ ID NO:1, are replaced with MACLEFVPFDVQMCLEFLPS (SEQ ID NO:4). In some embodiments, residue 16 of SEQ ID NO:3 has a Thr to Pro substitution. In some embodiments, residue 23 of SEQ ID NO:3, corresponding to residue 2 of SEQ ID NO:1, has a Gly to Arg substitution. In some embodiments, residue 29 of SEQ ID NO:3, corresponding to residue 8 of SEQ ID NO:1, has a Val to Leu substitution. In some embodiments, residue 228 of SEQ ID NO:3, corresponding to residue 207 of SEQ ID NO:1, has a Phe to Ser substitution.

In some embodiments, a lysosomal acid lipase enzyme suitable for the present invention is substantially homologous to SEQ ID NO:1. In some embodiments, a suitable lysosomal acid lipase enzyme has a sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1.

In some embodiments, a lysosomal acid lipase enzyme suitable for the present invention is substantially identical to SEQ ID NO:1. In some embodiments, a suitable lysosomal acid lipase enzyme has a sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1.

In some embodiments, a lysosomal acid lipase enzyme suitable for the present invention is a fragment of human LAL or a fusion protein containing a lysosomal acid lipase such as human LAL, or a portion thereof A lysosomal acid lipase suitable for the present invention may be produced by any available means. For example, lysosomal acid lipase enzymes may be recombinantly produced by utilizing a host cell system engineered to express an LAL polypeptide-encoding nucleic acid. Alternatively or additionally, lysosomal acid lipase enzymes may be partially or fully prepared by chemical synthesis. Alternatively or additionally, lysosomal acid lipase enzymes may also be purified from natural sources.

Where lysosomal acid lipase enzymes are recombinantly produced, any expression system can be used. To give but a few examples, known expression systems include, for example, egg, baculovirus, plant, yeast, or mammalian cells.

In some embodiments, lysosomal acid lipase enzymes suitable for the present invention are produced in mammalian cells. Non-limiting examples of mammalian cells that may be used in accordance with the present invention include BALB/c mouse myeloma line (NSO/l, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59,1977); human fibrosarcoma cell line (HT1080); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, lysosomal acid lipase enzymes suitable for the present invention are produced in avian expression systems, e.g. in eggs of chimeric chickens. Exemplary methodologies for expressing proteins, including lysosomal acid lipases, in avian expression systems are described in PCT Publication WO 2004/015123 and U.S. Pub. Nos. 20060191026, 20090178147; 20090180989; 20100083389; and 2010033219, the entire contents of each of which are incorporated herein by reference.

In some embodiments, lysosomal acid lipase enzymes suitable for the present invention are produced in plant expression systems, e.g. in tobacco plants or related species (e.g., Nicotiana species). In some embodiments, lysosomal acid lipase enzymes are expressed in Nicotiana benthamiana. Exemplary methodologies for expressing proteins, including lysosomal acid lipases, in plant expression systems are known in the art. For example, GENEWARE® technology utilizes a modified tobacco mosaic virus vector to express heterologous proteins within a tobacco plant. Expressed proteins may subsequently be isolated and/or purified.

In some embodiments, lysosomal acid lipase enzymes suitable for the present invention are produced in yeast expression systems, e.g. in methylotropic yeast. In some embodiments, lysosomal acid lipase enzymes are expressed in *Pichia pastoris*. Exemplary methodologies for expressing proteins, including lysosomal acid lipases, in yeast expression systems are known in the art (see, for example, Daly, et al. J Mol Recognit. 18:119 (2005), the contents of which is incorporated herein by reference).

It will be appreciated that other expression systems are known in the art and can be used to produce lysosomal acid lipase enzymes described herein.

In some embodiments, lysosomal acid lipase enzymes produced by a suitable expression system may have similar or identical glycosylation level or pattern to that of a naturally-occurring human LAL. In some embodiments, lysosomal acid lipase enzymes produced by a suitable expression system may have increased or decreased glycosylation level or altered glycosylation pattern as compared to a naturally-occurring human LAL. For example, lysosomal acid lipases may be produced using transgene-augmented glycosylation avians as described in U.S. Pub. No. 20090178147, the disclosure of which is incorporated herein by reference. In some embodiments, lysosomal acid lipases suitable for the present invention may contain particular glycosylation pattern such as various N-glycan structures as described in WO 2011133960, the disclosure of which is incorporated herein by reference in its entirety.

In some embodiments, suitable lysosomal acid lipase enzymes may be post-translationally modified to alter the glycosylation level or pattern of the enzyme. For example, a lysosomal acid lipase enzyme may be modified to increase or decrease glycosylation levels. In some embodiments, a lysosomal acid lipase enzyme may be de-glycosylated.

Treatment of LAL Deficiency

Methods of the present invention may be used to effectively treat individuals suffering from or susceptible to LALD diseases, in particular, those individuals affected by Wolman's disease or cholesteryl ester storage disease (CESD). The terms, "treat" or "treatment," as used herein, refers to amelioration of one or more symptoms associated with the disease, prevention or delay of the onset of one or more symptoms of the disease, and/or lessening of the severity or frequency of one or more symptoms of the disease.

In some embodiments, treatment refers to partially or completely alleviation, amelioration, relief, inhibition, delaying onset, reducing severity and/or incidence of developmental impairment in an LALD patient. As used herein, the term "developmental impairment" includes various symptoms associated with malnutrition, or growth failure in a patient suffering from a LALD disease including, but not limited to, development delay, poor weight gain or weight loss, weakness or wasting of various tissues (muscle, subcutaneous tissues, etc). Developmental impairment is typically associated with frequent vomiting, diarrhea, or abdominal distension. Developmental impairment is also referred to as malnutrition, cachexia or failure to thrive. As used herein, developmental impairment encompasses symptoms of both Wolman's disease and CESD.

Thus, in some embodiments, treatment refers to improved body weight gain (e.g., total weight gain, percent body weight gain per week, per month, per two months, per six months, etc.). In certain embodiments, total body weight gain is, on average, about 0.1 kg, about 0.2 kg, about 0.3 kg, about 0.4 kg, about 0.5 kg, about 0.6 kg, about 0.7 kg, about 0.8 kg, about 0.9 kg, about 1 kg, about 1.1 kg, about 1.2 kg, about 1.3 kg, about 1.4 kg, about 1.5 kg, about 1.6 kg, about 1.7 kg, about 1.8 kg, about 1.9 kg, about 2 kg, about 2.1 kg, about 2.2 kg, about 2.3 kg, about 2.4 kg, about 2.5 kg, about 2.6 kg, about 2.7 kg, about 2.8 kg, about 2.9 kg, about 3 kg, or more, per week. In some embodiments, percent body weight gain is an increase by, on average, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or more per week. As used herein, percent body weight gain is determined by comparing the total body weight gain to the base total body weight before the gain. In some embodiments, treatment results in normal total body weight gain or percent body weight gain in the LALD patient. As used herein, normal total body weight gain or percent body weight gain refers to an average total body weight gain or an average percent body weight gain for an average healthy individual at the same development stage (e.g., same age, same gender) as the LALD patient.

In some embodiments, treatment refers to reduced or prevented weight loss (e.g., total weight loss, percent body weight loss per week, per month, per two months, per six months, etc.). In some embodiments, total body weight loss is, on average, less than about 0.1 kg, about 0.2 kg, about 0.3 kg, about 0.4 kg, about 0.5 kg, about 0.6 kg, about 0.7 kg, about 0.8 kg, about 0.9 kg, about 1 kg, about 1.1 kg, about 1.2 kg, about 1.3 kg, about 1.4 kg, about 1.5 kg, about 1.6 kg, about 1.7 kg, about 1.8 kg, about 1.9 kg, about 2 kg, about 2.1 kg, about 2.2 kg, about 2.3 kg, about 2.4 kg, about 2.5 kg, about 2.6 kg, about 2.7 kg, about 2.8 kg, about 2.9 kg, or about 3 kg per week. In some embodiments, percent body loss is, on average, less than about 0.1%, about 0.5%, about 1%, about 1.5%, about 2%, about 2.5%, about 3%, about 3.5%, about 4%, about 5%, about 10%, about 15%, about 20%, or about 25% per week. As used herein, percent body weight loss is determined by comparing the total body weight loss to the base total body weight before the loss.

In some embodiments, treatment refers to reduced or eliminated tissue weakness or wasting (e.g., weakness or wasting in muscle and/or subcutaneous tissues). In some embodiments, treatment refers to reduced frequency of vomiting and/or diarrhea.

In some embodiments, treatment refers to reduction of accumulation of fatty material (e.g., lipids such as cholesterol and/or triglycerides) in various tissues (e.g., liver, spleen, gut, blood vessel walls, bone marrow, adrenal glands (small hormone-producing glands on top of each kidney), and lymph nodes, etc.). In some embodiments, treatment results in a reduction of lipid accumulation by more than 10%, more than 20%, more than 30%, more than 40%, more then 50%, more than 60%, more than 70%, more than 80%, more than 90%, more than 95%, or more. In some embodiments, treatment results in substantial elimination of lipid accumulation in various tissues (e.g., liver, spleen, gut, blood vessel walls, bone marrow, adrenal glands (small hormone-producing glands on top of each kidney), and lymph nodes, etc.).

In some embodiments, treatment refers to improved gross tissue pathology in various tissues (e.g., liver, spleen, small intestines). For example, treatment can result in decreased relative tissue (e.g., liver, spleen, small intestine) weight and/or volume to total body weight. In some embodiments, treatment refers to reduced relative tissue (e.g., liver, spleen, small intestine) weight and/or volume to total body by at least 10%, 20%, 30%, 40%, 50%, 60%, 70%, 80%, 90%, or 95% as compared to the pre-treatment state. In some embodiments, treatment according to the present invention results in a relative tissue (e.g., liver, spleen, small intestine) weight and/or volume similar to that of an healthy individual at the same developmental stage (e.g., same age and gender).

It will be appreciated that tissue analyses, e.g., fat content and/or gross tissue pathology, and/or relative tissue weight or volume may be determined by any appropriate method available in the art and/or described herein. For example, in some embodiments, tissue pathology and relative weight/volume is analyzed by magnetic resonance imaging (MRI) and/or magnetic resonance spectroscopy (MRS). E.g., see d'Assignies et al. *Magnetic Resonance* 21:301 2011, the contents of which are incorporated herein by reference. d'Assignies and colleagues demonstrated simultaneous assessment of liver volume and whole liver fat content in patients by MRI/MRS. Additional tissue analysis methods include, but are not limited to, computed tomography (CT), tissue biopsy, biochemical tests of tissue function, ultrasound, Xenon clearance rates, or combinations thereof. Thus, in some embodiments, treatment refers to improved gross tissue pathology, morphology, relative tissue weight or volume, or fat content as determined by one or more methods described herein or known in the art.

In some embodiments, treatment refers to reduction of fatty material (e.g., lipids such as cholesterol and/or triglycerides) in serum. In some embodiments, treatment results in a reduction of lipid in serum by more than 10%, more than 20%, more than 30%, more than 40%, more then 50%, more than 60%, more than 70%, more than 80%, more than 90%, more than 95%, or more, as compared to the pre-treatment level. In some embodiments, treatment according to the present invention results in a serum fatty material (e.g., lipids such as cholesterol and/or triglycerides) level similar to that of an healthy individual at the same developmental stage (e.g., same age and gender).

In some embodiments, treatment refers to improvement of tissue function (e.g., liver, heart, muscle, kidney, etc.) as determined by the presence and/or amounts or activities of certain enzymes in the blood. For example, tissue function may be measured by the presence and/or amounts of aspartate aminotransferase (AST) (also known as serum glutamic oxaloacetic transaminase (SGOT)) and/or alanine aminotransferase (ALT) (also known as serum glutamic pyruvic transaminase (SGPT)). AST is normally found in liver, heart, muscle, kidney, and brain, and is typically released into serum when any one of these tissue is damaged. ALT is normally found largely in the liver, although it can be found in other tissues in smaller amounts. ALT is typically released into the serum as a result of liver injury and serves as a fairly specific indicator of liver status. Other enzymes indicative of various tissue (e.g., liver, heart, muscle, kidney, etc.) function are known in the art and can be used to monitor the treatment efficacy according to the present invention.

In some embodiments, treatment refers to increased survival (e.g. survival time). For example, treatment can result in an increased life expectancy of a patient. In some embodiments, treatment according to the present invention results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with similar disease form without treatment. In some embodiments, treatment according to the present invention results in an increased life expectancy of a patient by more than about 1 month, about 2 months, about 3 months, about 4 months, about 5 months, about 6 months, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with similar disease form without treatment. In some embodiments, treatment according to the present invention results in long term survival of a patient, in particular, a patient suffering from Wolman's disease. As used herein, the term "long term survival" refers to a survival time or life expectancy longer than about 10 years, 15 years, 20 years, 25 years, 30 years or longer.

The terms, "improve," "increase" or "reduce," as used herein, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal acid lipase deficiency (LALD) disease (either early-onset (e.g., Wolman's disease) or later-onset (e.g., cholesteryl ester storage disease (CESD)) as the individual being treated, who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having lysosomal acid lipase deficiency (LALD) disease (either early-onset (e.g., Wolman's disease) or later-onset (e.g., cholesteryl ester storage disease (CESD)) or having the potential to develop lysosomal acid lipase deficiency (LALD) disease. The individual can have residual endogenous lysosomal acid lipase (LAL) activity, or no measurable activity. For example, the individual having lysosomal acid lipase deficiency (LALD) disease can have LAL activity that is less than about 1% of normal LAL activity (i.e., LAL activity that is usually associated with early-onset Wolman's disease), or LAL activity that is about 1-10% of normal LAL activity (i.e., LAL activity that is usually associated with later-onset cholesteryl ester storage disease (CESD)).

In some embodiments, the individual is an individual who has been recently diagnosed with the disease. Typically, early treatment (treatment commencing as soon as possible after diagnosis) is important to minimize the effects of the disease and to maximize the benefits of treatment.

Administration of Lysosomal Acid Lipase

In the methods of the invention, the Lysosomal Acid Lipase (LAL) is typically administered to the individual alone, or in compositions or medicaments comprising the Lysosomal Acid Lipase (LAL) (e.g., in the manufacture of a medicament for the treatment of the disease), as described herein. The compositions can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In some embodiments, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

The Lysosomal Acid Lipase (LAL) can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Lysosomal Acid Lipase (LAL) (or a composition or medicament containing Lysosomal Acid Lipase (LAL)) is administered by any appropriate route. In some embodiments, Lysosomal Acid Lipase (LAL) is administered intravenously. In some embodiments, Lysosomal Acid Lipase (LAL) is administered subcutaneously. In some embodiments, Lysosomal Acid Lipase (LAL) is administered by direct administration to a target tissue, such as heart or muscle (e.g., intramuscular), or nervous system (e.g., direct injection into the brain; intraventricularly; intrathecally). Alternatively, Lysosomal Acid Lipase (LAL) (or a composition or medicament containing Lysosomal Acid Lipase (LAL)) can be administered parenterally, transdermally, or transmucosally (e.g., orally or nasally). More than one route can be used concurrently, if desired.

Lysosomal Acid Lipase (LAL) (or composition or medicament containing Lysosomal Acid Lipase (LAL)) can be administered alone, or in conjunction with other agents, such as antihistamines (e.g., diphenhydramine) or immunosuppressants or other immunotherapeutic agents which counteract anti-Lysosomal Acid Lipase (LAL) antibodies. The term, "in conjunction with," indicates that the agent is administered prior to, at about the same time as, or following the Lysosomal Acid Lipase (LAL) (or composition containing Lysosomal Acid Lipase (LAL)). For example, the agent can be mixed into a composition containing Lysosomal Acid Lipase (LAL), and thereby administered contemporaneously with the Lysosomal Acid Lipase (LAL); alternatively, the agent can be administered contemporaneously, without mixing (e.g., by "piggybacking" delivery of the agent on the intravenous line by which the Lysosomal Acid Lipase (LAL) is also administered, or vice versa). In another example, the agent can be administered separately (e.g., not admixed), but within a short time frame (e.g., within 24 hours) of administration of the Lysosomal Acid Lipase (LAL). In some embodiments, Lysosomal Acid Lipase (LAL) (or composition containing Lysosomal Acid Lipase (LAL)) is administered in conjunction with an immunosuppressive or immunotherapeutic regimen designed to reduce amounts of, or prevent production of, anti-Lysosomal Acid Lipase (LAL) antibodies. For example, a protocol similar to those used in hemophilia patients (Nilsson et al. (1988) *N. Engl. J. Med.*, 318:947-50) can be used to reduce anti-Lysosomal Acid Lipase (LAL) antibodies. Such a regimen can be used in individuals who have, or are at risk of having, anti-Lysosomal Acid Lipase (LAL) antibodies. In some embodiments, the immunosuppressive or immunotherapeutic regimen is begun prior to the first administration of Lysosomal Acid Lipase (LAL), in order to minimize the possibility of production of anti-Lysosomal Acid Lipase (LAL) antibodies.

Lysosomal Acid Lipase (LAL) (or composition or medicament containing Lysosomal Acid Lipase (LAL)) is administered in a therapeutically effective amount (i.e., a dosage amount that, when administered at regular intervals, is sufficient to treat the disease, such as by ameliorating symptoms associated with the disease, preventing or delaying the onset of the disease, and/or also lessening the severity or frequency of symptoms of the disease, as described above). As used herein, the therapeutic effective amount is also referred to as therapeutic effective dose or therapeutic effective dosage amount. The dose which will be therapeutically effective for the treatment of the disease will depend on the nature and extent of the disease's effects, and can be determined by standard clinical techniques. In addition, in vitro or in vivo assays may optionally be employed to help identify optimal dosage ranges, such as those exemplified below. The precise dose to be employed will also depend on the route of administration, and the seriousness of the disease, and should be decided according to the judgment of a practitioner and each patient's circumstances. For example, in some embodiments, a therapeutically effective amount of Lysosomal Acid Lipase (LAL) for subcutaneous administration is about 1.5-fold, about 2-fold, about 2.5-fold, about 2.5-fold, about 3-fold, about 3.5-fold, about 4-fold, about 4.5-fold, about 5-fold, about 5.5-fold, about 6-fold, about 6.5-fold, about 7-fold, about 7.5-fold, about 8-fold, about 8.5-fold, about 9-fold, about 9.5-fold, about 10-fold or more than a therapeutically effective amount of Lysosomal Acid Lipase (LAL) for intravenous administration. Effective doses may be extrapolated from dose-response curves derived from in vitro or animal model test systems (e.g., as described by the U.S. Department of Health and Human Services, Food and Drug Administration, and Center for Drug Evaluation and Research in "Guidance for Industry: Estimating Maximum Safe Starting Dose in Initial Clinical Trials for Therapeutics in Adult Healthy Volunteers", *Pharmacology and Toxicology*, July 2005, the entire contents of which are incorporated herein by reference).

In some embodiments, the therapeutically effective amount can be, for example, more than about 0.01 mg/kg, more than about 0.05 mg/kg, more than about 0.1 mg/kg, more than about 0.5 mg/kg, more than about 1.0 mg/kg, more than about 1.5 mg/kg, more than about 2.0 mg/kg, more than about 2.5 mg/kg, more than about 5.0 mg/kg, more than about 7.5 mg/kg, more than about 10 mg/kg, more than about 12.5 mg/kg, more than about 15 mg/kg, more than about 17.5 mg/kg, more than about 20 mg/kg, more than about 22.5 mg/kg, or more than about 25 mg/kg body weight. In some embodiments, a therapeutically effective amount can be about 0.01-25 mg/kg, about 0.01-20 mg/kg, about 0.01-15 mg/kg, about 0.01-10 mg/kg, about 0.01-7.5 mg/kg, about 0.01-5 mg/kg, about 0.01-4 mg/kg, about 0.01-3 mg/kg, about 0.01-2 mg/kg, about 0.01-1.5 mg/kg, about 0.01-1.0 mg/kg, about 0.01-0.5 mg/kg, about 0.01-0.1 mg/kg, about 1-20 mg/kg, about 4-20 mg/kg, about 5-15 mg/kg, about 5-10 mg/kg body weight. In some embodiments, a therapeutically effective amount is about 0.01 mg/kg, about 0.05 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg about 1.4 mg/kg, about 1.5 mg/kg, about 1.6 mg/kg, about 1.7 mg/kg, about 1.8 mg/kg, about 1.9 mg/kg, about 2.0 mg/kg, about 2.5 mg/kg, about 3.0 mg/kg, about 4.0 mg/kg, about 5.0 mg/kg, about 6.0 mg/kg, about 7.0 mg/kg, about 8.0 mg/kg, about 9.0 mg/kg, about 10.0 mg/kg, about 11.0 mg/kg, about 12.0 mg/kg, about 13.0 mg/kg, about 14.0 mg/kg, about 15.0 mg/kg, about 16.0 mg/kg, about 17.0 mg/kg, about 18.0 mg/kg, about 19.0 mg/kg, about 20.0 mg/kg, body weight, or more. In some embodiments, the therapeutically effective amount is no greater than about 30 mg/kg, no greater than about 20 mg/kg, no greater than about 15 mg/kg, no greater than about 10 mg/kg, no greater than about 7.5 mg/kg, no greater than about 5 mg/kg, no greater than about 4 mg/kg, no greater than about 3 mg/kg, no greater than about 2 mg/kg, or no greater than about 1 mg/kg body weight or less.

The effective dose for a particular individual can be varied (e.g., increased or decreased) over time, depending on the needs of the individual. For example, in times of physical illness or stress, or if anti-Lysosomal Acid Lipase (LAL) antibodies become present or increase, or if disease symptoms worsen, the dosage amount can be increased.

In yet another example, a loading dose (e.g., an initial higher dose) of a therapeutic composition may be given at the beginning of a course of treatment, followed by administration of a decreased maintenance dose (e.g., a subsequent lower dose) of the therapeutic composition. Without wishing to be bound by any theories, it is contemplated that a loading dose clears out the initial and, typically massive, accumulation of fatty materials in tissues (e.g., in the liver), and maintenance dosing prevents buildup of fatty materials after initial clearance.

It will be appreciated that a loading dose and maintenance dose amounts, intervals, and duration of treatment may be determined by any available method, such as those exemplified herein and those known in the art. In some embodiments, a loading dose amount is about 0.01-1 mg/kg, about 0.01-5 mg/kg, about 0.01-10 mg/kg, about 0.1-10 mg/kg, about 0.1-20 mg/kg, about 0.1-25 mg/kg, about 0.1-30 mg/kg, about 0.1-5 mg/kg, about 0.1-2 mg/kg, about 0.1-1 mg/kg, or about 0.1-0.5 mg/kg body weight. In some embodiments, a maintenance dose amount is about 0-10 mg/kg, about 0-5 mg/kg, about 0-2 mg/kg, about 0-1 mg/kg, about 0-0.5 mg/kg, about 0-0.4 mg/kg, about 0-0.3 mg/kg, about 0-0.2 mg/kg, about 0-0.1 mg/kg body weight. In some embodiments, a loading dose is administered to an individual at regular intervals for a given period of time (e.g., 1, 2, 3, 4, 5, 6, 7, 8, 9, 10, 11, 12 or more months) and/or a given number of doses (e.g., 1, 2, 3, 4, 5, 6, 7, 8, 9, 10, 15, 20, 25, 30 or more doses), followed by maintenance dosing. In some embodiments, a maintenance dose ranges from 0-2 mg/kg, about 0-1.5 mg/kg, about 0-1.0 mg/kg, about 0-0.75 mg/kg, about 0-0.5 mg/kg, about 0-0.4 mg/kg, about 0-0.3 mg/kg, about 0-0.2 mg/kg, or about 0-0.1 mg/kg body weight. In some embodiments, a maintenance dose is about 0.01, 0.02, 0.04, 0.06, 0.08, 0.1, 0.2, 0.3, 0.4, 0.5, 0.6, 0.7, 0.8, 0.9, 1.0, 1.2, 1.4, 1.6, 1.8, or 2.0 mg/kg body weight. In some embodiments, maintenance dosing is administered for 1, 2, 3, 4, 5, 6, 7, 8, 9, 10, 11, 12 or more months. In some embodiments, maintenance dosing is administered for 1, 2, 3, 4, 5, 6, 7, 8, 9, 10 or more years. In some embodiments, maintenance dosing is administered indefinitely (e.g., for life time).

A therapeutically effective amount of Lysosomal Acid Lipase (LAL) (or composition or medicament containing Lysosomal Acid Lipase (LAL)) is administered at regular intervals, depending on the nature and extent of the disease's effects, and on an ongoing basis. Administration at an "interval," as used herein, indicates that the therapeutically effective amount is administered periodically (as distinguished from a one-time dose). The interval can be determined by standard clinical techniques. In some embodiments, Lysosomal Acid Lipase (LAL) is administered bimonthly, monthly, twice monthly, triweekly, biweekly, weekly, twice weekly, thrice weekly, or daily. The administration interval for a single individual need not be a fixed interval, but can be varied over time, depending on the needs of the individual. For example, in times of physical illness or stress, if anti-Lysosomal Acid Lipase (LAL) antibodies become present or increase, or if disease symptoms worsen, the interval between doses can be decreased.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

The invention additionally pertains to a pharmaceutical composition comprising human Lysosomal Acid Lipase (LAL), as described herein, in a container (e.g., a vial, bottle, bag for intravenous administration, syringe, etc.) with a label containing instructions for administration of the composition for treatment of Lysosomal Acid Lipase Deficiency (LALD) disease (e.g., Wolman's disease or CESD), such as by the methods described herein.

The invention will be further and more specifically described by the following examples. Examples, however, are included for illustration purposes, not for limitation.

EXAMPLES

Example 1

Production of Recombinant Human Lysosomal Acid Lipase (rhLAL)

Experiments described in this example show that recombinant LAL can be expressed and purified from mammalian cells.

Specifically, cultured human cells were transfected with a plasmid containing human Lysosomal Acid Lipase open reading frame by electroporation and cloned by limiting dilution. Stable clones were selected using cloning media containing 0.4 mg/mL G418. Clones were expanded and rhLAL expression and activity was analyzed using ELISA and LAL activity assays.

In total, 384 clones were analyzed for rhLAL expression and activity. Clone 35 was determined to have the highest and most stable rhLAL expression. Expression in shake flasks was 3-4 pcd on average and expression in wave reactor was 4-6 pcd on average. Clone 35 was expanded and a cell bank was prepared.

Clone 35 was seeded into 5 mL Wave cultures in 10 L wave bags. Wave bags were perfused at 5 L per day and conditioned media (CM) were harvested, filtered and stored at 4° C. for up to 7 days, until concentration by ultra-filtration. CM was concentrated using 10 kDa MWCO UF/DF concentrator and stored at −20° C. for 10-40 days until processed. Prior to purification, concentrated CM was thawed and the conductivity was increased by the addition of NaCl to a final concentration of 200 mM. Purification involved butyl-Sepharose 4 FF column capture followed by a polishing step with Q Sepharose FF column. Purified rhLAL was dialyzed against the final storage buffer, PBS pH=6.5, sterile filtered and stored at −80° C.

Certain characteristics of the rhLAL protein were determined The DNA coding sequence predicts the molecular weight to be 43 kDa. Purified rhLAL was subjected to denaturing SDS-PAGE Western and Coomassie, and native size exclusion chromatography. Post translational modifications of rhLAL were determined by glycodigestion followed by SDS-PAGE Western or native isoelectric focusing (IEF).

Figure 2:
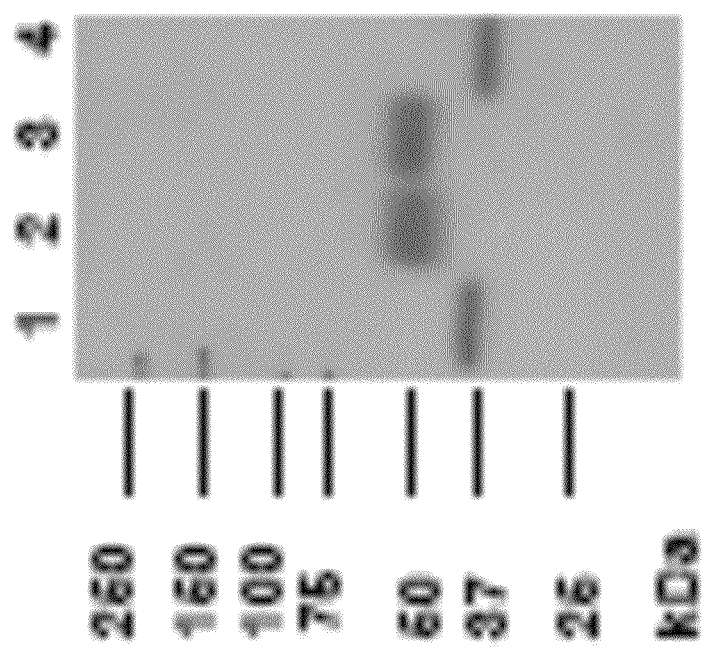
FIG. 2 depicts exemplary deglycosylation by PNGase. rhLAL was incubated with (lanes 1 and 4) or without PNGase F (lanes 2 and 3) for 1 hour (lanes 1 and 2) or overnight (lanes 3 and 4).

As shown in FIG. 1, rhLAL was analyzed by denaturing SDS-PAGE and visualized by Coomassie stain and compared to BSA. Lanes 1-3 contained 1, 2.5, and 5 ug of BSA, respectively. Lanes 4-6 contained 1, 2.5 and 5 ug of purified rhLAL, respectively. Protein molecular weight markers are labeled on the left. Purified rhLAL demonstrated an apparent molecular weight of ~54.5 kDa. Human LAL protein has 6 potential N glycosylation sites based on its primary amino acid sequence. Deglycosylation of purified rhLAL by incubation with PNGase F led to a decrease in molecular weight of the protein to ~42 kDa compared to untreated protein with a molecular weight of ~50kDa (FIG. 2). These studies indicated the presence of carbohydrates on the protein backbone of purified rhLAL.

Example 2

Treatment of LAL Deficient Yoshida Rats Using rhLAL

Experiments described in this example are designed to show that rhLAL can effectively treat LALD diseases, such as Wolman's disease and Cholesteryl Ester Storage Disease (CESD). The Yoshida (LAL deficient) rat was used as animal model.

As described above, the Yoshida (LAL deficient) rat is a naturally occurring animal model of LALD disease (Yoshida and Kuriyama, *Laboratory Animal Science* 40(5) 1990). Affected rats inherit the disease in an autosomal recessive manner and the disease is characterized by developmental impairment and/or failure, hepatosplenomegaly, lymph node enlargement, and thickened dilated intestine. Many characteristic foam cells are observed in livers and spleens of affected mice. Typically, Kupffer cell, which is macrophage, becomes "foam cell" with lipid accumulation. Massive intracellular storage of both cholesteryl esters and triglycerides are observed in the liver, adrenal gland and intestine. Affected rats typically die without reproducing at about 120 days of age, which is approximately one sixth the typical life span of a normal rat.

Figure 3:
FIG. 3 depicts an exemplary size comparison of wild-type and LAL deficient Yoshida rats at 6 weeks of age.
Figure 4:
FIG. 4 depicts an exemplary size comparison of wild-type and LAL deficient Yoshida rats at 13 weeks of age.

First, in-life evaluations, such as general health, weekly body weights, and serum chemistry of wild-type and homozygous LAL deficient rats were performed. As shown in FIGS. 3 and 4, a homozygous LAL deficient rat had much smaller body weight as compared with a wild-type rat at 6 and 13 weeks of age, respectively. Body weight comparisons of wild-type and LAL deficient rats are shown in FIG. 5. FIGS. 5A and 5B depict weight gain in male and female rats respectively. Homozygous LAL deficient rats also showed progression of abdominal distension as shown in FIGS. 6A and 6B. Taken together, these data indicate that the Yoshida rat used in this experiment manifested developmental impairment or cachexia such as poor development progress and weight gain, symptoms characteristic of LALD disease, in particular, Wolman's disease.

Figure 7:
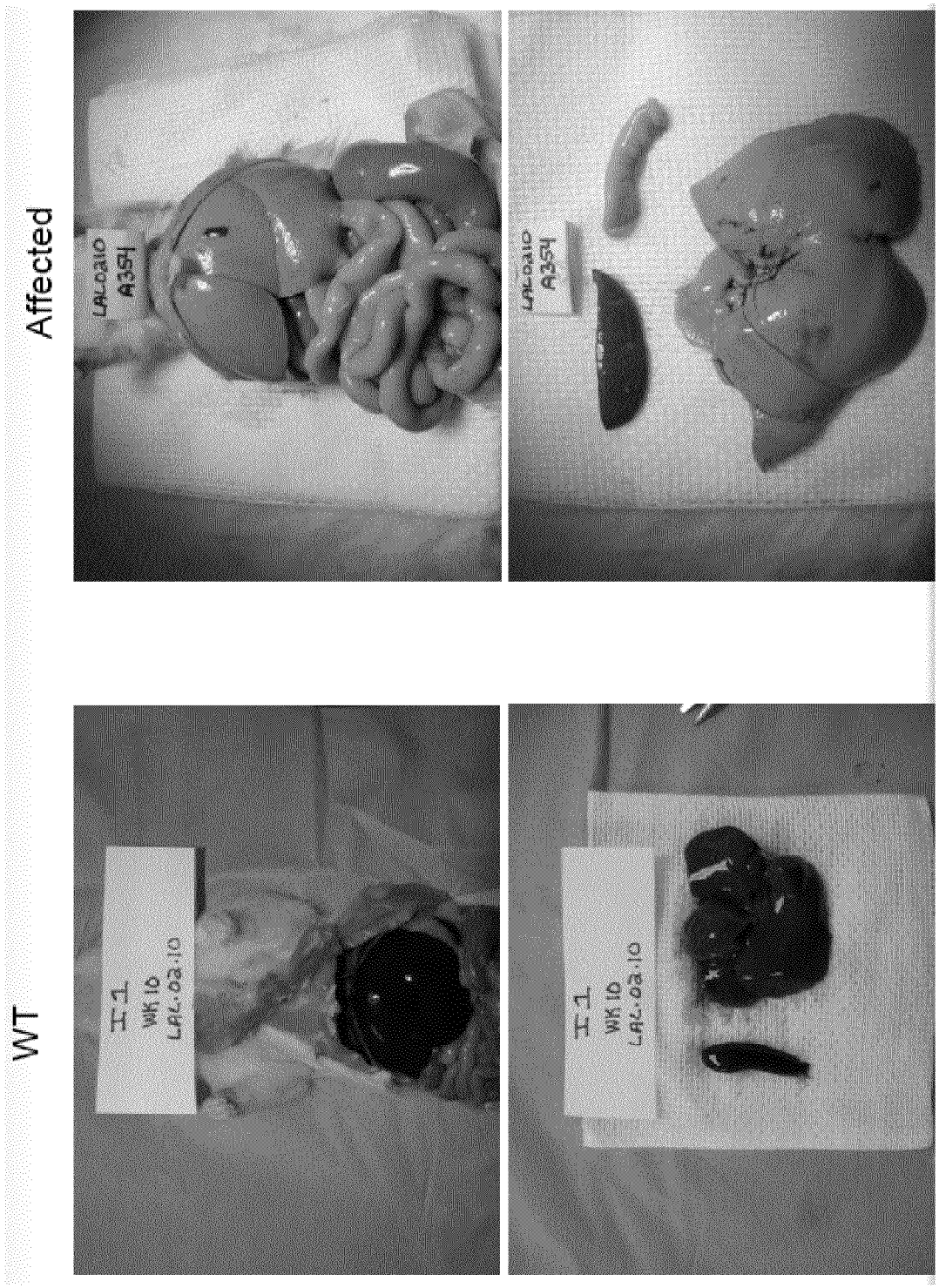
FIG. 7 depicts an exemplary liver and spleen size comparison of wild-type and LAL deficient Yoshida rats at 14 weeks of age.
Figure 8:
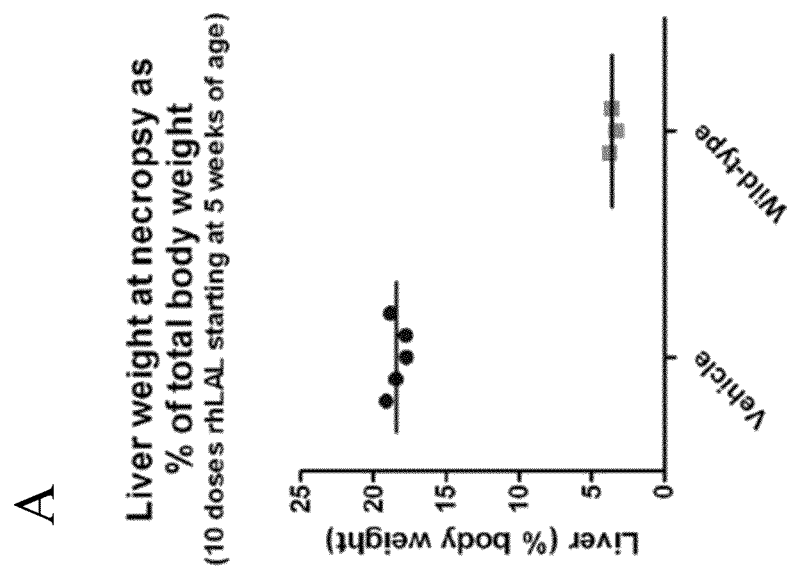
FIG. 8 depicts an exemplary liver and spleen weight comparison of wild-type and LAL deficient Yoshida rats.
Figure 9:
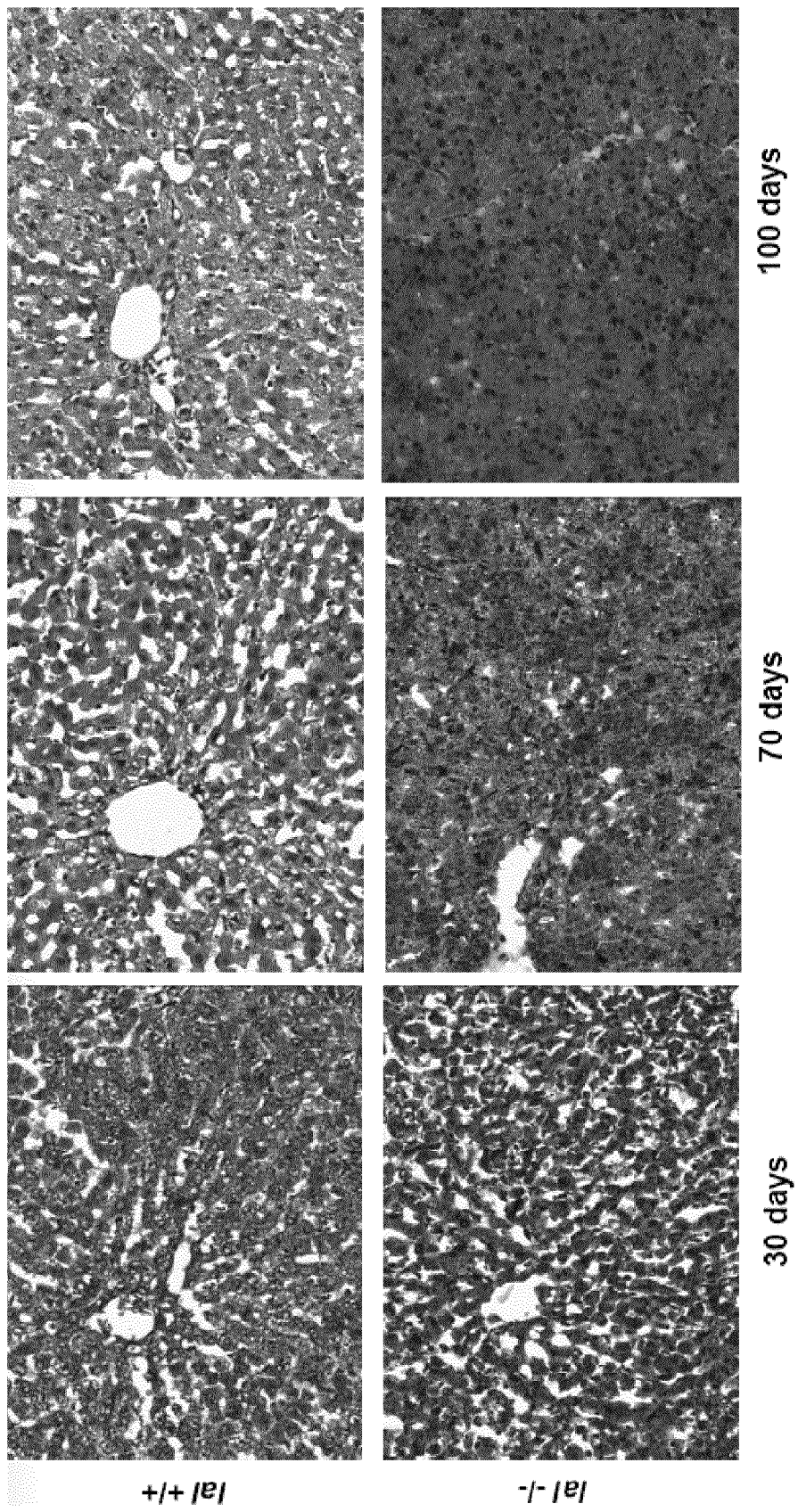
FIG. 9 depicts exemplary lipid accumulation in liver of LAL deficient Yoshida rats. Oil Red O staining showed large cellular accumulations of neutral lipid (red deposits) in the livers of LAL deficient Yoshida rats compared with wild-type animals. The lipid accumulation was age-dependent with marked lipid storage throughout the livers at 100 days. Images are 20×.
Figure 10:
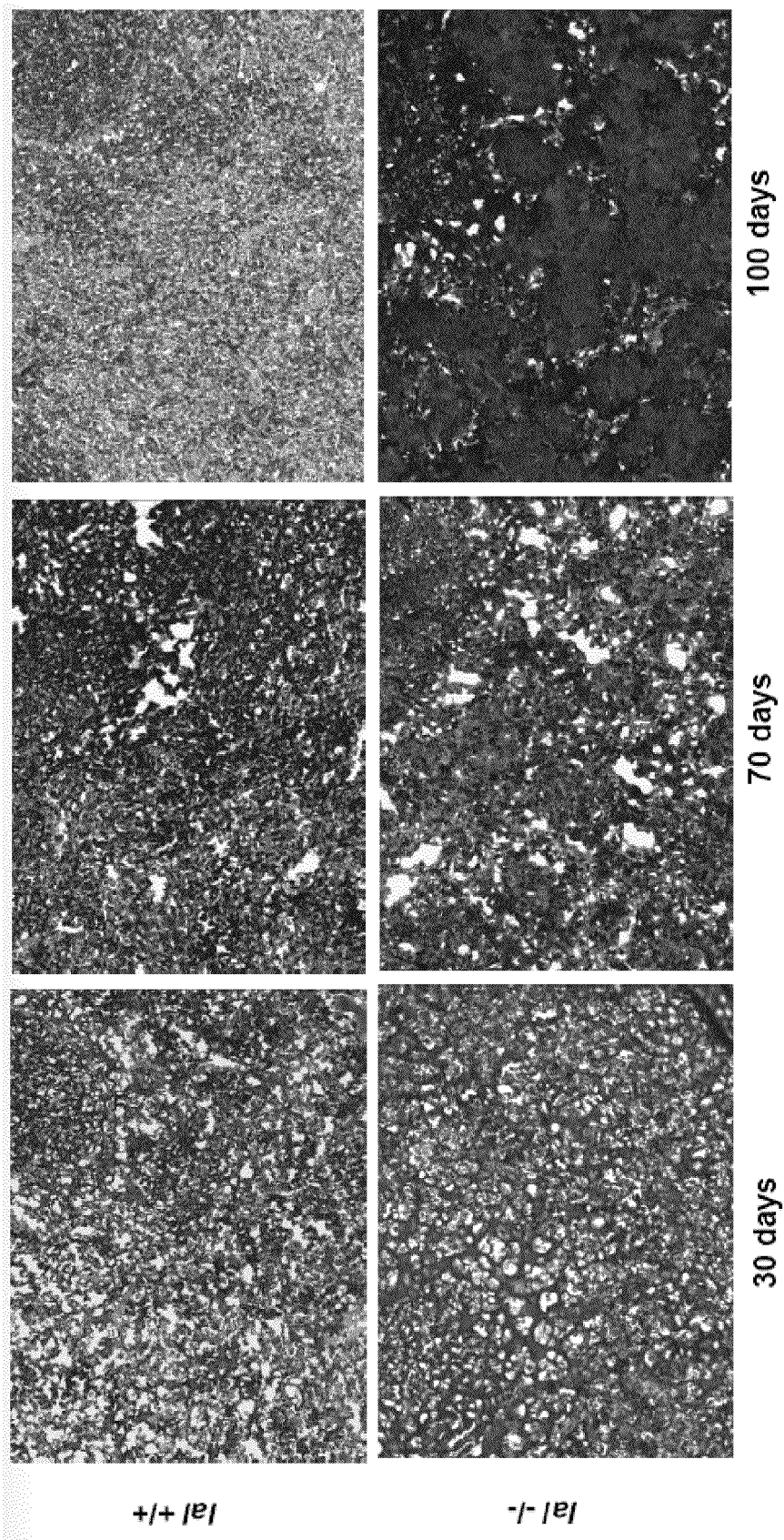
FIG. 10 depicts exemplary lipid accumulation in spleen of LAL deficient Yoshida rats. Oil Red O staining showed large cellular accumulations of neutral lipids in the spleens of LAL deficient Yoshida rats compared with wild-type animals. The lipid accumulation was age-dependent with marked lipid storage throughout the spleens at 100 days. Images are 20×.
Figure 11:
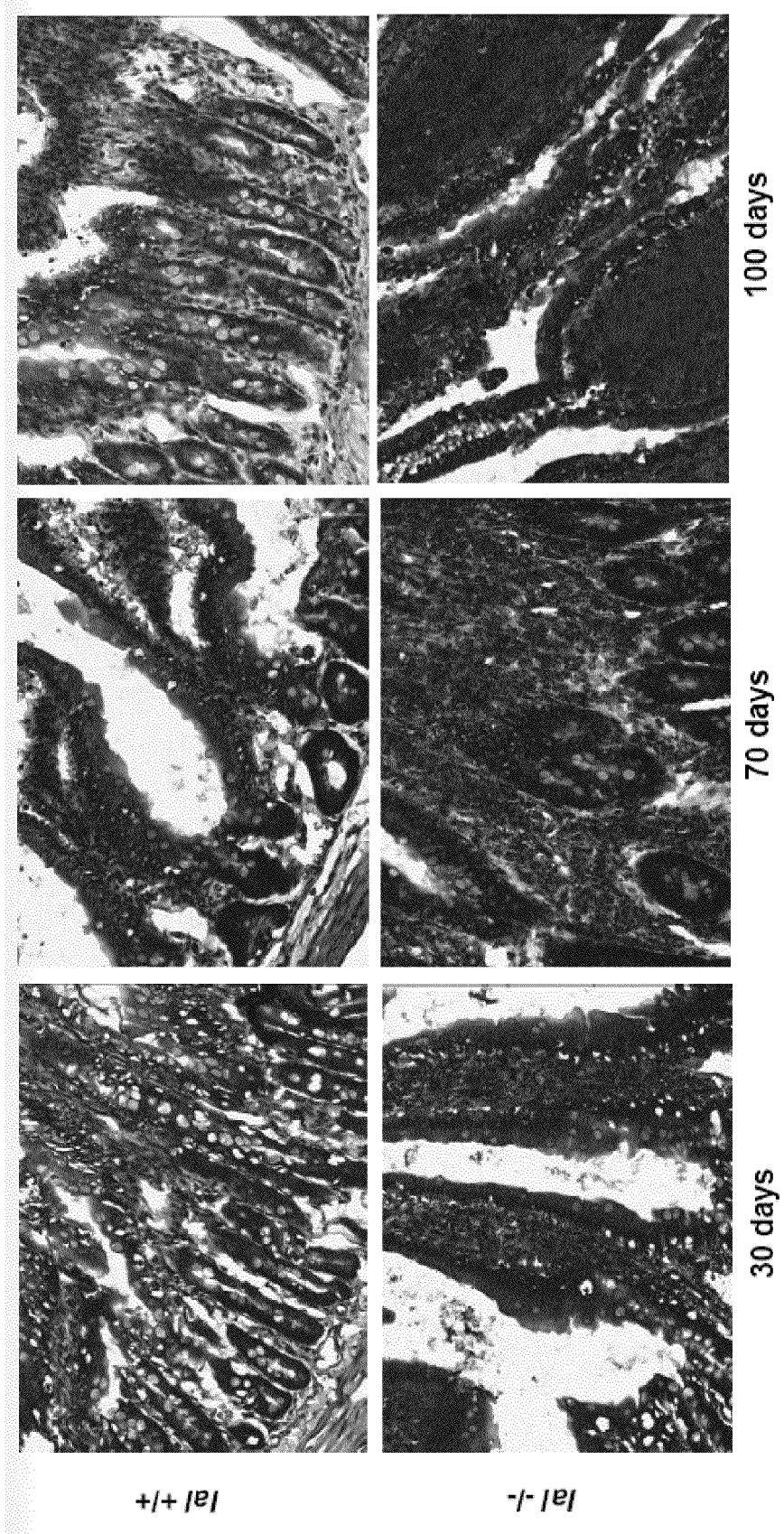
FIG. 11 depicts exemplary lipid accumulation in small intestine of LAL deficient Yoshida rats. Oil Red O staining showed large cellular accumulations of neutral lipids in the small intestines of LAL deficient Yoshida rats compared with wild-type animals. The lipid accumulation was age-dependent with marked lipid storage throughout the small intestines at 100 days. Images are 20×.

Post mortem analyses were performed to evaluate size, weight, and lipid accumulation in various tissues. For example, liver and spleen sizes of 14 week old wild-type and homozygous LAL deficient rats were compared as shown in FIG. 7. Liver (FIG. 8A) and spleen weights (FIG. 8B) at necropsy (percent of total body weight) were also determined Histology using Oil Red O staining were performed to determine lipid accumulation in various tissues (e.g., liver, spleen, and intestine). Oil Red O staining showed large cellular accumulations of neutral lipid (red deposits) in the livers (FIG. 9), spleens (FIG. 10), and small intestine (FIG. 11) of LAL deficient Yoshida rats compared with wild-type animals. As shown in FIGS. 9, 10 and 11, the lipid accumulation was age-dependent dependent with marked lipid storage throughout the livers, spleens, and small intestine at 100 days. Additional tissue analysis are performed to determine cholesterol and/or triglyceride levels, such as in liver and spleen. LAL levels are also determined in various tissues including liver and spleen. In addition, serum anti-LAL antibody levels are determined.

rhLAL Treatment Promotes Weight Gain

Figure 13:
FIG. 13 depicts an exemplary size comparison of LAL deficient Yoshida rats at study week 10 treated with vehicle control or 1 mg/mL rhLAL.
Figure 14:
FIG. 14 depicts an exemplary size comparison of LAL deficient Yoshida rats at study week 13 treated with vehicle control or 0.5 mg/mL rhLAL.

Recombinant human LAL (rhLAL) was expressed and purified as described in Example 1. Homozygous LAL deficient Yoshida rats were administered 5 or 10 weekly injections of varying doses of rhLAL or vehicle control via intravenous administration, according to the experimental design shown in FIG. 12. Control wild-type rats were untreated. In-life evaluations, such as general health, weekly body weights, and serum chemistry of the animals treated with rhLAL and vehicle were evaluated. As shown in FIG. 13, at week 10, a homozygous LAL deficient rat treated with rhLAL at 1 mg/kg dose level had significantly larger body as compared to a homozygous LAL deficient rat treated with vehicle. As shown in FIG. 14, at week 13, a homozygous LAL deficient rat treated with rhLAL at 0.5 mg/kg dose level had significantly higher body weight as compared to a homozygous LAL deficient rat treated with vehicle.

Figure 16:
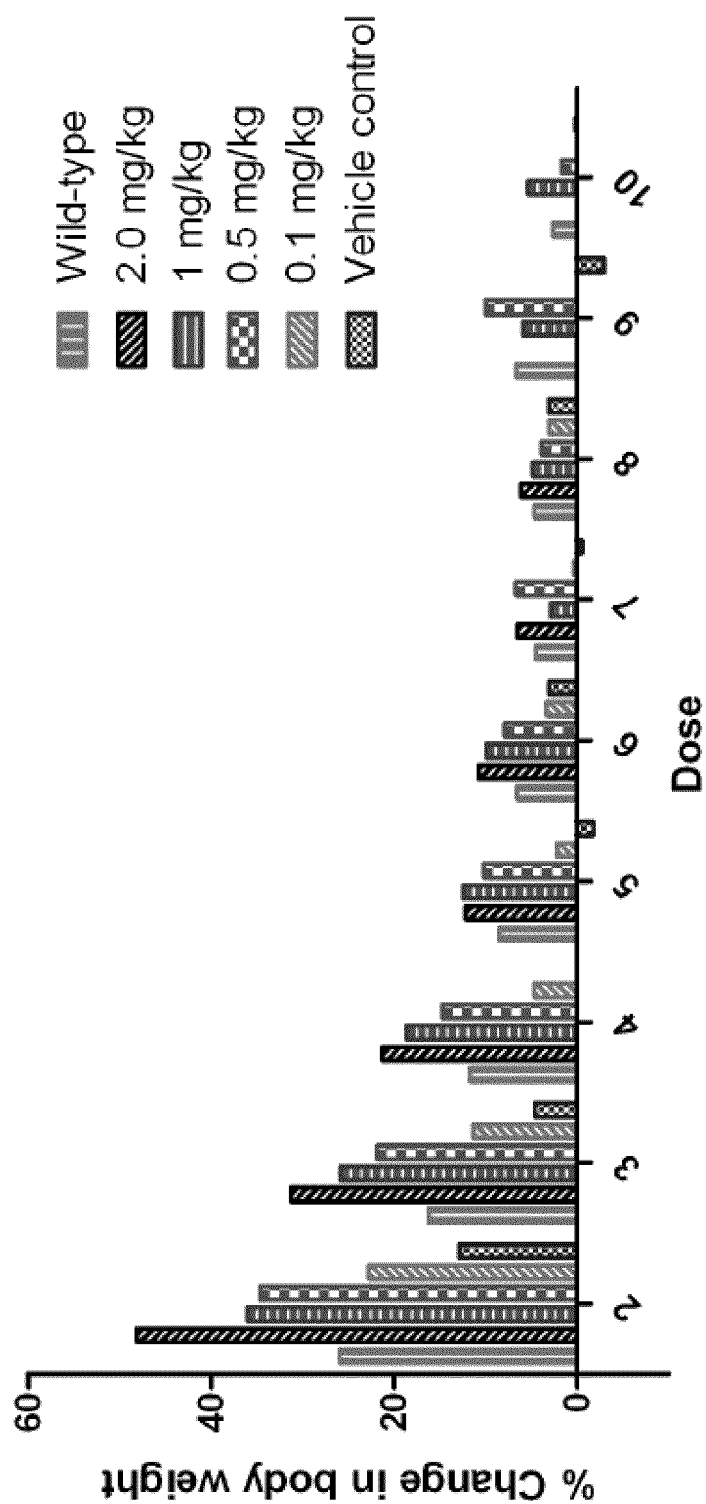
FIG. 16 depicts exemplary weekly percent body weight gain in wild-type rats and LAL deficient Yoshida rats treated with vehicle control or varying doses of rhLAL for 10 weeks starting at 5 weeks of age.

Dose-responsive body weight gain was also determined Specifically, homozygous LAL deficient Yoshida rats were treated with weekly administration of 0.1 mg/kg rhLAL, 0.5 mg/kg rhLAL, 1.0 mg/kg rhLAL, 2.0 mg/kg rhLAL or vehicle control for 10 weeks starting at 5 weeks of age and demonstrated a dose-responsive body weight gain. Exemplary results are shown in FIGS. 15A-15E. Weekly percent body weight gain were also determined and exemplary results were shown in FIG. 16. As can be seen, weekly percent body weight gain for rhLAL treated rats was similar to that of wild-type animals. In particular, rapid weight gain was observed in first month on dosing with rhLAL.

Figure 17A:
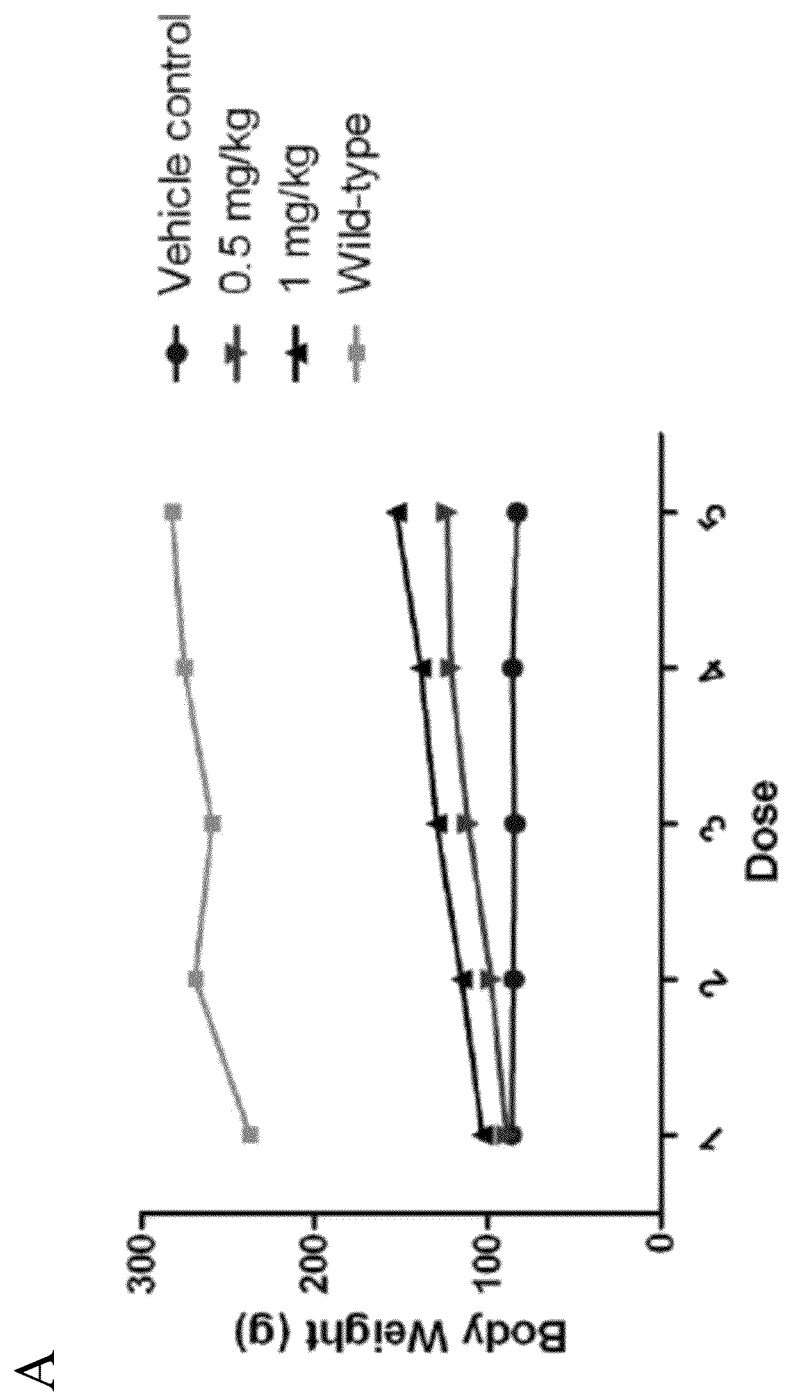
FIG. 17A depicts the weight gain over 5 weeks for wild-type and LAL deficient rats.

A second dosing regimen was used to determine body weight gain in animals treated for 5 weeks starting at 10 weeks of age. Specifically, homozygous LAL deficient Yoshida rats were treated with weekly administration of 0.5 mg/kg rhLAL, 1.0 mg/kg rhLAL, or vehicle control for 5 weeks starting at 10 weeks of age and exemplary results are shown in FIGS. 17A, 17B, and 17C. As can be seen, weight gain was also observed in animals treated with rhLAL using this 5-week dosing regimen.

rhLAL Treatment Ameliorates Liver Pathology

In order to evaluate the effect of rhLAL treatment in liver pathology, animals received 10 doses of rhLAL starting at 5 weeks of age at dosage of 0.1 mg/kg, 0.5 mg/kg, 1.0 mg/kg, 2.0 mg/kg, or vehicle control were sacrificed at week 14. Gross liver pathology (FIG. 18A) were assessed and liver weight at necropsy as % of total body weight were determined (FIG. 18B). Exemplary results are shown in FIGS. 18A and 18B. As can be seen, treatment of rhLAL at various doses resulted in resolution of gross liver pathology. In particular, treatment with doses at 0.5 mg/kg rhLAL or greater had significantly improved gross liver pathology. In addition, treatment of rhLAL also significantly decreased liver weight at necropsy. As can be seen from FIG. 18B, treatment of 0.1 mg/kg, 0.5 mg/kg rhLAL, 1 mg/kg, or 2 mg/kg rhLAL for 10 doses resulted in a similar relative liver weight as a percent of total body weight, comparable to the liver weight relative to total body weight in to wild-type animals.

In another experiment, a different dosing regimen was used to determine resolution of gross liver pathology. Specifically, animals received 5 doses of rhLAL at 0.1 mg/kg or 2 mg/kg and were sacrificed at week 9. Exemplary results of the gross liver pathology are shown in FIG. 19A. In another experiment, animals received 5 doses of rhLAL at 0.5 mg/kg or 1 mg/kg starting at 10 weeks of age and exemplary results of the gross liver pathology are shown in FIG. 19B. Exemplary results of the liver weight at necropsy are shown in FIG. 19C.

Figure 20:
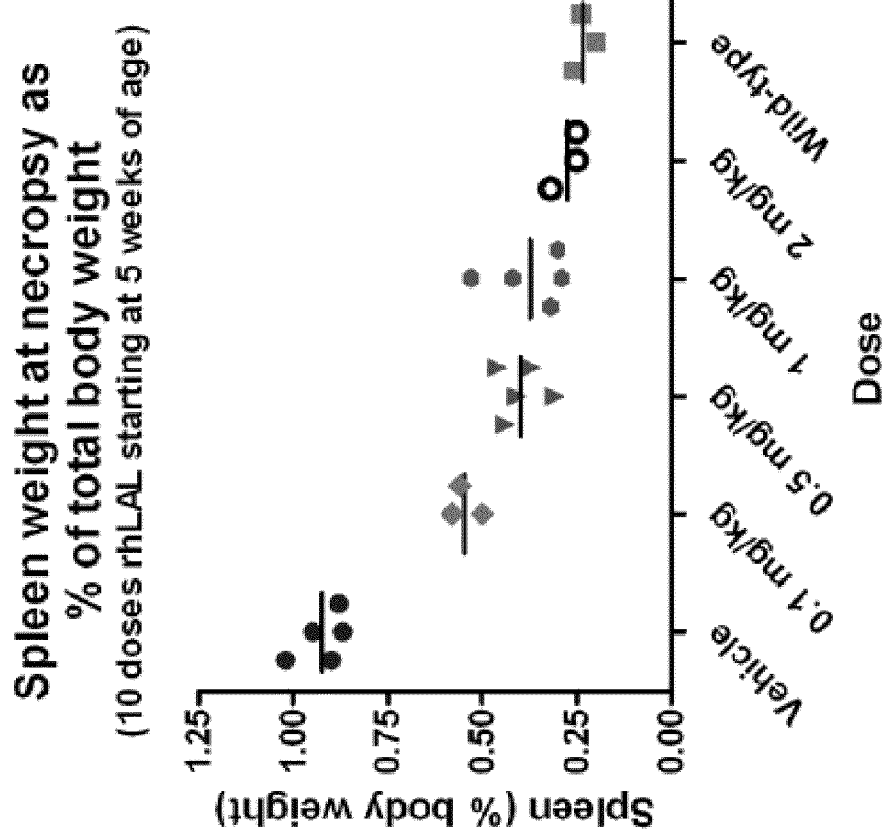
FIG. 20 depicts exemplary spleen weight at necroscopy as a percentage of total body weight of wild-type rats and LAL deficient Yoshida rats treated with vehicle control or varying doses of rhLAL for 10 weeks starting at 5 weeks of age. Animals were necropsied at week 14. Animals treated with rhLAL exhibited a similar relative spleen weight compared to wild-type animals.
Figure 21:
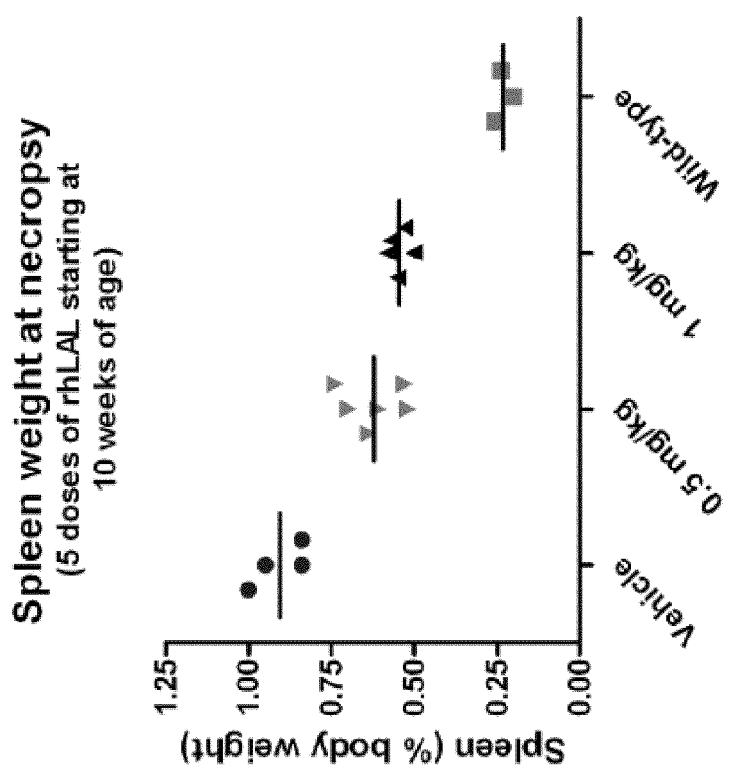
FIG. 21 depicts exemplary spleen weight at necroscopy as a percentage of total body weight of wild-type rats and LAL deficient Yoshida rats treated with vehicle control or varying doses of rhLAL for 5 weeks starting at 10 weeks of age. Animals treated with rhLAL exhibited a similar relative spleen weight compared to wild-type animals.

A dose-related decrease in relative spleen weight in treated animals was also observed. In one experiment, animals were treated with 10 doses of rhLAL at 0.1mg/kg, 0.5 mg/kg, 1 mg/kg, 2 mg/kg or vehicle starting at 5 weeks of age and then were sacrificed. As shown in FIG. 20, treated animals exhibited similar relative spleen weights (as a percent of total body weight) as compared to wild-type animals. In another experiment, animals were treated with 5 doses of rhLAL at 0.5 mg/kg, 1.0 mg/kg or vehicle starting at 10 weeks of age. Treated animals exhibited similar relative spleen weights (as a percent of total body weight) as compared to wild-type animals. Exemplary results are shown in FIGS. 21.

rhLAL Treatment Reduces Lipid Accumulation and Improves Morphology

Hematoxylin and eosin (H&E) staining and Oil Red O staining was performed. Typically, H&E staining is performed on formalin-fixed paraffin embedded tissue and preserves detailed morphology, while paraffin processing dissolves fats. In general, H&E staining permits identification of tissue type and morphology. Typically, Oil Red O staining is performed on formalin-fixed frozen tissue and preserved lipids, while morphology may be compromised. In general, Oil Red O staining permits identification of neutral lipids and triglycerides.

Figure 22:
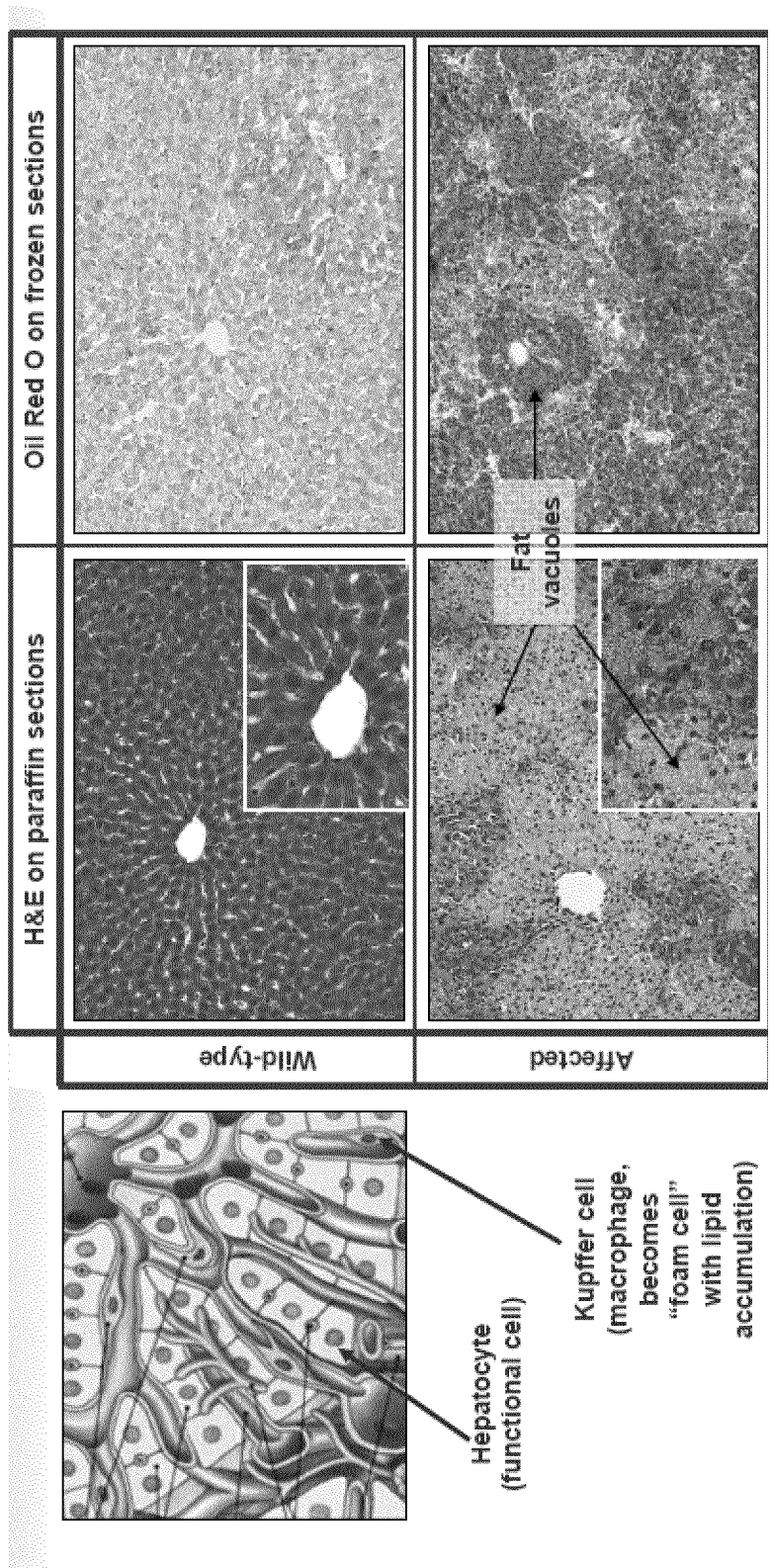
FIG. 22 depicts exemplary characterization of livers from wild-type rats and LAL deficient Yoshida rats by H&E and Oil Red O staining.
Figure 23:
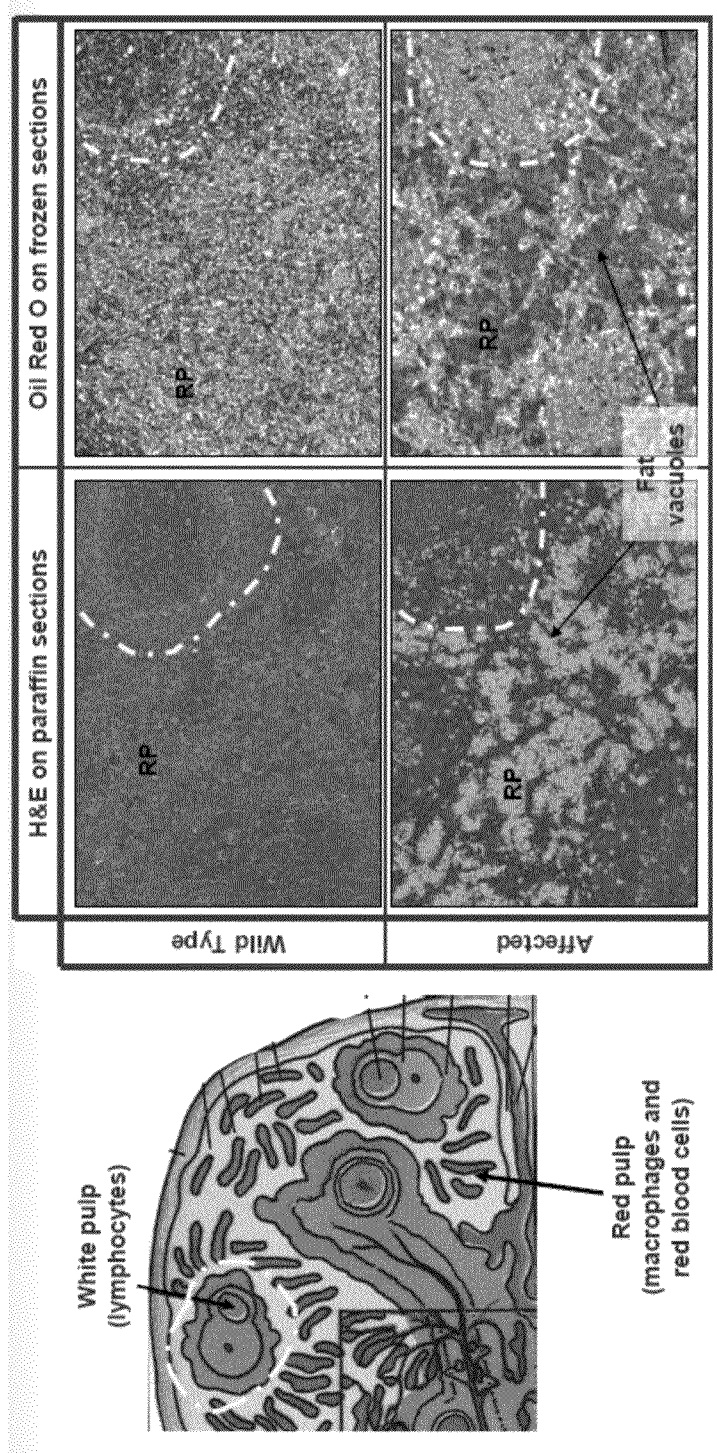
FIG. 23 depicts exemplary characterization of spleens from wild-type rats and LAL deficient Yoshida rats by H&E and Oil Red O staining.
Figure 24:
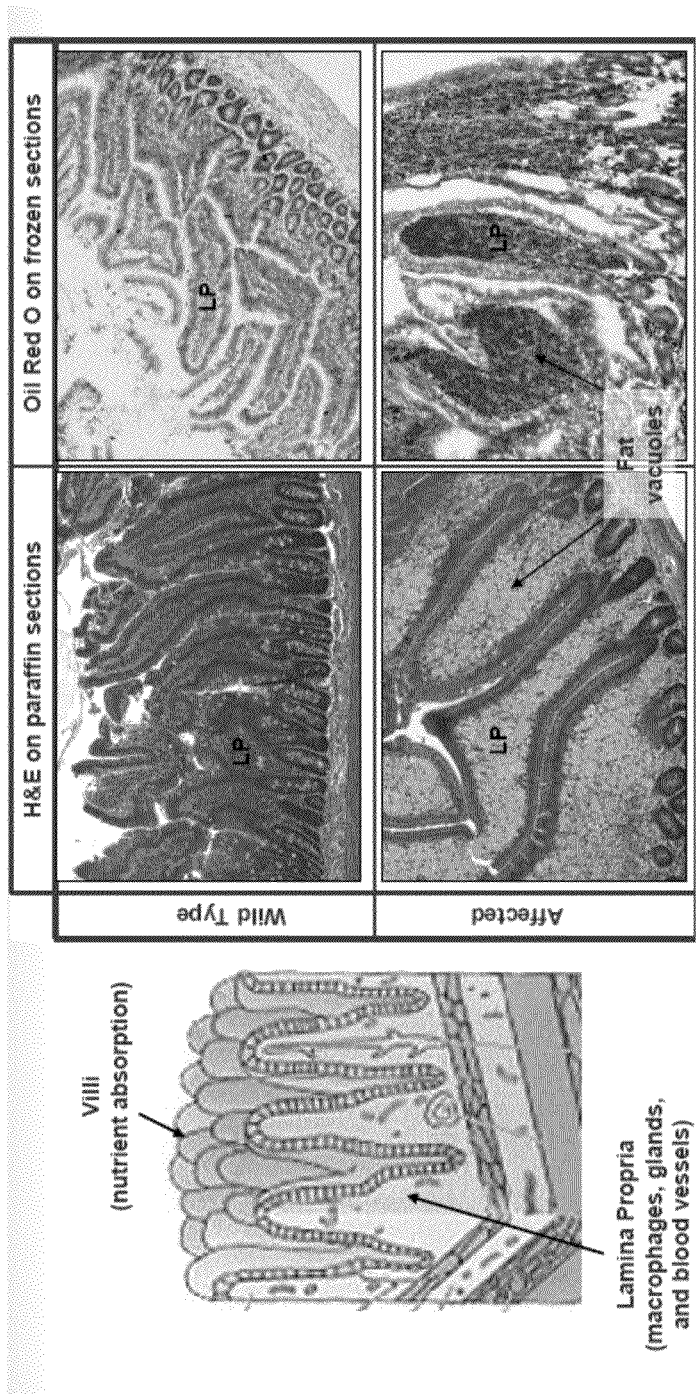
FIG. 24 depicts exemplary characterization of small intestines from wild-type rats and LAL deficient Yoshida rats by H&E and Oil Red O staining.

First, untreated Yoshida rat liver, spleen and small intestine were analyzed by H&E and Oil Red O staining. As can be seen in FIG. 22, livers of untreated Yoshida rats exhibit age-dependent lipid accumulation in both hepatocytes and Kupffer cells, with marked vacuolization at Day 100. As can be seen in FIG. 23, spleens of untreated Yoshida rats exhibit age-dependent lipid accumulation in macrophages of red pulp (RP), with marked vacuolization at Day 100. As can be seen in FIG. 24, small intestines of untreated Yoshida rats exhibit age-dependent lipid accumulation in macrophages of lamina propria (LP), with marked widening of villi at Day 100.

Figure 25:
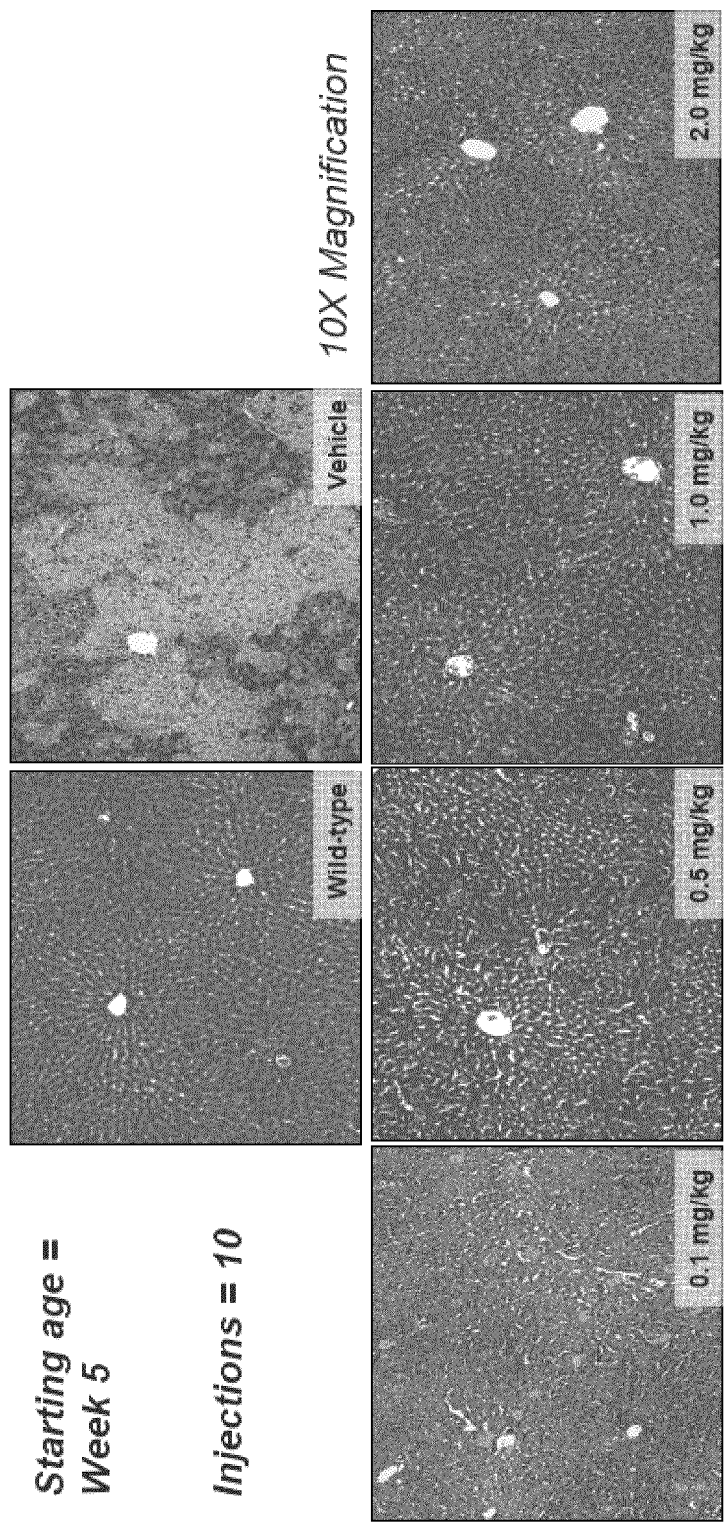
FIG. 25 depicts exemplary liver morphology by H&E staining of wild-type rats and LAL deficient Yoshida rats treated with vehicle control or varying doses of rhLAL for 10 weeks starting at 5 weeks of age.
Figure 26:
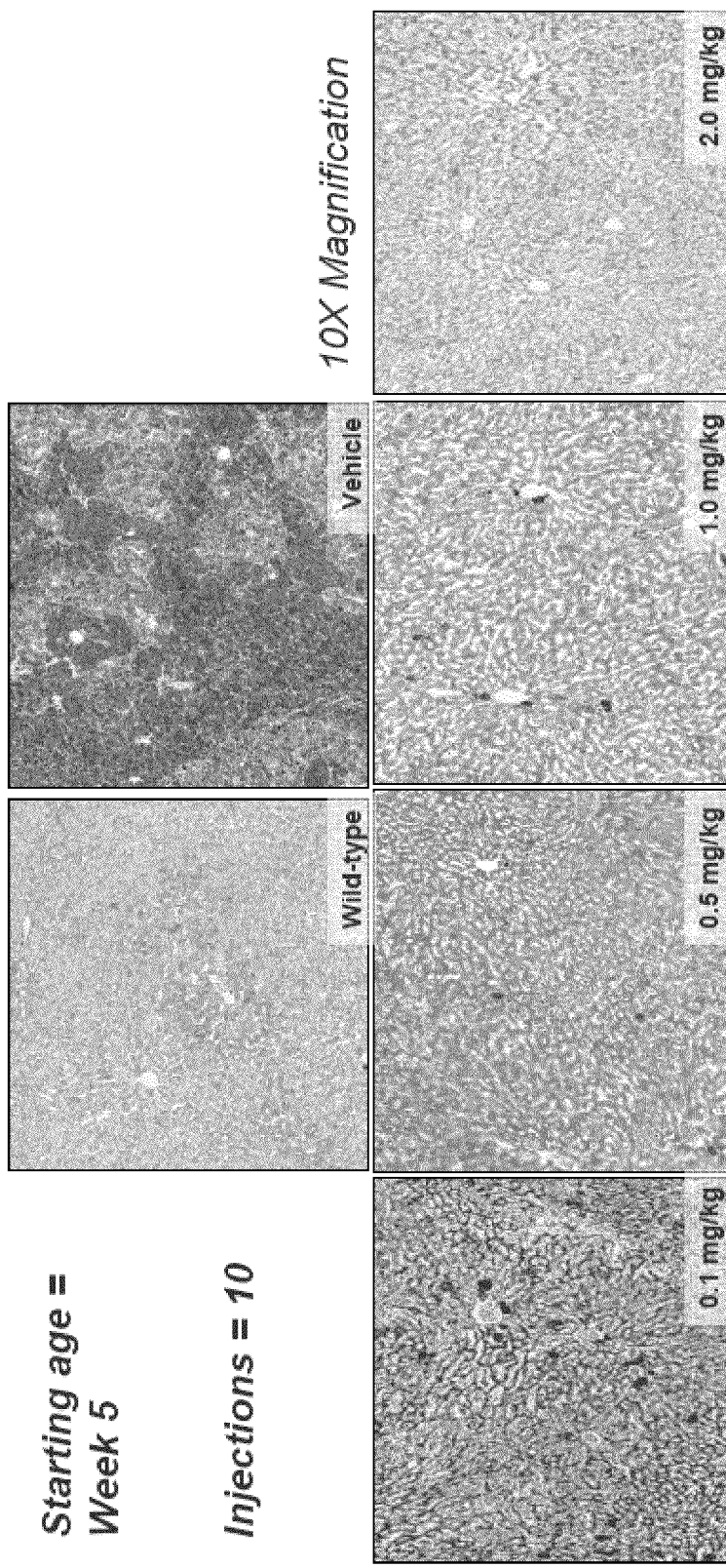
FIG. 26 depicts exemplary lipid accumulation in the liver by Oil Red O staining of wild-type rats and LAL deficient Yoshida rats treated with vehicle control or varying doses of rhLAL for 10 weeks starting at 5 weeks of age.
Figure 27:
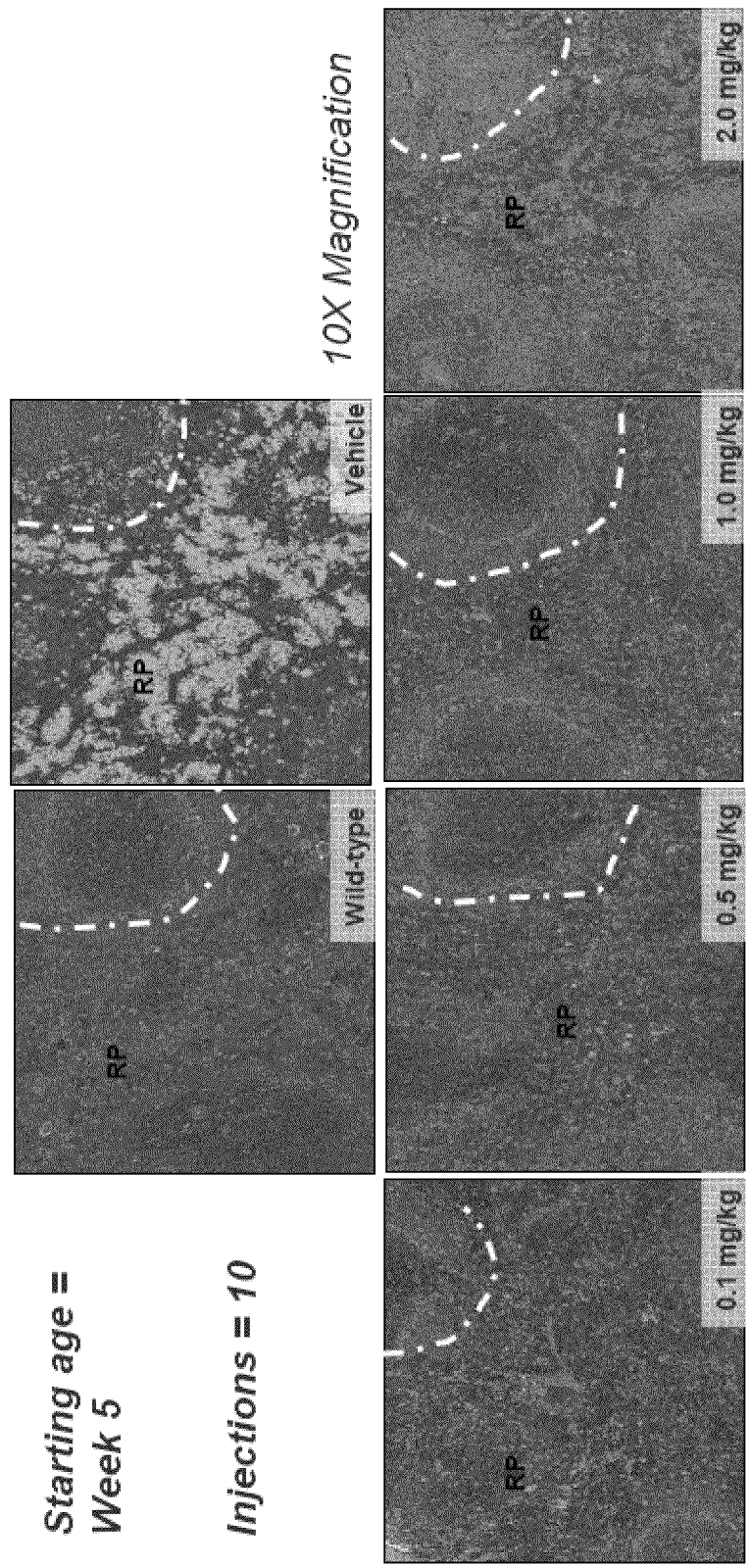
FIG. 27 depicts exemplary spleen morphology by H&E staining of wild-type rats and LAL deficient Yoshida rats treated with vehicle control or varying doses of rhLAL for 10 weeks starting at 5 weeks of age.
Figure 28:
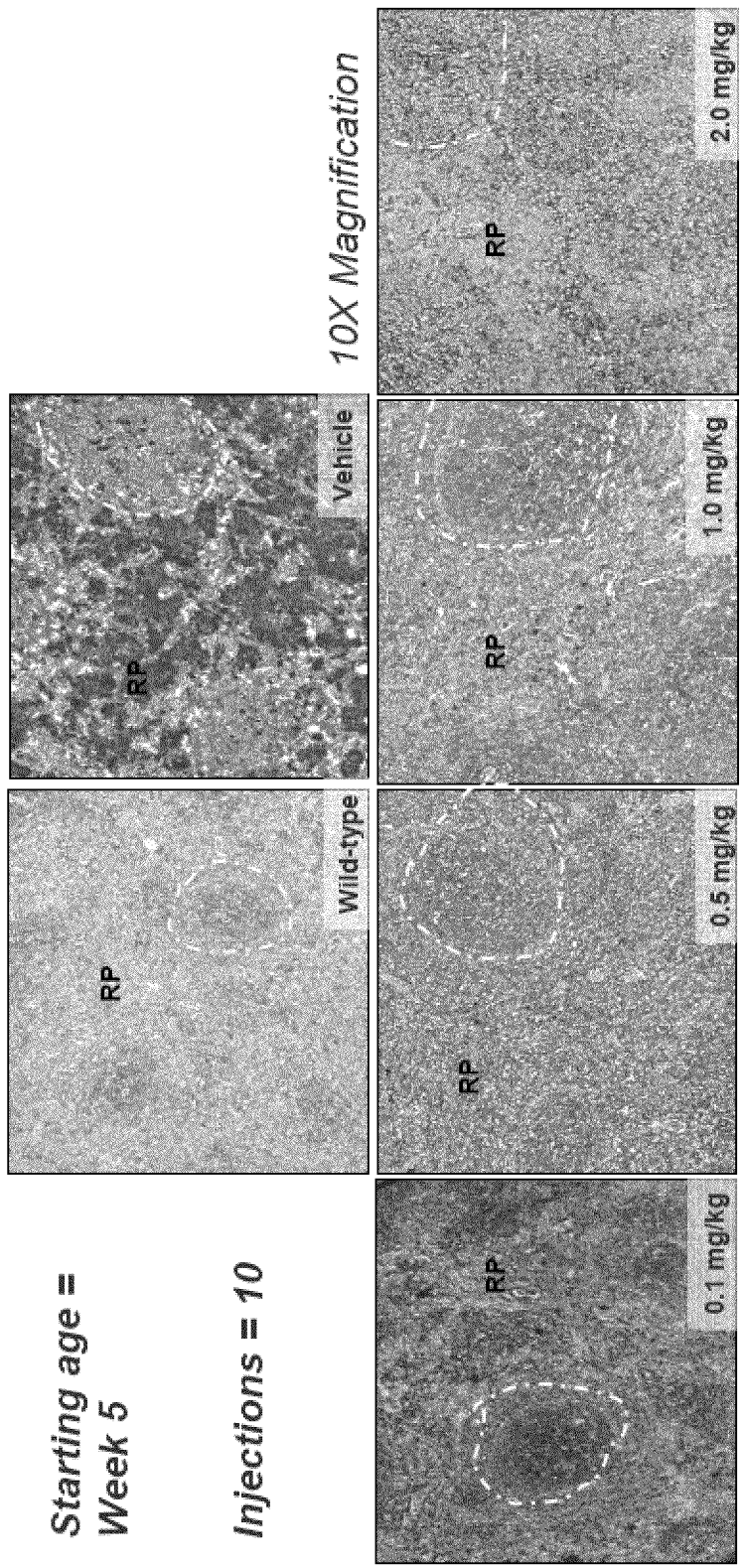
FIG. 28 depicts exemplary lipid accumulation in the spleen by Oil Red O staining of wild-type rats and LAL deficient Yoshida rats treated with vehicle control or varying doses of rhLAL for 10 weeks starting at 5 weeks of age.
Figure 29:
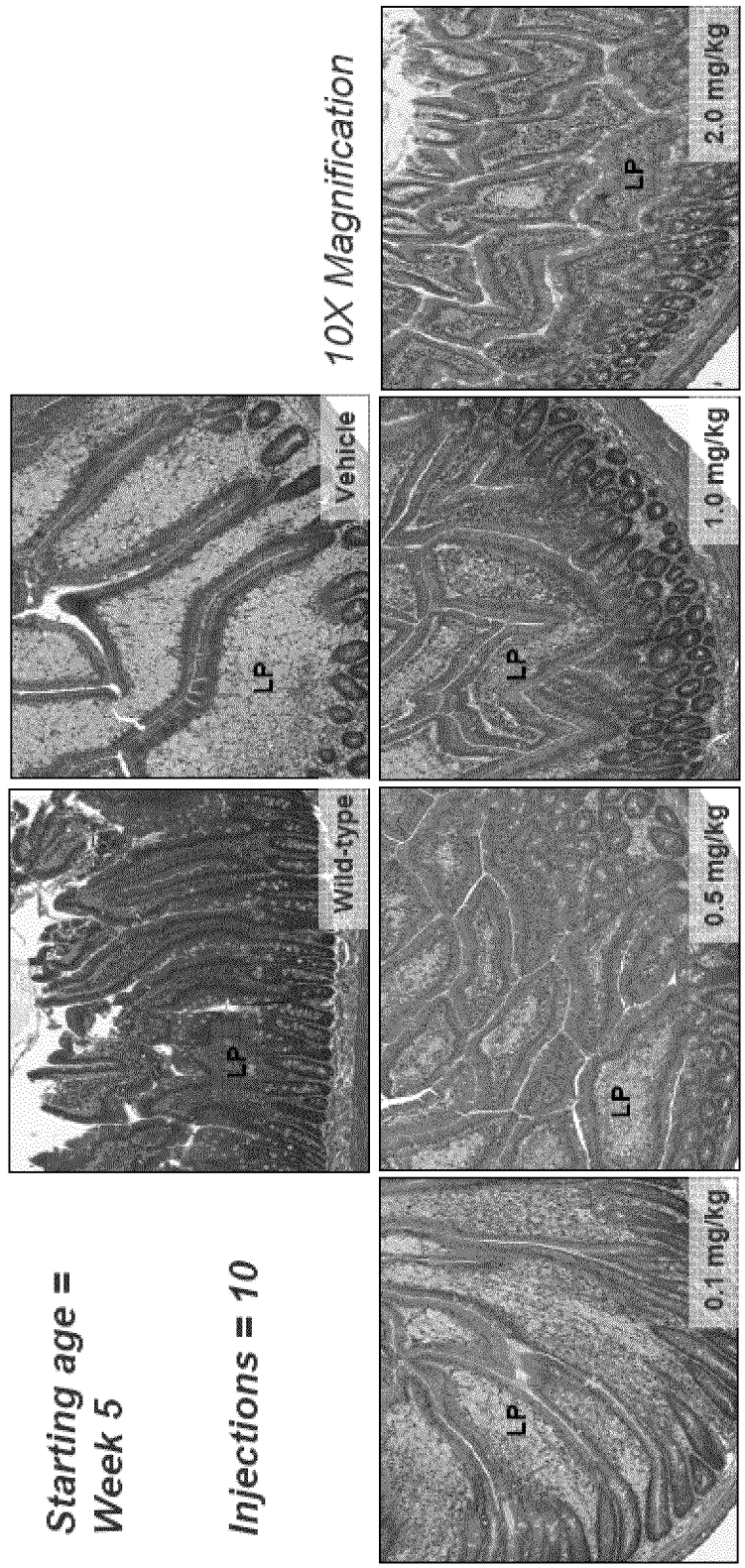
FIG. 29 depicts exemplary small intestine morphology by H&E staining of wild-type rats and LAL deficient Yoshida rats treated with vehicle control or varying doses of rhLAL for 10 weeks starting at 5 weeks of age.
Figure 30:
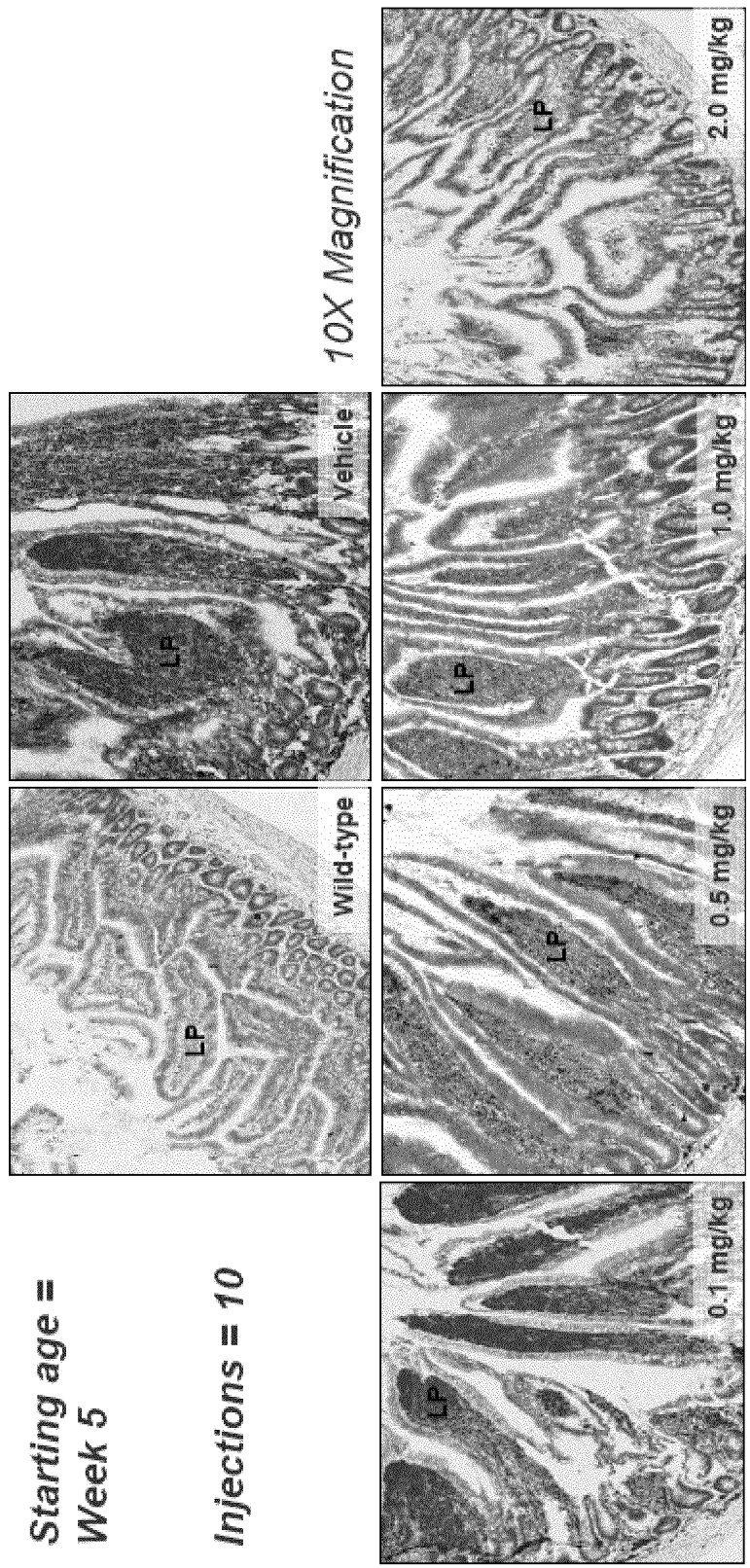
FIG. 30 depicts exemplary lipid accumulation in the small intestine by Oil Red O staining of wild-type rats and LAL deficient Yoshida rats treated with vehicle control or varying doses of rhLAL for 10 weeks starting at 5 weeks of age.

To determine the effect of rhLAL treatment on lipid accumulation and morphology, the following dosing regimen was used: 10 weekly injections at 0.1 mg/kg, 0.5 mg/kg, 1.0 mg/kg, or 2.0 mg/kg rhLAL starting at 35 days of age. Exemplary results from H&E and Red Oil O staining of liver are shown in FIG. 25 (H&E), FIG. 26 (Oil Red O). Morphology was improved by reducing foam cell numbers and improvement was observed even at low doses of rhLAL. Oil Red O staining showed a marked reduction of lipids in hepatocytes and Kupffer cells in all treated groups. The lipid-reduction in liver was dose-dependent. Exemplary results from H&E and Red Oil O staining of spleen are shown in FIG. 27 (H&E), FIG. 28 (Oil Red O). Morphology was improved by reducing foam cell numbers in red pulp and improvement was observed even at low doses of rhLAL. Oil Red O staining showed marked reduction of lipids in red pulp of all treated groups. The lipid reduction in spleen was dose dependent. Exemplary results from H&E and Red Oil O staining of small intestine are shown in FIG. 29 (H&E), FIG. 30 (Oil Red O). In treated groups, villi of the small intestine became thinner by reduction of foam cell numbers in lamina propria. Oil Red O staining showed reduction of lipid in lamina propria.

Figure 31:
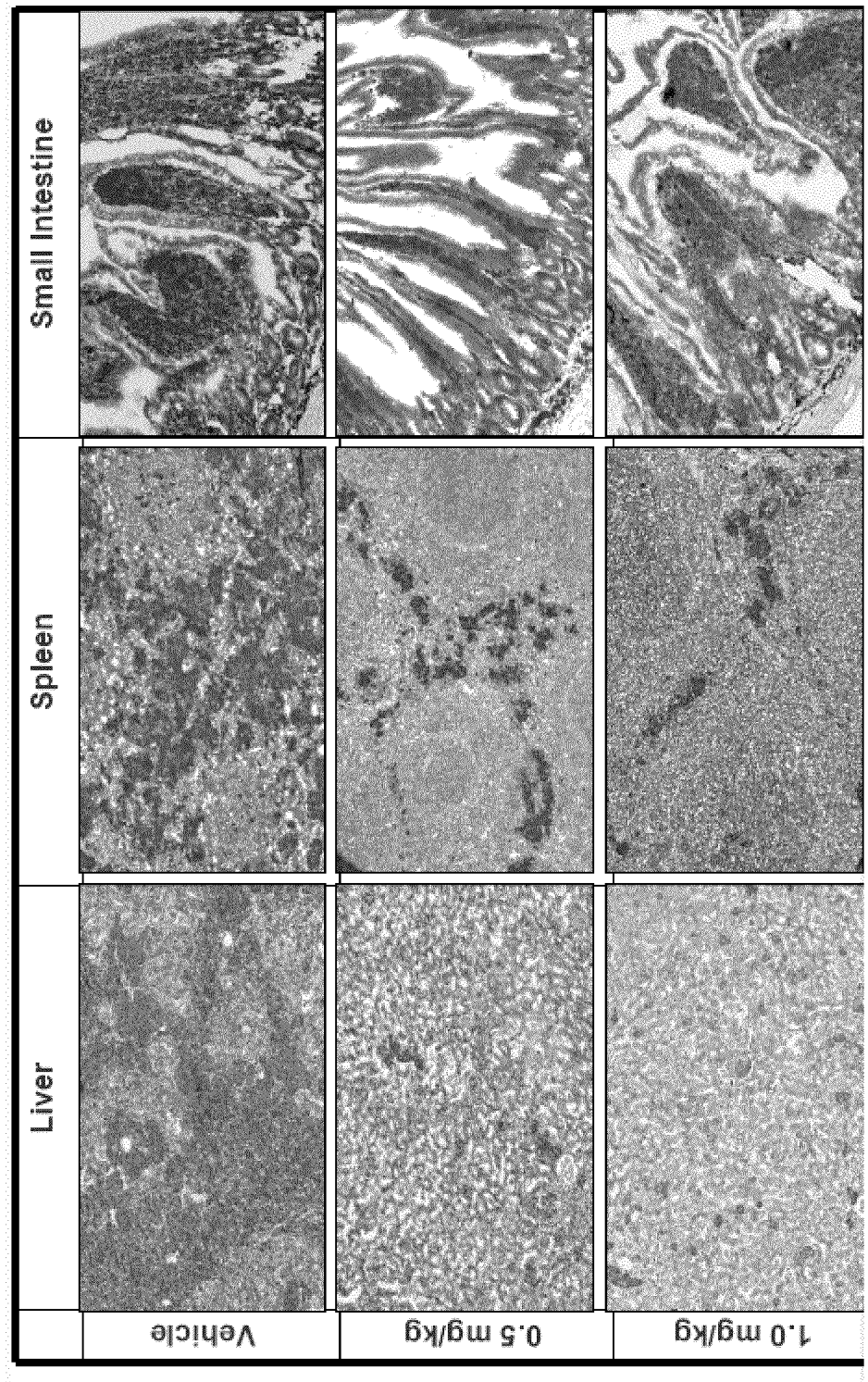
FIG. 31 depicts exemplary lipid accumulation in the liver, spleen, and small intestine by Oil Red O staining of wild-type rats and LAL deficient Yoshida rats treated with vehicle control or varying doses of rhLAL for 5 weeks starting at 10 weeks of age.

In another experiment, to determine the effect of rhLAL treatment on lipid accumulation and morphology, the following dosing regimen was used: 5 weekly injections at 0.5 mg/kg or 1.0 mg/kg rhLAL starting at 70 days of age. Exemplary results from Red Oil O staining of liver, spleen and small intestine demonstrating reduction of lipids are shown in FIG. 31.

To further determine the effect of rhLAL treatment on lipid accumulation, the following dosing regimen were used:
1. 5 weekly injections at 0.5 mg/kg or 1.0 mg/kg rhLAL starting at 70 days of age.
2. 10 weekly injections at 0.5 mg/kg or 1.0 mg/kg rhLAL starting at 35 days of age.
3. 5 weekly injections at 0.1 mg/kg or 2.0 mg/kg rhLAL starting at 35 days of age.

Figure 32:
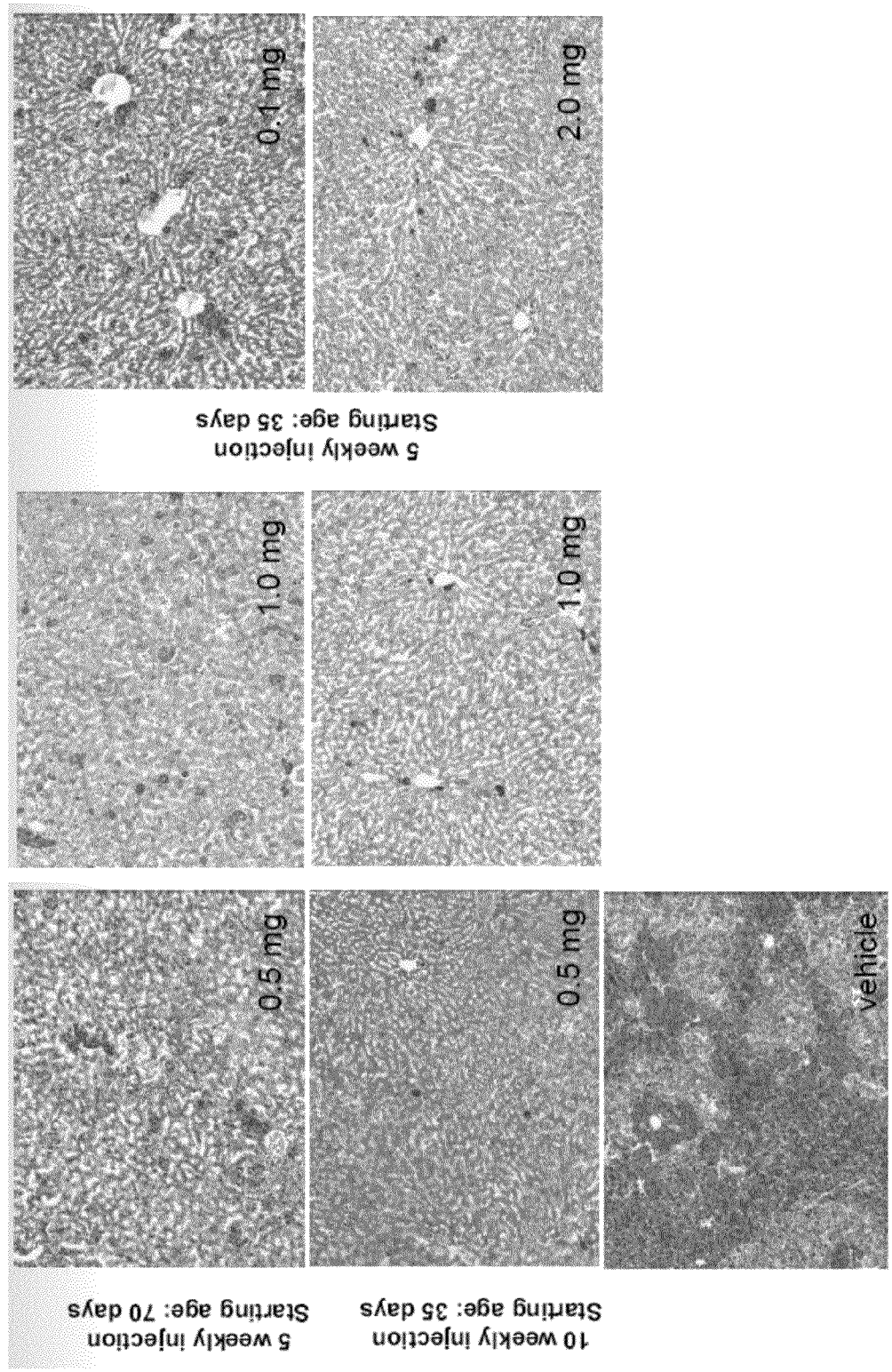
FIG. 32 depicts exemplary lipid accumulation in livers of LAL deficient Yoshida rats treated with vehicle control or varying doses of rhLAL for 5 weeks starting at 10 weeks of age, for 10 weeks starting at 5 weeks of age, or for 5 weeks starting at 5 weeks of age. Images are 10×. Marked reduction of lipid accumulation was observed in livers of all treated groups compared with vehicle-control treated animals.
Figure 33:
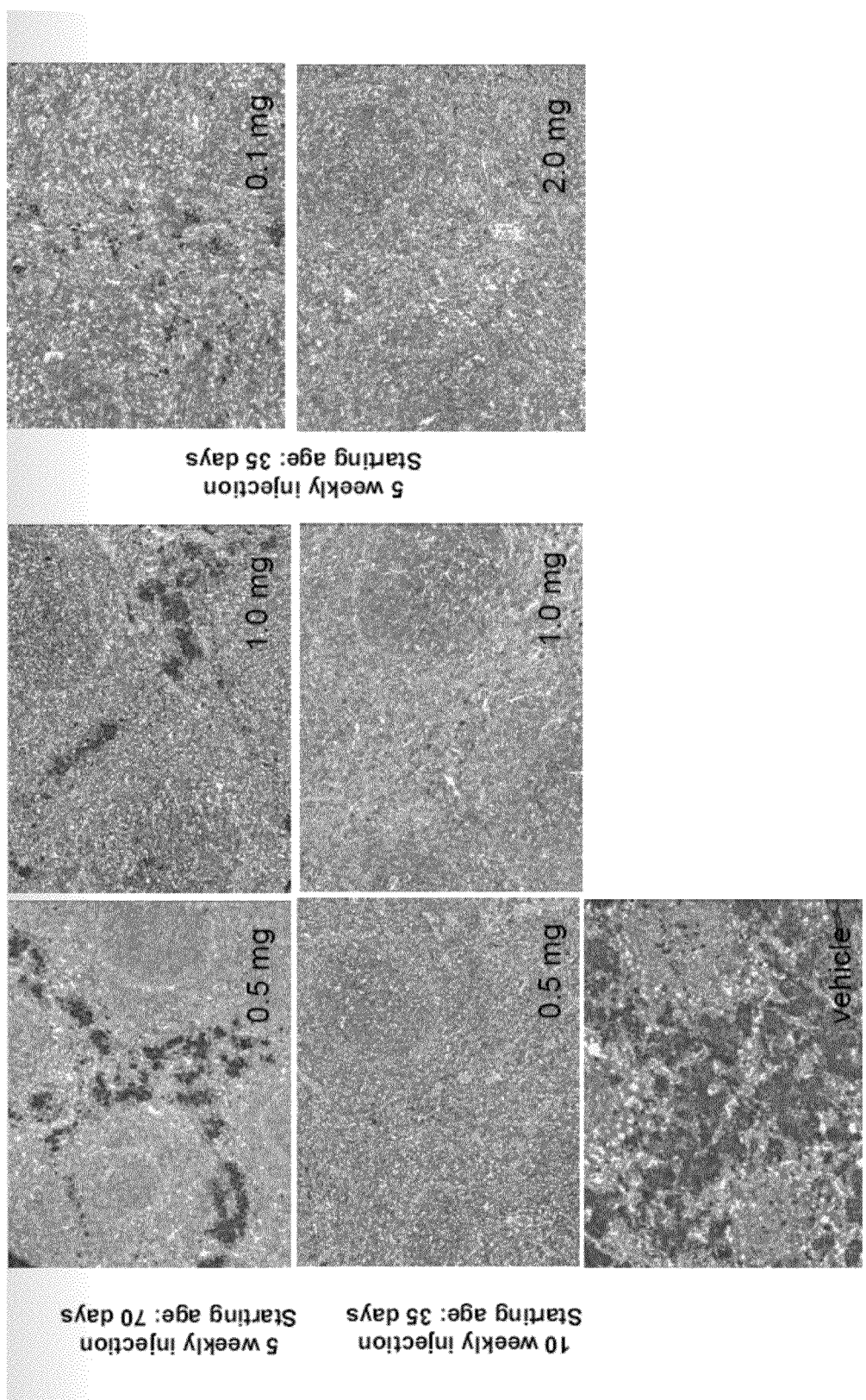
FIG. 33 depicts exemplary lipid accumulation in spleens of LAL deficient Yoshida rats treated with vehicle control or varying doses of rhLAL for 5 weeks starting at 10 weeks of age, for 10 weeks starting at 5 weeks of age, or for 5 weeks starting at 5 weeks of age. Images are 10×. Marked reduction of lipid accumulation was observed in spleens of all treated groups compared with vehicle-control treated animals. In animals treated with 0.5 mg, 1.0 mg, and 2.0 mg starting at 5 weeks of age, lipid deposits were barely detected.
Figure 34:
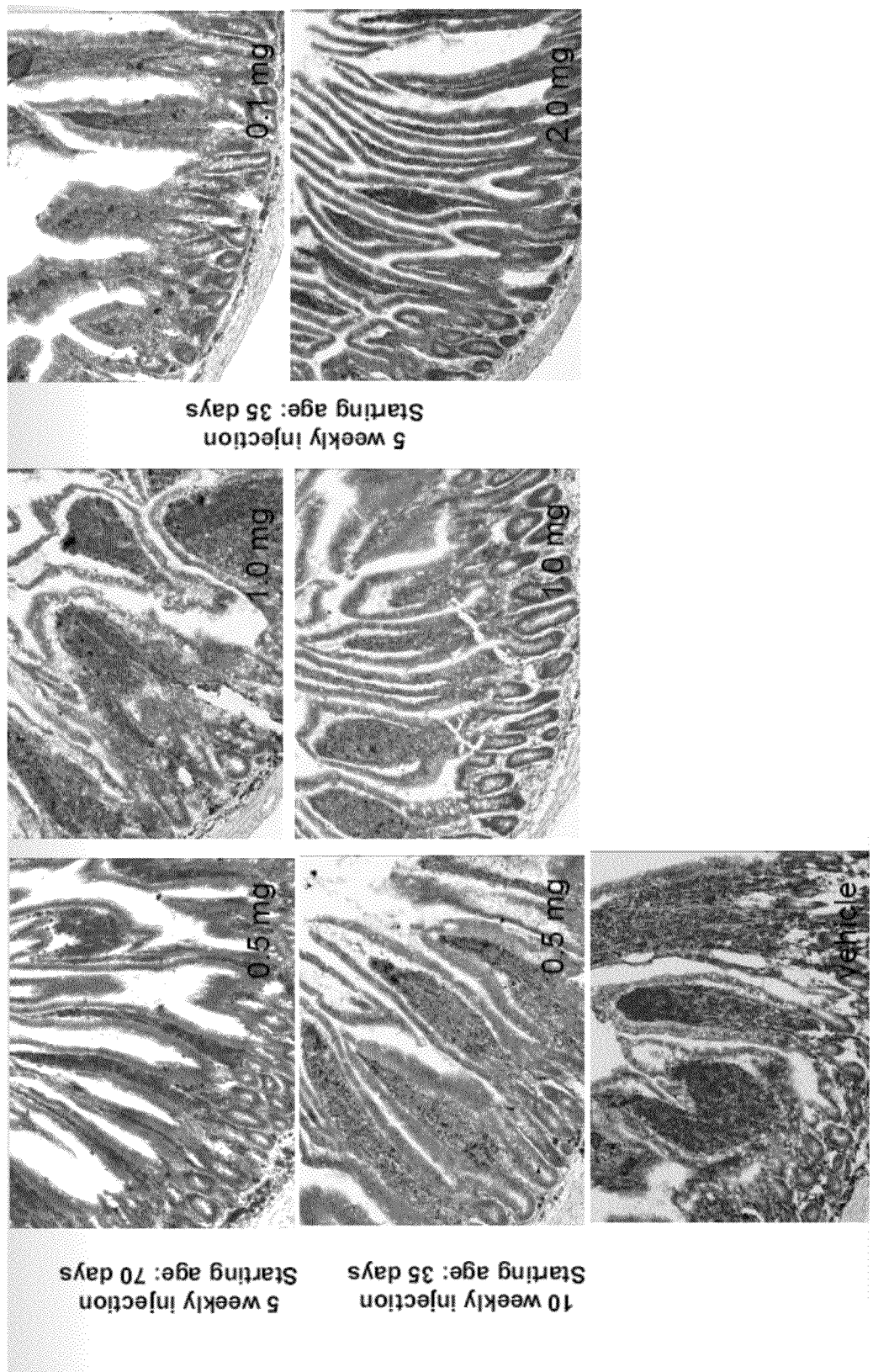
FIG. 34 depicts exemplary lipid accumulation in small intestines of LAL deficient Yoshida rats treated with vehicle control or varying doses of rhLAL for 5 weeks starting at 10 weeks of age, for 10 weeks starting at 5 weeks of age, or for 5 weeks starting at 5 weeks of age. Images are 10×. Marked reduction of lipid accumulation was observed in small intestines of all treated groups compared with vehicle-control treated animals with marked reduction in the group treated with 2.0 mg of rhLAL.

Exemplary results are shown in FIGS. 32 (liver), FIG. 33 (spleens), and FIG. 34 (small intestines). As can be seen in FIG. 32, marked reduction of lipid accumulation was found in the livers of all treated groups compared with the vehicle control. Best results were seen in the 2.0 mg group (with 5 injections only). FIG. 33 shows marked reduction of lipid accumulation was found in the spleens of all treated groups compared with the vehicle control. In animals treated with 0.5, 1.0 and 2.0 mg/kg starting at the age of 30 days, lipid deposits were barely detected. Reduction of lipid accumulation was also found in the small intestines of all treated groups compared with the vehicle control with marked reduction in the 2.0 mg group (5 injections only) (FIG. 34).

In summary, these experiments showed that (1) treated animals exhibited a dose-responsive weight gain with a similar % gain weekly compared to wild-type; (2) animals treated with LAL demonstrated a marked resolution of gross liver, spleen, and intestine pathology; (3) H&E staining evaluation showed a morphological improvement in liver, spleen and intestine; and (4) Oil Red O staining evaluation showed a dose-responsive decrease in lipid staining in liver, spleen, and intestine. These results demonstrate that rhLAL treatment is effective, even at a low dose, in treating various symptoms of LALD disease. In addition, the above results also demonstrate that rhLAL has significant therapeutic effect in treating developmental impairment (cachexia or failure to thrive), the most devastating symptom of Wolman's disease.

Example 3

Survival/Maintenance Dose Study Design and Dose Selection

Figure 35:
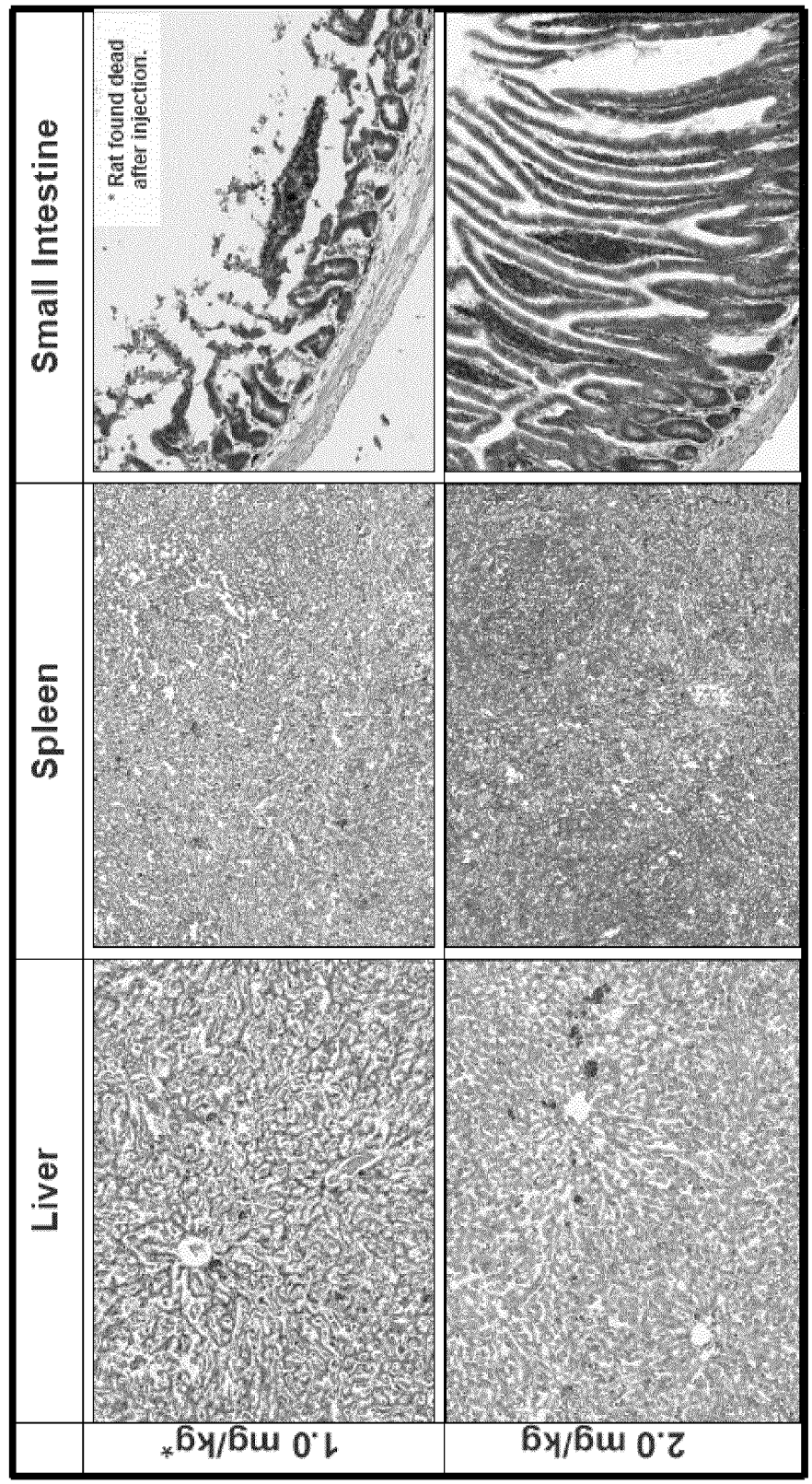
FIG. 35 depicts exemplary lipid accumulation in liver and spleen of LAL deficient Yoshida rats treated with 1 mg/kg or 2 mg/kg of rhLAL for 5 weeks starting at 5 weeks of age. Greater reductions in lipid accumulation was observed at 2 mg/kg compared to 1 mg/kg following 5 doses, confirming that 2 mg/kg as the dose selected for the "loading" dose phase of the survival study.

It is contemplated that a two-dose (i.e., survival/maintenance) treatment regimen is desirable for treating LALD disease (e.g., Wolman's disease). This example is designed to select appropriate survival/maintenance doses. As observed from clinical signs, body weights, gross and microscopic pathology, doses such as 0.1, 0.5, and 1 mg/kg were selected for the survival study. In order to select an appropriate dose for the "loading" dose phase of the survival study, reductions in lipid accumulation in liver, spleen and small intestine of animals treated at 1 or 2 mg/kg (5 weekly doses starting on day 35) were compared. Exemplary results are shown in FIG. 35. As can be seen, greater reductions in lipid accumulation were observed at 2 mg/kg compared to 1 mg/kg following 5 doses. This data indicates that 2 mg/kg more effectively resolves lipid accumulation in tissues following 5 doses; therefore, this dose is selected for the "loading" dose phase of the survival study.

Exemplary design for survival/maintenance dose study is shown in FIG. 36. Study endpoints include the following: Overall survival of the animals is evaluated for up to at least 6 months. Pictures of the abdominal cavity are taken. Liver and spleen weight and gross pathology is determined Plasma levels of free cholesterol, cholesterol esters and/or total cholesterol are measured at various time points. Histopathology (e.g., H & E staining and/or Oil Red O staining) of liver, spleen and/or small intestine is performed. rhLAL levels and localization in animals (e.g., liver, spleen) is measured. Tissue (liver, spleen) cholesterol and triglyceride levels are measured. Anti-rhLAL antibody levels (total, IgG, IgE) are measured.

Survival Study

Figure 38:
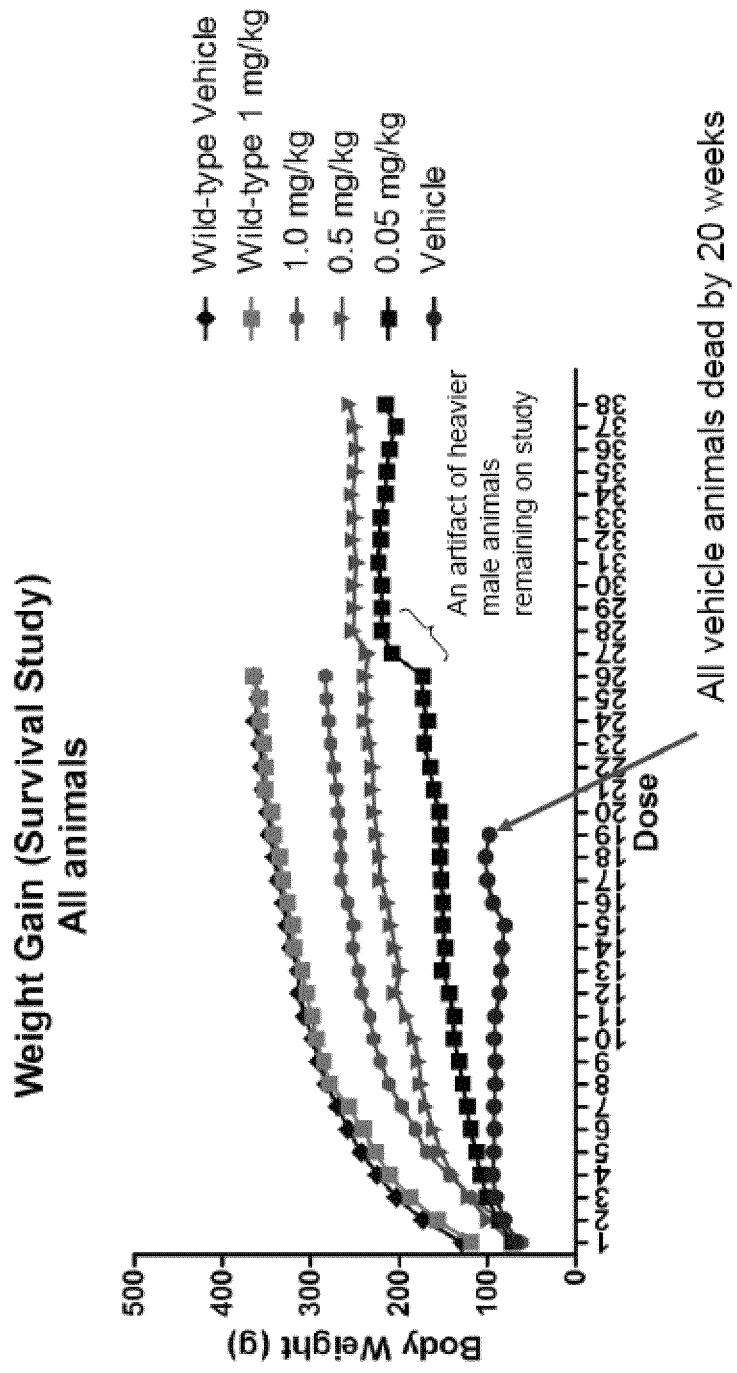
FIG. 38 depicts exemplary weight gain during a survival study. Wild-type rats or homozygous LAL deficient Yoshida rats were treated with various doses of rhLAL (e.g., 0.05 mg/kg, 0.5 mg/kg, 1 mg/kg) or a vehicle control, weekly for up to 38 weeks for survival dose studies.
Figure 39:
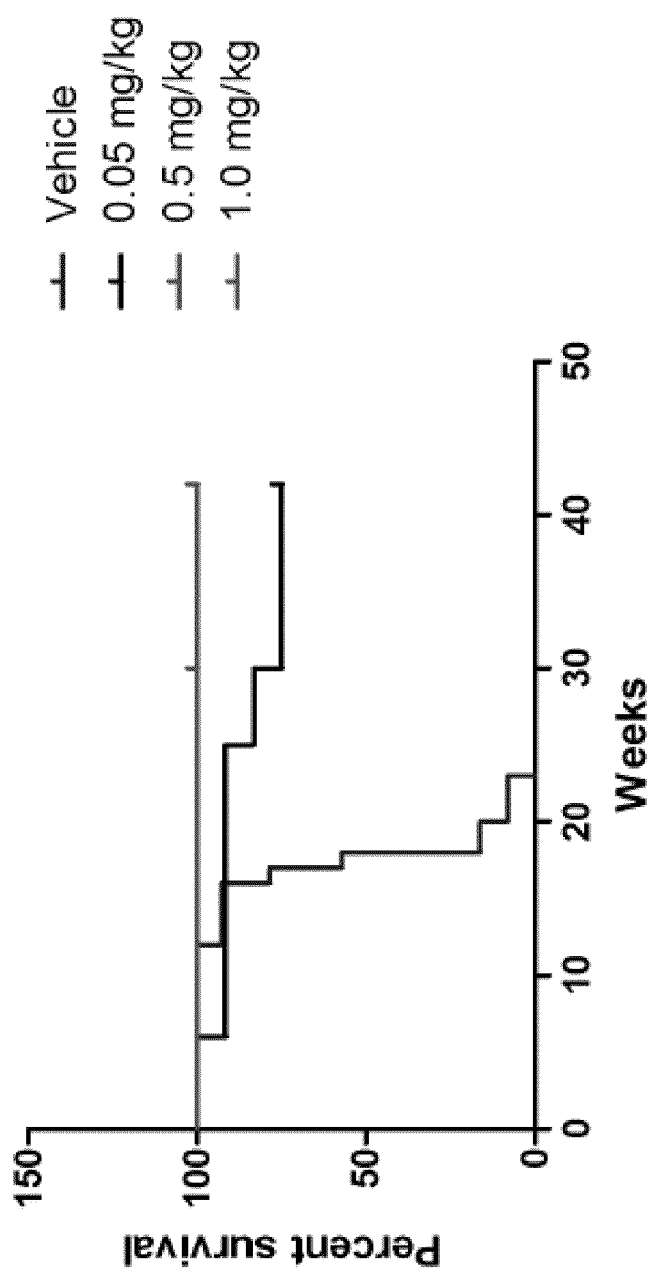
FIG. 39 depicts exemplary percent survival during a survival study. Wild-type rats or homozygous LAL deficient Yoshida rats were treated with various doses of rhLAL (e.g., 0.05 mg/kg, 0.5 mg/kg, 1 mg/kg) or a vehicle control, weekly for up to 38 weeks for survival dose studies.

The purpose of this study was to determine whether weekly intravenous delivery of rhLAL could double mean survival in the LAL deficient Yoshida rat. An exemplary study design for the survival study is shown in FIG. 37. Weight gain during the survival study in all animals (male and female combined) are shown in FIG. 38. Survival analysis of LAL deficient Yoshida rats treated with various doses of rhLAL via weekly intravenous injections for up to 38 doses are shown in FIG. 39. As can be seen, weekly intravenous doses of rhLAL more than doubled the mean life span of the LAL deficient Yoshida rat. Body weight gain in treated animals (1 mg/kg rhLAL weekly) followed a similar trajectory as wild-type animals., however, LAL deficient Yoshida rats did not regain the body weight deficiency that was apparent at 5 weeks of age when the first dose of rhLAL was given.

Clearance and Maintenance Study

Figure 41:
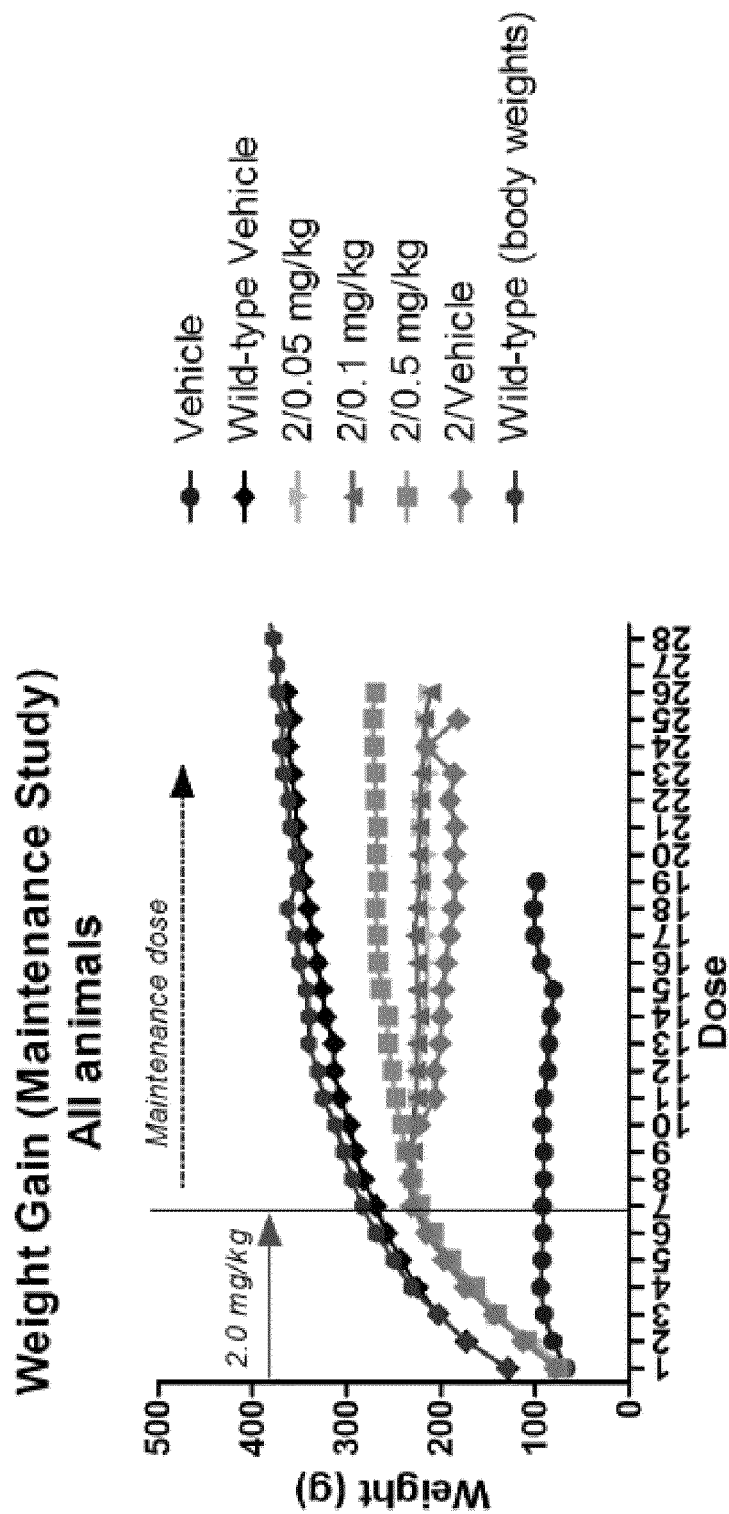
FIG. 41 depicts exemplary weight gain during a clearance and maintenance study. Wild-type rats or homozygous LAL deficient Yoshida rats were treated with a 2 mg/kg "loading dose" of rhLAL weekly followed by various amounts rhLAL weekly for maintenance dose studies.
Figure 42:
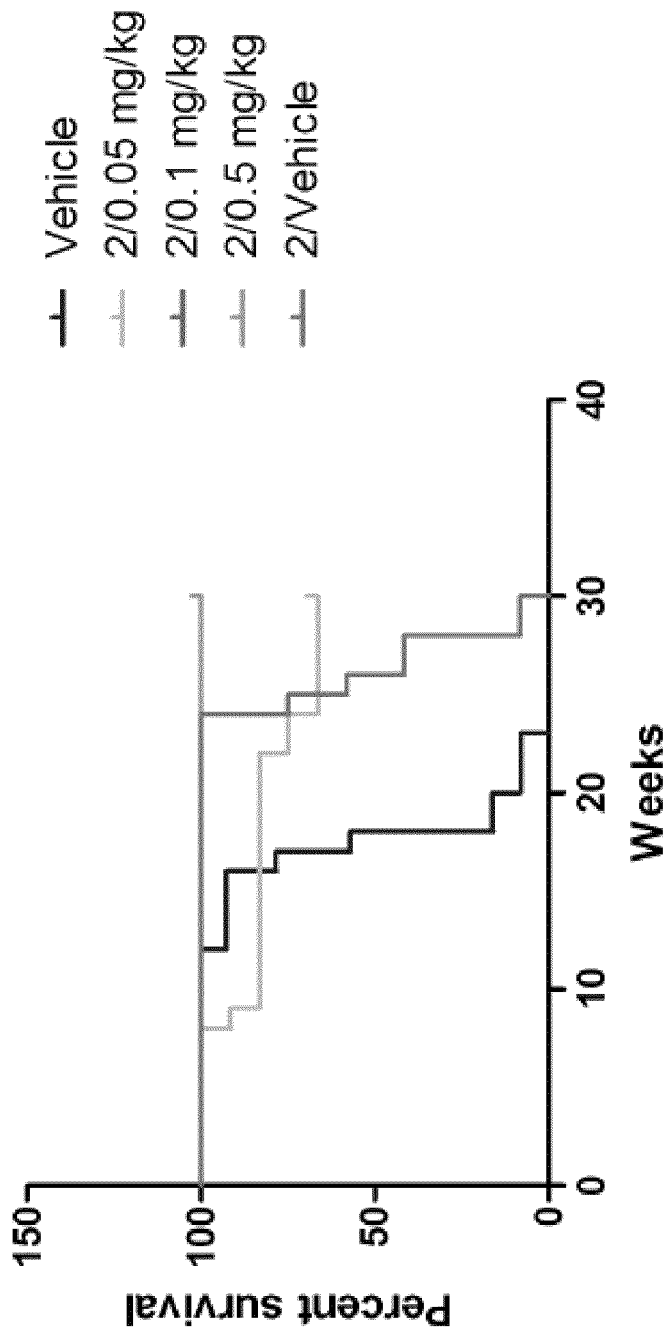
FIG. 42 depicts exemplary percent survival during a clearance and maintenance study. Wild-type rats or homozygous LAL deficient Yoshida rats were treated with a 2 mg/kg "loading dose" of rhLAL weekly followed by various amounts rhLAL weekly for maintenance dose studies.

The purpose of this study was to determine whether lipids could be cleared from the liver by a short-term high dose of rhLAL and then maintenance of animals at a lower weekly dose of rhLAL. An exemplary study design for the clearance and maintenance study is shown in FIG. 40. Weight gain during the clearance and maintenance study in all animals (male and female combined) are shown in FIG. 41. Survival analysis of LAL deficient Yoshida rats treated with a loading dose and various maintenance doses of rhLAL are shown in FIG. 42. Giving the LAL deficient Yoshida rats a short-term (e.g., 4 weeks) higher dose of rhLAL (2 mg/kg) effectively reduced accumulated lipids in the liver. Continuing treatment with a low weekly maintenance dose of rhLAL (0.1 mg/kg weekly) resulted in maintenance of body weight and improvement in survival of treated animals.

Example 4

Figure 44:
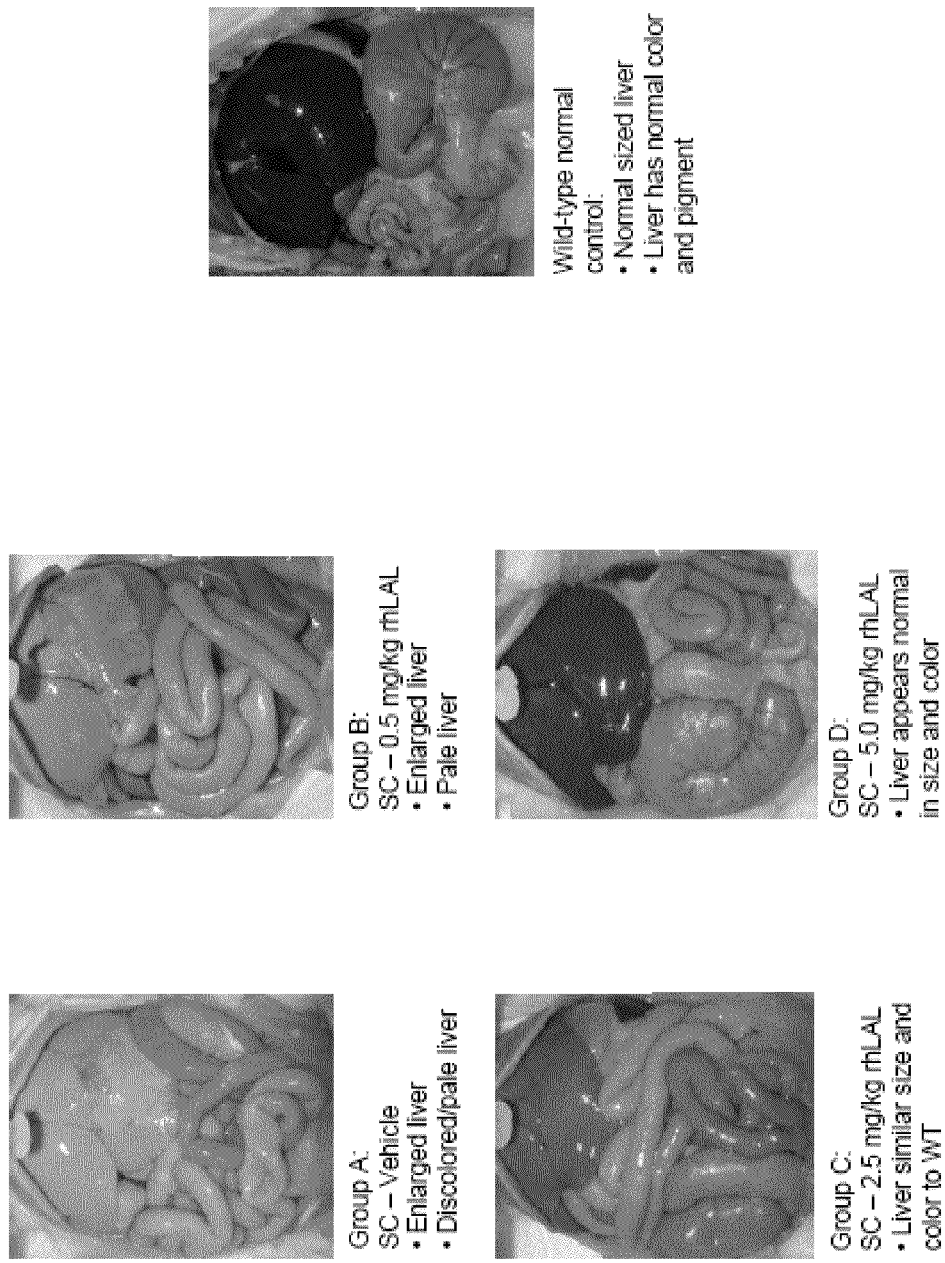
FIG. 44 depicts an exemplary gross liver pathology analysis of wild-type rats or homozygous LAL deficient Yoshida rats treated with various amounts of rhLAL delivered subcutaneously (SC) or intravenously (IV).

Pharmacodynamic Effect of rhLAL: Comparison of Subcutaneous vs. Intravenous Routes The purpose of this study was to compare subcutaneous (SC) delivery with intravenous (IV) delivery of rhLAL in the LAL deficient Yoshida rat. An exemplary study design for the pharmacodynamic study is shown in FIG. 43. Male LAL deficient Yoshida rats were administered 0.5 mg/kg SC, 2.5 mg/kg SC, or 0.5 mg/kg IV weekly for 5 weeks starting at 5 weeks of age. Gross liver pathology of LAL deficient Yoshida rats treated with various doses of rhLAL via SC or IV administration are shown in FIG. 44. As can be seen, Group A (SC, vehicle) has an enlarged, discolored/pale liver; Group B (SC, 0.5 mg/kg rhLAL) has an enlarged, pale liver; Group C (SC, 2.5 mg/kg rhLAL) has a liver similar in size and color to wild-type; and Group D (IV, 0.5 mg/kg rhLAL) has a liver that appears to be of normal size and color. Percent body weight change (FIG. 45A) and relative liver weight (FIG. 45B) in LAL deficient Yoshida rats treated with various doses of rhLAL via SC or IV administration are shown in FIGS. 45A and 45B. A lower body weight gain was observed over the course of treatment in animals administered SC vehicle and SC 0.5 mg/kg rhLAL.

Animals treated with SC 2.5 mg/kg and IV 0.5 mg/kg had increased body weight over the course of the rhLAL treatment. A dose response was observed in liver and spleen weights when compared as a percentage of total body weight. The SC 2.5 mg/kg rhLAL treated animals approximate the IV 0.5 mg/kg rhLAL treated animals in relative organ weights for both liver and spleen.

Figure 46:
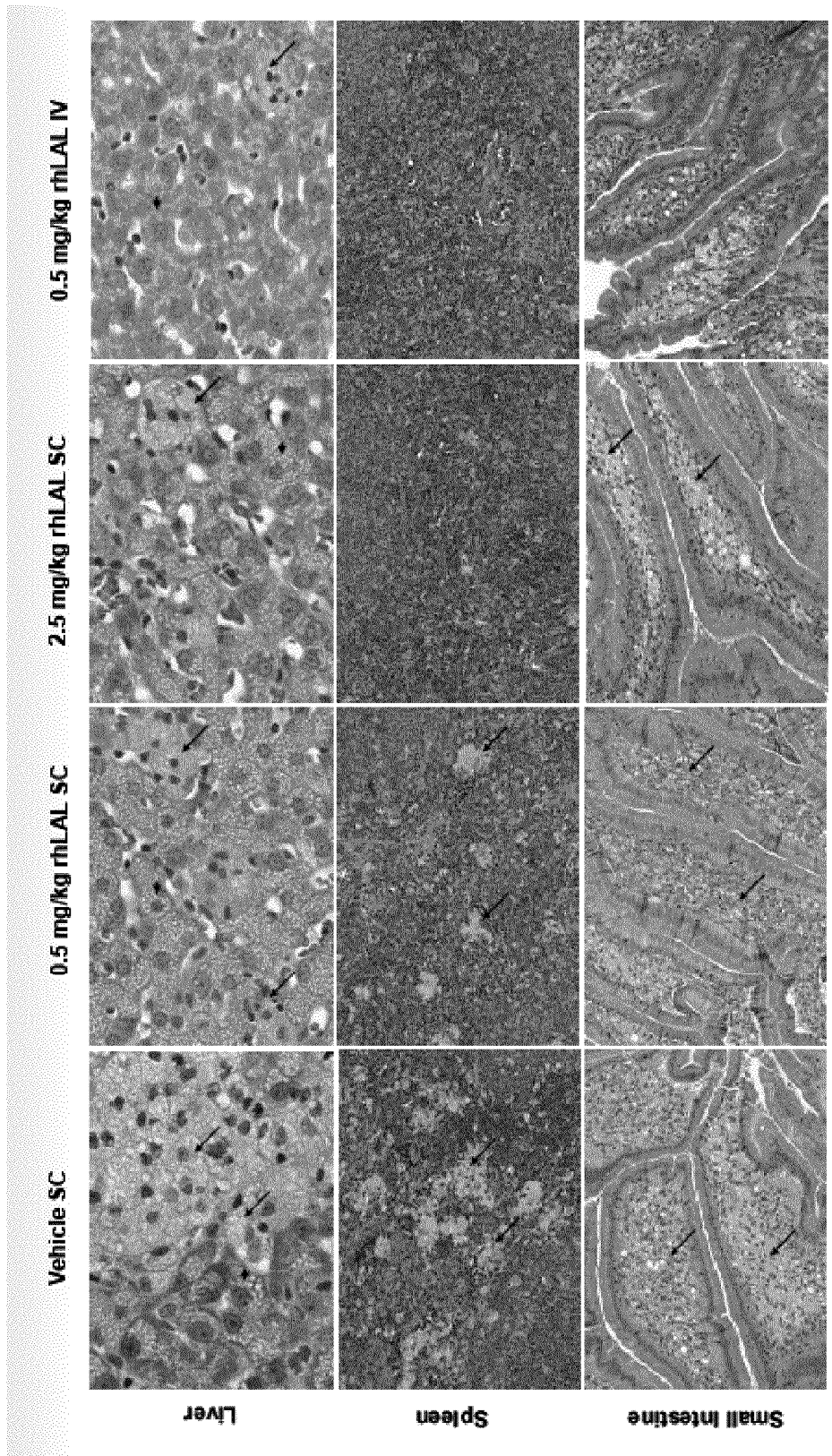
FIG. 46 depicts an exemplary morphological analysis by H&E staining of liver, spleen and small intestine of wild-type rats or homozygous LAL deficient Yoshida rats treated with various amounts of rhLAL delivered subcutaneously (SC) or intravenously (IV).
Figure 47:
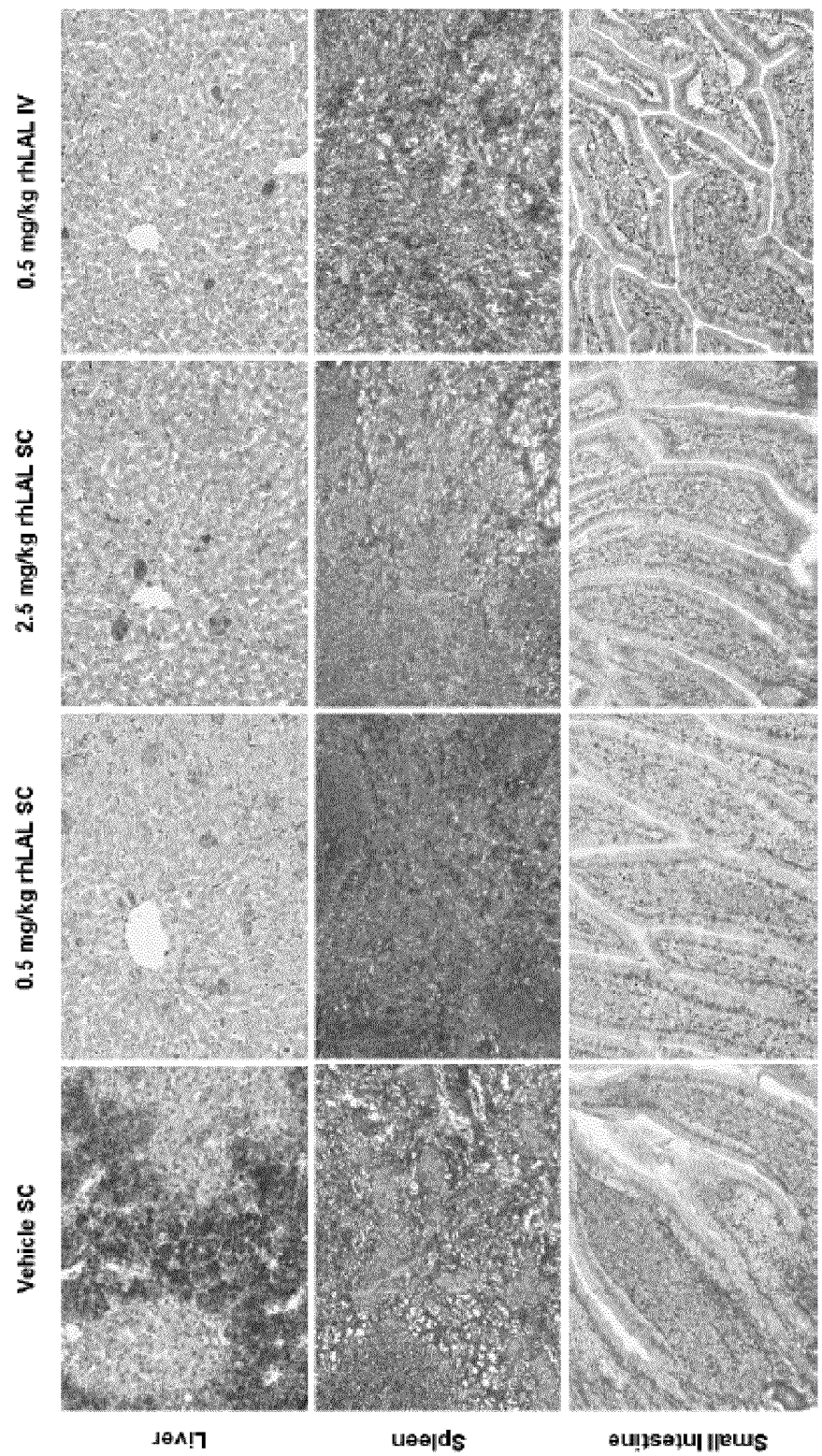
FIG. 47 depicts an exemplary lipid storage analysis by Oil Red O staining of liver, spleen and small intestine of wild-type rats or homozygous LAL deficient Yoshida rats treated with various amounts of rhLAL delivered subcutaneously (SC) or intravenously (IV).

Morphological and lipid storage analyses were performed using H&E and Red Oil O staining, respectively. As can be seen in FIG. 46, a morphological improvement is seen by H&E staining of liver, spleen and small intestine of rhLAL treated animals. Gross observations support a dose-response in the liver. As can be seen in FIG. 47, lipid storage in liver, spleen and small intestine were reduced in rhLAL treated animals. Overall, affected animals treated with rhLAL SC injection demonstrated a dose-dependent and marked morphological and lipid storage improvements in the liver, spleen and small intestine. It was observed that treatment with SC injection of 2.5 mg/kg rhLAL induced similar morphological improvements and lipid storage reduction as treatment with IV injection of 0.5 mg/kg rhLAL.

Taken together, these results demonstrate that subcutaneous administration of rhLAL is effective in treating various symptoms of LALD disease. Affected animals treated with rhLAL subcutaneous injection demonstrated a dose-dependent and marked morphological and lipid storage improvements in the spleen, liver and small intestine. For example, a dose response was observed in liver and spleen weights when compared as percentage of body weight. In addition, the subcutaneous 2.5 mg/kg dose approximates intravenous 0.5 mg/kg dose in both liver and spleen morphological improvement and lipid storage reduction.

Equivalents

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. The articles "a", "an", and "the" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses variations, combinations, and permutations in which one or more limitations, elements, clauses, descriptive terms, etc., from one or more of the claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth herein. It should also be understood that any embodiment of the invention, e.g., any embodiment found within the prior art, can be explicitly excluded from the claims, regardless of whether the specific exclusion is recited in the specification.

It should also be understood that, unless clearly indicated to the contrary, in any methods claimed herein that include more than one act, the order of the acts of the method is not necessarily limited to the order in which the acts of the method are recited, but the invention includes embodiments in which the order is so limited. Furthermore, where the claims recite a composition, the invention encompasses methods of using the composition and methods of making the composition. Where the claims recite a composition, it should be understood that the invention encompasses methods of using the composition and methods of making the composition.

Incorporation of References

All publications and patent documents cited in this application are incorporated by reference in their entirety to the same extent as if the contents of each individual publication or patent document were incorporated herein.

What is claimed is:

1. A method of treating a lysosomal acid lipase deficiency (LALD) disease, comprising administering subcutaneously to an individual suffering from or susceptible to the LALD disease a therapeutically effective amount of a lysosomal acid lipase periodically at an administration interval, wherein a therapeutically effective amount of lysosomal acid lipase for the subcutaneous administration is about 5-fold more than a therapeutically effective amount of lysosomal acid lipase for intravenous administration.

2. The method of claim 1, wherein the LALD disease is Wolman's disease.

3. The method of claim 1, wherein the LALD disease is cholesteryl ester storage disease (CESD).

* * * * *